US008685977B2

(12) United States Patent
Bell et al.

(10) Patent No.: US 8,685,977 B2
(45) Date of Patent: Apr. 1, 2014

(54) CHEMICAL COMPOUNDS

(75) Inventors: Andrew Simon Bell, Sandwich (GB);
Alan Daniel Brown, Sandwich (GB);
Russell Andrew Lewthwaite, Sandwich (GB); Ian Roger Marsh, Sandwich (GB); David Simon Millan, Sandwich (GB); Manuel Perez Pacheco, Sandwich (GB); David James Rawson, Sandwich (GB); Nunzio Sciammetta, Sandwich (GB); Robert Ian Storer, Sandwich (GB); Paul Anthony Stupple, Sandwich (GB); Nigel Alan Swain, Sandwich (GB); Marcel John De Groot, Sandwich (GB)

(73) Assignee: Pfizer Limited, Sandwich (GB)

(*) Notice: Subject to any disclaimer, the term of this patent is extended or adjusted under 35 U.S.C. 154(b) by 393 days.

(21) Appl. No.: 13/179,585

(22) Filed: Jul. 11, 2011

(65) Prior Publication Data

US 2012/0010207 A1    Jan. 12, 2012

Related U.S. Application Data

(60) Provisional application No. 61/363,355, filed on Jul. 12, 2010, provisional application No. 61/473,287, filed on Apr. 8, 2011, provisional application No. 61/488,972, filed on May 23, 2011.

(51) Int. Cl.
*A01N 43/58*    (2006.01)
*A61K 31/50*    (2006.01)
*A01N 43/40*    (2006.01)
*A61K 31/435*   (2006.01)
*A01N 43/56*    (2006.01)
*A61K 31/415*   (2006.01)
*A01N 43/36*    (2006.01)
*A61K 31/40*    (2006.01)

(52) U.S. Cl.
USPC ............ 514/247; 514/277; 514/403; 514/408

(58) Field of Classification Search
USPC .................. 514/247, 277, 403, 408
See application file for complete search history.

(56) References Cited

U.S. PATENT DOCUMENTS

| 4,744,818 | A  | 5/1988  | Heiba         |
| 5,084,085 | A  | 1/1992  | Theodoridis   |
| 5,851,745 | A  | 12/1998 | Takeuchi      |
| 6,251,827 | B1 | 6/2001  | Ziemer et al. |
| 6,348,474 | B1 | 2/2002  | Kayakiri et al. |
| 6,376,512 | B1 | 4/2002  | Jayyosi et al. |
| 7,772,285 | B2 | 8/2010  | Chaki et al.  |
| 2002/0086887 | A1 | 7/2002 | Augeri et al. |
| 2003/0162818 | A1 | 8/2003 | Ikawa et al.  |
| 2008/0188467 | A1 | 8/2008 | Wong et al.   |
| 2010/0179137 | A1 | 7/2010 | Kamikubo et al. |
| 2011/0201616 | A1 | 8/2011 | Kubota et al. |
| 2012/0010182 | A1 | 1/2012 | Brown et al.  |
| 2012/0010183 | A1 | 1/2012 | Bell et al.   |
| 2013/0109667 | A1 | 5/2013 | Markworth et al. |
| 2013/0109696 | A1 | 5/2013 | Greener et al. |
| 2013/0109701 | A1 | 5/2013 | Brown et al.  |
| 2013/0109708 | A1 | 5/2013 | Brown et al.  |
| 2013/0116285 | A1 | 5/2013 | Bell et al.   |

FOREIGN PATENT DOCUMENTS

| EP | 0003416 A1 | 8/1979 |
| EP | 0029742 | 6/1981 |
| EP | 0023100 A1 | 11/1982 |
| EP | 0194599 | 9/1986 |
| EP | 0281103 | 9/1988 |
| EP | 0325245 | 7/1989 |
| EP | 0399732 | 11/1990 |
| EP | 0412848 | 2/1991 |
| EP | 0453210 | 10/1991 |
| EP | 0570006 | 11/1993 |
| EP | 0585155 | 3/1994 |
| EP | 0620490 | 10/1994 |
| EP | 0684521 | 11/1995 |
| EP | 0753508 | 1/1997 |
| GB | 2266527 | 11/1993 |
| JP | 5289262 | 11/1993 |

(Continued)

OTHER PUBLICATIONS

Naganawa et al., "Further optimization of sulfonamide analogs as EP1 receptor antagonists: Synthesis and evaluation of bioisosteres for the carboxylic acid group", Bioorganic & Medicinal Chemistry, vol. 14(21), pp. 7121-7137 (2006).

(Continued)

*Primary Examiner* — Yong Chong
(74) *Attorney, Agent, or Firm* — J. Michael Dixon

(57) ABSTRACT

The invention relates to sulfonamide derivatives, to their use in medicine, to compositions containing them, to processes for their preparation and to intermediates used in such processes.

More particularly the invention relates to a new sulfonamide Nav1.7 inhibitors of formula (I):

(I)

or a pharmaceutically acceptable salt thereof, wherein $Ar^1$, X, $R^1$, $R^2$, $R^3$, $R^4$ and $R^5$ are as defined in the description.

Nav 1.7 inhibitors are potentially useful in the treatment of a wide range of disorders, particularly pain.

16 Claims, No Drawings

(56) References Cited

FOREIGN PATENT DOCUMENTS

| | | |
|---|---|---|
| JP | 5307242 | 11/1993 |
| JP | 2001075213 | 3/2001 |
| WO | 8801133 | 2/1988 |
| WO | 8904303 | 5/1989 |
| WO | 8904304 | 5/1989 |
| WO | 8904305 | 5/1989 |
| WO | 8912628 | 12/1989 |
| WO | 9104964 A1 | 4/1991 |
| WO | 9300332 | 1/1993 |
| WO | 9413636 | 6/1994 |
| WO | 9421590 | 9/1994 |
| WO | 9604905 | 2/1996 |
| WO | 9609818 | 4/1996 |
| WO | 9900372 | 1/1999 |
| WO | 9916744 | 4/1999 |
| WO | 9920275 | 4/1999 |
| WO | 9947508 | 9/1999 |
| WO | 0039077 | 7/2000 |
| WO | 0064876 | 11/2000 |
| WO | 0066120 | 11/2000 |
| WO | 0136365 | 5/2001 |
| WO | 0166098 | 9/2001 |
| WO | 0224636 | 3/2002 |
| WO | 03042150 | 5/2003 |
| WO | 2004018386 | 3/2004 |
| WO | 2005013914 | 2/2005 |
| WO | 2005080346 | 9/2005 |
| WO | 2005094810 | 10/2005 |
| WO | 2006015158 | 2/2006 |
| WO | 2006045514 | 5/2006 |
| WO | 2006121097 | 11/2006 |
| WO | 2007072782 | 6/2007 |
| WO | 2008025539 | 3/2008 |
| WO | 2008092231 | 8/2008 |
| WO | 2008118758 | 10/2008 |
| WO | 2008149965 | 11/2008 |
| WO | 2009/012242 A2 | 1/2009 |
| WO | 2009/049181 A1 | 4/2009 |
| WO | 2009064250 | 5/2009 |
| WO | 2009064251 | 5/2009 |
| WO | 2009067541 | 5/2009 |
| WO | 2009067621 | 5/2009 |
| WO | 2009080835 | 7/2009 |
| WO | 2009157399 | 12/2009 |
| WO | 2010/079443 | 7/2010 |

OTHER PUBLICATIONS

Pinkerton et al., "Allosteric potentiators of the metabotropic glutamate receptor 2 (mGlu2). Part 3: Identification and biological activity of indanone containing mGlu2 receptor potentiators", Bioorganic & Medicinal Chemistry Letters, vol. 15(6), pp. 1565-1571 (2005).

Ng et al., "Design, Synthesis, and Biological Activity of Novel Factor Xa Inhibitors: 4-Aryloxy Substituents of 2,6-Diphenoxypyridines", Bioorganic & Medicinal Chemistry, vol. 10(3), pp. 657-666 (2002).

Hamill et al., "Development of [11C]L-159,884: A Radiolabelled, Nonpeptide Angiotensin II Antagonist that is Useful for Angiotensin II, AT1 Receptor Imaging", Applied Radiation and Isotopes, vol. 47(2), pp. 211-218 (1996).

Matassa et al., "Synthesis and in Vitro LTD4 Antagonist Activity of Bicyclic and Monocyclic Cyclopentylurethane and Cyclopentylacetamide N-Arylsulfonyl Amides", Journal of Medicinal Chemistry, vol. 33(9), pp. 2621-2629 (1990).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", Journal of Medicinal Chemistry, vol. 33(1), pp. 240-245 (1990).

Brown et al., "Hydroxyacetophenone-Derived Antagonists of the Peptidoleukotriens", Journal of Medicinal Chemistry, vol. 32(4), pp. 807-826 (1989).

Dubois et al., "Dihydrochalcone Sweeteners. A Study of the Atypical Temporal Phenomena", Journal of Medicinal Chemistry, vol. 24(4), pp. 408-428 (1981).

Sobel et al., Journal of Chromatography Biomedical Applications, vol. 183(1), pp. 124-130 (1980).

Substituent effects on the toxicity for a series of herbicides, Roumanian Chemical Quarterly Reviews, 2000, pp. 127-137, 1999, 7(2).

Silverman, Richard B. The Organic Chemistry of Drug Design and Drug Action. 2nd Ed., 2004, pp. 29-32, Elsevier, Burlington, MA.

CHEMICAL COMPOUNDS

This application claims benefit of U.S. Provisional Application No. 61/363,355, filed Jul. 12, 2010; U.S. Provisional Application No. 61/473,287, filed Apr. 8, 2011; and U.S. Provisional Application No. 61/488,972, filed May 23, 2011; each application is hereby incorporated by reference in its entirety for any purpose.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and $Na_v$x.x. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir. (Wien)*, 144(8): 803-10 (2002)). Gain of function mutations of $Na_v1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the nonselective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.*; 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.*; 71(4): 311-9 (2007), Ahmad et al, *Hum Mol. Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v1.7$ inhibitors that are good drug candidates.

Prefererably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

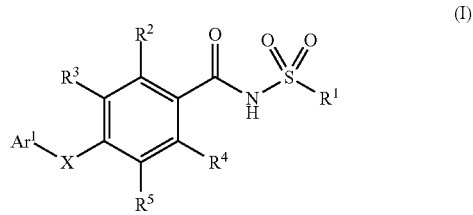

or a pharmaceutically acceptable salt thereof, wherein
X is O, S, NH or $CH_2$;
$Ar^1$ is (i) naphthyl; or (ii) naphthyl or phenyl each of which is independently substituted by one to three Y;

Y is F; Cl; CN; $(C_1-C_8)$alkyl, optionally substituted by $(C_3-C_8)$cycloalkyl and/or, valency permitting, by one to eight F; $(C_3-C_8)$cycloalkyl, optionally substituted, valency permitting, by one to eight F; $NR^7R^8$; $(C_1-C_8)$alkyloxy, optionally independently substituted by one to three $R^9$, or, valency permitting, by one to eight F; $(C_3-C_8)$cycloalkyloxy; phenyl, optionally independently substituted by one to three $R^{10}$; $Het^1$ and $Het^2$; wherein $(C_3-C_8)$cycloalkyloxy may be optionally fused to a phenyl ring or may be independently substituted by one to three $R^{10}$;

$R^1$ is $(C_1-C_6)$alkyl or $(C_3-C_8)$cycloalkyl, each of which is optionally substituted, valency permitting, by one to eight F;

$R^2$, $R^3$, $R^4$ are independently H, F, Cl or —$OCH_3$;

$R^5$ is H, CN, F, Cl or $R^6$;

$R^6$ is a group selected from $(C_1-C_6)$alkyl and $(C_1-C_6)$alkyloxy, wherein each group is optionally substituted, valency permitting, by one to eight F;

$R^7$ and $R^8$ are independently H; $(C_1-C_8)$alkyl, optionally independently substituted by one to three $R^{11}$; $(C_3-C_8)$cycloalkyl; or 'C-linked' $Het^1$; wherein $(C_3-C_8)$cycloalkyl may be optionally fused to a phenyl ring or may be independently substituted by one to three $R^{10}$; or $R^7$ and $R^8$, taken together with the nitrogen atom to which they are attached, form a saturated, bridged, 7- to 9-membered ring;

$R^9$ is $(C_1-C_6)$alkyloxy; $(C_3-C_8)$cycloalkyl, optionally substituted, valency permitting, by one to eight F; $Het^1$; or phenyl, optionally independently substituted by one to three $R^6$;

$R^{10}$ is F, Cl or $R^6$;

$R^{11}$ is F; $(C_1-C_6)$alkyloxy; $(C_3-C_8)$cycloalkyl, optionally substituted, valency permitting, by one to eight F; 'C-linked' $Het^1$; or phenyl, optionally independently substituted by one to three $R^6$;

$Het^1$ is a 3- to 8-membered saturated monoheterocycloalkyl comprising one or two ring members selected from —$NR^{12}$— and —O—, said monoheterocycloalkyl being optionally substituted on a ring carbon atom by one to three substituents independently selected from F, $(C_1-C_6)$alkyl, $(C_1-C_4)$alkyloxy$(C_0-C_4)$alkylene and $(C_3-C_8)$cycloalkyl;

$Het^2$ is a 5- or 6-membered heteroaryl comprising one to three nitrogen atoms, said heteroaryl being optionally substituted by one to three substituents selected from F, Cl, CN and $R^6$; and $R^{12}$ is H, $(C_1-C_6)$alkyl or $(C_3-C_8)$cycloalkyl, wherein $(C_1-C_6)$alkyl and $(C_3-C_8)$cycloalkyl are optionally substituted, valency permitting, by one to eight F; or, when $Het^1$ is 'N-linked', is absent.

Described below are a number of embodiments (E) of this first aspect of the invention, where for convenience E1 is identical thereto.

E1 A compound of formula (I) as defined above or a pharmaceutically acceptable salt thereof.

E2 A compound according to E1 wherein $Ar^1$ is phenyl independently substituted by one to three Y.

E3 A compound according to either E1 or E2 wherein $Ar^1$ is phenyl independently substituted by one or two Y.

E4 A compound according to any of E1 to E3 wherein $Ar^1$ is phenyl meta-substituted by Y, para-substituted by Y, or meta- and para-substituted by independent Y.

E5 A compound according to any of E1 to E4 wherein Y is F; Cl; CN; $(C_1-C_8)$alkyl, optionally substituted by $(C_3-C_8)$cycloalkyl and/or, valency permitting, by one to eight F; $(C_3-C_8)$cycloalkyl, optionally substituted, valency permitting, by one to eight F; $(C_1-C_6)$alkyloxy, optionally substituted, valency permitting, by one to eight F; or $(C_3-C_8)$cycloalkyloxy.

E6 A compound according to any of E1 to E5 wherein Y is F; Cl; CN; $(C_1-C_4)$alkyl, optionally substituted by $(C_3-C_6)$cycloalkyl and/or, valency permitting, by one to eight F; $(C_3-C_6)$cycloalkyl, optionally substituted, valency permitting, by one to eight F; $(C_1-C_6)$alkyloxy, optionally substituted by one to three F; or $(C_3-C_6)$cycloalkyloxy.

E7 A compound according to any of E1 to E6 wherein $R^1$ is $(C_1-C_4)$alkyl or $(C_3-C_6)$cycloalkyl.

E8 A compound according to any of E1 to E7 wherein $R^1$ is $(C_1-C_3)$alkyl or $(C_3-C_4)$cycloalkyl.

E9 A compound according to any of E1 to E8 wherein $R^1$ is methyl or cyclopropyl.

E10 A compound according to any of E1 to E9 wherein $R^2$, $R^3$ and $R^4$ are independently H, F or Cl.

E11 A compound according to any of E1 to E10 wherein $R^2$, $R^3$ and $R^4$ are independently H or F.

E12 A compound according to any of E1 to E11 wherein $R^2$ is F; and $R^3$ and $R^4$ are independently H or F.

E13 A compound according to any of E1 to E12 wherein $R^5$ is H; CN; F; Cl; $(C_1-C_4)$alkyl, optionally substituted, valency permitting, by one to eight F; or $(C_1-C_4)$alkyloxy, optionally substituted, valency permitting, by one to eight F.

E14 A compound according to any of E1 to E13 wherein $R^5$ is H, CN, F, Cl, $CH_3$, $C_2H_5$, $CF_3$, —$OCH_3$, —$OC_2H_5$ or —$OCF_3$.

E15 A compound according to any of E1 to E14 wherein $R^5$ is F or Cl.

Described below are a number of additional embodiments (EM) of this first aspect of the invention.

EM1 A compound of formula (I)

(I)

or a pharmaceutically acceptable salt thereof, wherein

X is O;

$Ar^1$ is (i) naphthyl; or (ii) naphthyl or phenyl each of which is independently substituted by one to three Y;

Y is F; Cl; CN; $(C_1-C_8)$alkyl, optionally substituted by $(C_3-C_8)$cycloalkyl or one to three F; $(C_3-C_8)$cycloalkyl, optionally substituted by one to three F; $NR^7R^8$; $(C_1-C_8)$alkyloxy, optionally independently substituted by one to three $R^9$; $(C_3-C_8)$cycloalkyloxy; phenyl, optionally independently substituted by one to three $R^{10}$; $Het^1$ or $Het^2$; wherein $(C_3-C_8)$cycloalkyloxy may be optionally fused to a phenyl ring or may be independently substituted by one to three $R^{19}$;

$R^1$ is $(C_1-C_6)$alkyl or $(C_3-C_8)$cycloalkyl, each of which is optionally substituted by one to three F;

$R^2$, $R^3$, $R^4$ are independently H, F, Cl or —$OCH_3$;

$R^5$ is H, CN, F, Cl or $R^6$;

$R^6$ is a group selected from $(C_1-C_6)$alkyl and $(C_1-C_6)$alkyloxy, wherein each group is optionally substituted, valency permitting, by one to five F;

$R^7$ and $R^8$ are independently H; $(C_1-C_8)$alkyl, optionally independently substituted by one to three $R^{11}$; $(C_3-C_8)$cycloalkyl; or 'C-linked' $Het^1$; wherein $(C_3-C_8)$cycloalkyl may be optionally fused to a phenyl ring or may be independently substituted by one to three $R^{19}$; or $R^7$ and $R^8$, taken together with the nitrogen atom to which they are attached, form a saturated, bridged, 7- to 9-membered ring;

$R^9$ is F; $(C_1-C_6)$alkyloxy; $(C_3-C_8)$cycloalkyl, optionally substituted by one to three F; $Het^1$; or phenyl, optionally independently substituted by one to three $R^6$;

$R^{10}$ is F, Cl or $R^6$;

$R^{11}$ is F; $(C_1-C_6)$alkyloxy; $(C_3-C_8)$cycloalkyl, optionally substituted by one to three F; 'C-linked' $Het^1$; or phenyl, optionally independently substituted by one to three $R^6$;

$Het^1$ is a 3- to 8-membered saturated monoheterocycloalkyl comprising one or two ring members selected from —$NR^{12}$— and —O—, said monoheterocycloalkyl being optionally substituted on a ring carbon atom by one to three substituents independently selected from F, $(C_1-C_6)$alkyl, $(C_1-C_4)$alkyloxy$(C_0-C_4)$alkylene and $(C_3-C_8)$cycloalkyl;

$Het^2$ is a 5- or 6-membered heteroaryl comprising one to three nitrogen atoms, said heteroaryl being optionally substituted by one to three substituents selected from F, Cl, CN and $R^6$; and $R^{12}$ is H, $(C_1-C_6)$alkyl or $(C_3-C_8)$cycloalkyl, wherein $(C_1-C_6)$alkyl and $(C_3-C_8)$cycloalkyl are optionally substituted by one to three F; or, when $Het^1$ is 'N-linked', is absent.

EM2 A compound according to EM1 wherein $Ar^1$ is phenyl independently substituted by one to three Y.

EM3 A compound according to either EM1 or EM2 wherein $Ar^1$ is phenyl independently substituted by one or two Y.

EM4 A compound according to any of EM1 to EM3 wherein $Ar^1$ is phenyl meta-substituted by Y, para-substituted by Y, or meta- and para-substituted by independent Y.

EM5 A compound according to any of EM1 to EM4 wherein Y is F; Cl; CN; $(C_1-C_8)$alkyl, optionally substituted by $(C_3-C_8)$cycloalkyl or one to three F; $(C_3-C_8)$cycloalkyl, optionally substituted by one to three F; $(C_1-C_6)$alkyloxy, optionally substituted by one to three F; or $(C_3-C_8)$cycloalkyloxy.

EM6 A compound according to any of EM1 to EM5 wherein Y is F; Cl; CN; $(C_1-C_4)$alkyl, optionally substituted by $(C_3-C_6)$cycloalkyl or one to three F; $(C_3-C_6)$cycloalkyl, optionally substituted by one to three F; $(C_1-C_6)$alkyloxy, optionally substituted by one to three F; or $(C_3-C_6)$cycloalkyloxy.

EM7 A compound according to any of EM1 to EM6 wherein $R^1$ is $(C_1-C_4)$alkyl or $(C_3-C_6)$cycloalkyl.

EM8 A compound according to any of EM1 to EM7 wherein $R^1$ is $(C_1-C_3)$alkyl or $(C_3-C_4)$cycloalkyl.

EM9 A compound according to any of EM1 to EM8 wherein $R^1$ is methyl or cyclopropyl.

EM10 A compound according to any of EM1 to EM9 wherein $R^2$, $R^3$ and $R^4$ are independently H, F or Cl.

EM11 A compound according to any of EM1 to EM10 wherein $R^2$, $R^3$ and $R^4$ are independently H or F.

EM12 A compound according to any of EM1 to EM11 wherein $R^2$ is F; and $R^3$ and $R^4$ are independently H or F.

EM13 A compound according to any of EM1 to EM12 wherein $R^5$ is H; CN; F; Cl; $(C_1-C_4)$alkyl, optionally substituted by one to three F; or $(C_1-C_4)$alkyloxy, optionally substituted by one to three F.

EM14 A compound according to any of EM1 to EM13 wherein $R^5$ is H, CN, F, Cl, $CH_3$, $C_2H_5$, $CF_3$, —$OCH_3$, —$OC_2H_5$ or —$OCF_3$.

EM15 A compound according to any of EM1 to EM14 wherein $R^5$ is F or Cl.

Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, thiazolyl, isothiazolyl, thiadiazolyl, pyridyl, pyridazinyl, pyrimidinyl and pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of $Het^1$ include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K^+$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, $4^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Pro-drugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (–Ph>–PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention. It is open to a person skilled in the art to routinely choose the form of the intermediate compounds which provides the best combination of features for this purpose. Such features include the melting point, solubility, processability and yield of the intermediate form and the resulting ease with which the product may be purified on isolation.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the following general methods, X, $R^1$, $R^2$, $R^3$, $R^4$, $R^5$, and $Ar^1$ are as previously defined for a compound of the formula (I) unless otherwise stated. Pg is a suitable carboxylic acid protecting group such as tert-butyl, methyl, ethyl, or tolyl. Lg is a suitable leaving group, such as halo (e.g. Br) or sulphonate (e.g mesylate, triflate or tosylate). M is an optionally substituted/ligated metal or boron group suitable for cross coupling reactions, such as trialkylstannane, dihydroxyborane, dialkoxyborane or halozinc. E is an aldehyde or nitrile or Lg.

Where ratios of solvents are given, the ratios are by volume.

The skilled person may undertake the synthetic steps described below in any suitable order in order to arrive at the compounds of formula (I).

According to a first process, compounds of formula (I), wherein X is O, S or NH, may be prepared by the process illustrated in Scheme 1.

Scheme 1

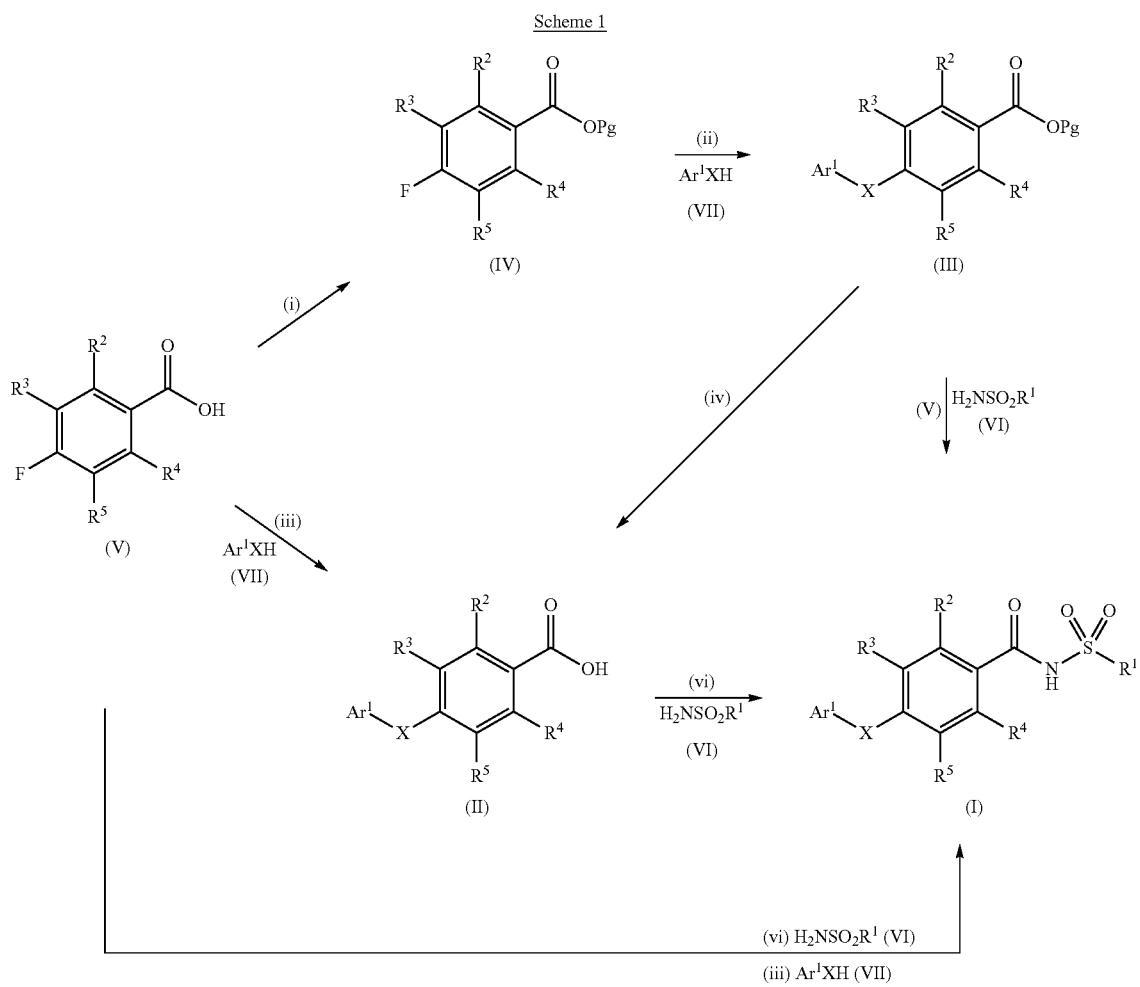

Compounds of formula (I) can be made from compounds of formula (III) according to process step (v) by displacement of the ester with compounds of formula (VI) and a base. Suitable conditions include potassium tert-butoxide in THF at 60° C. or NaH in THF at 70° C. Preferred conditions comprise DBU in acetonitrile at 50° C.

Alternatively compounds of formula (I) can be made from compounds of formula (II) according to reaction step (vi) by activation of the acid group with reagents such as oxalyl chloride, carbonyl di-imidazole (CDI), a uronium based peptide coupling agent or a carbodiimide reagent followed by displacement with a sulfonamide of formula (VI) in the presence of a nucleophilic base such as 4-dimethylaminopyridine. Preferred conditions comprise N,N-dimethylaminopropyl-N'-ethylcarbodiimide and 4-dimethylaminopyridine in DCM or 2-(1H-7-azabenzotriazol-1-yl)-1,1,3,3-tetramethyl uronium hexafluorophosphate and N,N-diisopropylethylamine.

Compounds of formula (I) can also be made from compounds of formula (V) by reversing process steps (iii) and (vi). Preferred conditions for process step (iii) are as previously described, for process step (vi) preferred conditions comprise potassium carbonate in DMSO at 90° C. or NaH in THF at 60° C.

Compounds of formula (III) can be made from compounds of formula (IV) according to process step (ii) by a nucleophilic aromatic substitution reaction (SNAr) using compounds of formula (VII) and a base. Suitable conditions include potassium carbonate in DMF or DMSO, sodium hydride in NMP or DMF, and sodium hydroxide or potassium hydroxide in 1,4-dioxane and water or DMSO. Preferred conditions comprise 2 equivalents of potassium carbonate in DMSO at room temperature to 120° C. or potassium tert-butoxide in THF.

Compounds of formula (IV) can be made from compounds of formula (V) according to process step (i) using protecting group methodology as referred to above in 'Greene's Protective Groups in Organic Synthesis'. When Pg is tolyl, preferred conditions comprise thionyl chloride and para-cresol or carbonyldiimidazole in ethylacetate with para-cresol at 40° C. When Pg is tert-butyl, preferred conditions comprise di-tert-butyldicarbonate and 4-dimethylaminopyridine in tert-butanol.

Compounds of formula (II) can be made from compounds of formula (III) according to process step (iv) by hydrolysis of the ester under basic or acidic conditions. Preferred conditions comprise sodium hydroxide in a mixture of MeOH and THF or lithium hydroxide in a mixture of THF and water or TFA in DCM at room temperature.

Alternatively compounds of formula (II) can be made from compounds of formula (V) according to process step (iii) by a nucleophilic aromatic substitution reaction (SNAr) using compounds of formula (VII) and base as described for process step (ii) at elevated temperatures. Preferred conditions comprise potassium carbonate in DMSO at 90° C.

According to a second process, compounds of formula (II), wherein X is O, S or NH, may also be prepared by the process illustrated in Scheme 2.

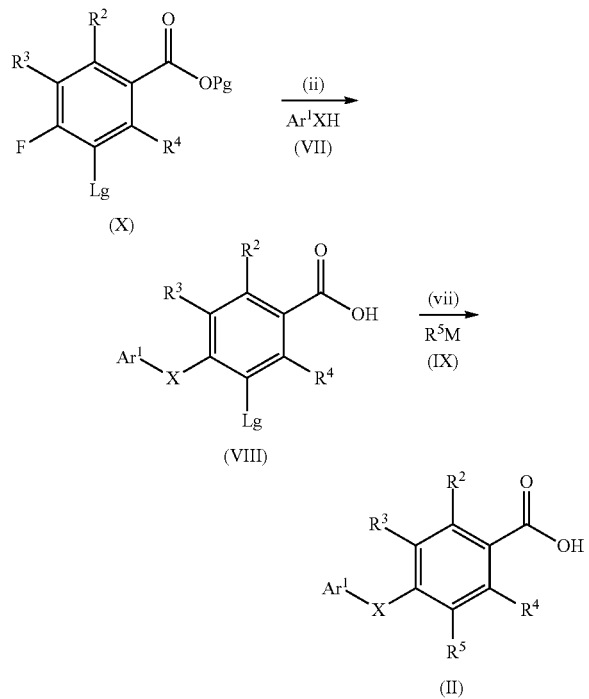

Compounds of formula (II), wherein $R^5$ is a group selected from $(C_1-C_6)$alkyl and $(C_1-C_6)$alkyloxy and wherein each group is optionally substituted, valency permitting, by one to eight F, can be prepared from compounds of formula (VIII) according to process step (vii) using compounds of formula (IX) under Negishi cross coupling conditions. Typical conditions comprise a di$(C_1-C_6)$alkyl zincate in THF with bis (tributylphosphine)palladium (0) in THF at 0° C.

Compounds of formula (VIII) can be made from compounds of formulae (X) and (VII) according to process step (ii) under conditions described in Scheme 1 step (ii). During this process hydrolysis may occur.

According to a third process, compounds of formula (I), wherein X is O, S or NH, may be prepared by the process illustrated in Scheme 3.

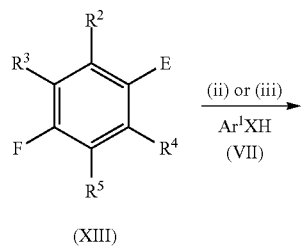

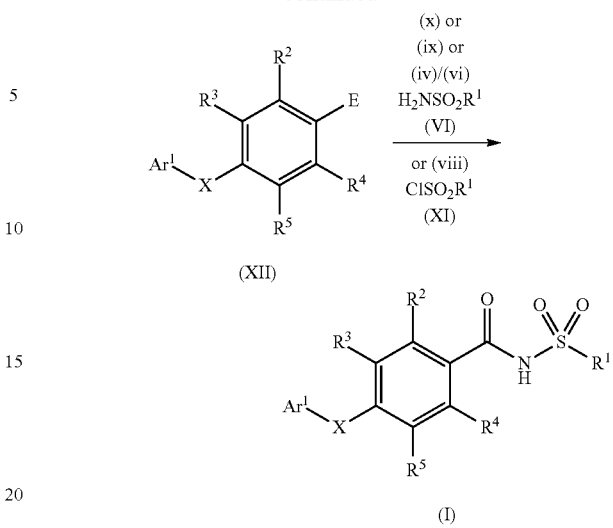

When E is nitrile, compounds of formula (I) can be prepared from compounds of formula (XII) according to reaction step (viii) by hydrolysis of the nitrile by either acidic or basic methods to the primary carboxamide followed by reaction with an appropriate sulfonyl chloride of formula (XI). Preferred conditions comprise hydrogen peroxide and potassium carbonate in DMSO followed by lithium hexamethyldisilazide in THF at 60° C.

Alternatively when E is nitrile compounds of formula (I) can be prepared from compound of formula (XII) according to reaction step (iv) by hydrolysis of the nitrile by either acidic or basic methods to the carboxylic acid, followed by displacement with a sulfonamide of formula (VI) according to process step (vi) under conditions described for Scheme 1 step (vi).

When E is aldehyde, compounds of formula (I) can be prepared from compounds of formula (XII) according to process step (ix), an oxidative rhodium insertion reaction with compounds of formula (VI). Preferred conditions comprise methane sulfonamide, bis(tert-butylcarbonyloxy)iodobenzene and bis[rhodium(alpha, alpha,alpha', alpha'-tetramethyl-1,3-benzenediproprionic acid)] in isopropyl acetate at 55° C.

When E is Lg, such as Br, I or triflate, compounds of formula (I) can be prepared from compounds of formulae (XII) and (VI) according to process step (x), a carbonylation reaction followed by carboamidation. Conveniently the reaction is effected using a carbonyl source such as molybdenumhexacarbonyl or carbon monoxide, a palladium catalyst such as trans-bis(acetato)bis[o-(di-o-tolylphosphino)benzyl]dipalladium(II) acetate, a phosphine ligand such as tri-tert-butylphosphonuim tetrafluoroborate, a base such as triethylamine and at 50-150° C. under pressure or under microwave irradiation for 10 minutes to 24 hours in a solvent such as THF, NMP or 1,4-dioxane. Preferred conditions comprise molybdenumhexacarbonyl, trans-bis(acetato)bis[o-(di-o-tolylphosphino)benzyl]dipalladium(II) acetate, tri-tert-butylphosphonuim tetrafluoroborate and 1,8-diazabicyclo [5.4.0]undec-7-ene in 1,4-dioxan under microwave irradiation at 140° C. for 15 minutes.

According to a fourth process, compounds of formula (I), wherein X is $CH_2$, may be prepared by the process illustrated in Scheme 4.

Scheme 4

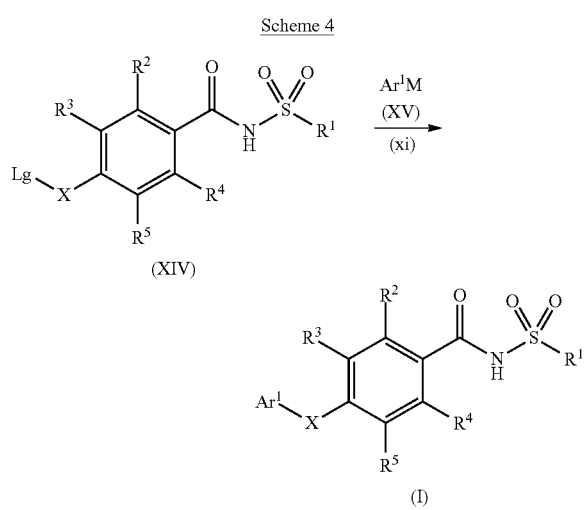

Compounds of formula (I) can be made from compounds of formula (XIV) according to process step (xi) under Suzuki cross coupling reaction with compounds of formula (XV) and a suitable catalyst. Typical conditions comprise Palladium tetrakis triphenyl phosphine and potassium carbonate in water and THF at 65° C.

Compounds of formulae (V), (VI), (VII), (IX), (X), (XI), (XIII), (XIV) and (XV) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous.

Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™ Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia-Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
an alternative Nav1.7 channel modulator, such as another compound of the present invention or a compound disclosed in WO 2009/012242;
an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;
a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene-1-carboxamide);

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5\text{-HT}_{1B/1D}$ agonist such as eletriptan, sumatriptan, naratriptan, zolmitriptan or rizatriptan;

a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);

a $5\text{-HT}_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5- methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a microsomal prostaglandin E synthase type 1 (mPGES-1) inhibitor;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid,
$Cs_2CO_3$ is caesium carbonate;
$Cu(acac)_2$ is copper (II) acetylacetonate;
CuI is copper (I) iodide;
$Cu(OAc)_2$ is copper (II) acetate;
DAD is diode array detector;
DCM is dichloromethane; methylene chloride;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCl is 1-(3-dimethylaminopropyl)-3-ethylcarbodiimide hydrochloride;
EDTA is ethylenediaminetetraacetic acid;
ELSD is evaporative light scattering detection;
$Et_2O$ is diethyl ether;
EtOAc is ethyl acetate;
EtOH is ethanol;
HCl is hydrochloric acid;
IPA is isopropanol;

Ir$_2$(OMe)$_2$COD$_2$ is bis(1,5-cyclooctadiene)di-µ-methoxydiiridium (I);
K$_2$CO$_3$ is potassium carbonate;
KHSO$_4$ is potassium hydrogen sulphate;
KOAc is potassium acetate;
KOH is potassium hydroxide;
K$_3$PO$_4$ is potassium phosphate tribasic;
LCMS is liquid chromatography mass spectrometry (R$_t$=retention time);
LiHMDS is lithium hexamethyldisilazide;
LiOH is lithium hydroxide;
MeOH is methanol;
MgSO$_4$ is magnesium sulphate;
NaH is sodium hydride;
NaHCO$_3$ is sodium hydrogencarbonate;
Na$_2$CO$_3$ is sodium carbonate;
NaHSO$_3$ is sodium bisulphate;
NaHSO$_4$ is sodium hydrogensulphate;
NaOH is sodium hydroxide;
Na$_2$SO$_4$ is sodium sulphate;
NH$_4$Cl is ammonium chloride;
NMP is N-Methyl-2-pyrrolidone;
Pd/C is palladium on carbon;
Pd(PPh$_3$)$_4$ is palladium tetrakis;
Pd(dppf)$_2$Cl$_2$ is [1,1'-bis(diphenylphosphino)ferrocene]dichloropalladium(II), complex with dichloromethane;
THF is tetrahydrofuran;
THP is tetrahydropyran;
TLC is thin layer chromatography;
TMSCl is trimethylsilyl chloride; and
WSCDl is 1-(3-dimethylaminopropyl)-3-ethylcarbodiimide hydrochloride.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol.

Mass spectra, MS (m/z), were recorded using either electrospray ionisation (ESI) or atmospheric pressure chemical ionisation (APCI). When relevant, m/z data provided may include isotopes $^{35}$Cl, $^{37}$Cl, $^{79}$Br, $^{81}$Br and combinations thereof.

Automated Preparative High Performance Liquid Chromatography (Auto-HPLC)

Certain compounds of the Examples and Preparations were purified using Automated Preparative High Performance Liquid Chromatography (HPLC). Reversed-phase HPLC conditions were either on Fraction Lynx systems or on a Trilution system.

In the case of the Fractionlynx system, Samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 µm). B-HPLC was carried out on an Xterra Prep MS C18 (19×100 mm, 5 µm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 30 v | Capillary: 3.20 kv |
| ES− Cone voltage: −30 v | Capillary: −3.00 kv |
| Desolvation gas: 600 L/hr | |
| Source Temp: 120° C. | |
| Scan range 150-900 Da | |

The fraction collection was triggered by both MS and ELSD.

Quality control (QC) analysis was performed using a LCMS method. Acidic runs were carried out on a Sunfire C18 (4.6×50 mm, 5 µm), basic runs were carried out on a Xterra C18 (4.6×50 mm, 5 µm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

| | |
|---|---|
| ES+ Cone voltage: 25 v | Capillary: 3.30 kv |
| ES− Cone voltage: −30 v | Capillary: −2.50 kv |
| Desolvation gas: 800 L/hr | |
| Source Temp: 150° C. | |
| Scan range 160-900 Da | |

Where the reversed-phase Trilution system was used (T-HPLC) the conditions were as follows:
Mobile phase A: 0.1% formic acid in water
Mobile phase B: 0.1% formic acid in acetonitrile
Column: Phenomenex C18 Luna 21.5 mm×15 cm with 5 micron particle size
Gradient: 95-5% A over 15 min, 15 min hold, 15 ml/min flow rate
UV: 200 nm-400 nm
Temperature: Room temperature
Liquid Chromatography Mass Spectrometry Unless carried out by Auto-HPLC (under conditions of A-HPLC or B_HPLC) as described just above, or as specifically set out in the Examples and Preparations that follow, LCMS conditions were run according to one of the conditions given below (where ratios of solvents are given, the ratios are by volume):
Acidic 2 Minute LCMS
Mobile phase A: 0.1% formic acid in water
Mobile phase B: 0.1% formic acid in 70% methanol: 30% isopropanol
Column: C18 phase Phenomenex 20×4.0 mm with 3 micron particle size Gradient: 98-10% A over 1.5 min, 0.3 min hold, 0.2 re-equilibration, 2 ml/min flow rate
UV: 210 nm-450 nm DAD
Temperature: 75° C.
Or
Mobile phase A: 0.1% formic acid in water
Mobile phase B: 0.1% formic acid in acetonitrile
Column: C18 phase Phenomenex 20×4.0 mm with 3 micron particle size
Gradient: 70-2% A over 1.5 min, 0.3 min hold, 0.2 re-equilibration, 1.8 ml/min flow rate
UV: 210 nm-450 nm DAD
Temperature: 75° C.
Acidic 4.5 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 1 min hold, 0.2 min re-equilibration, 2.0 ml/min flow rate
UV: 220 nm-254 nm DAD
Temperature: 40° C.
Acidic 8 Minute LCMS
Mobile phase A: 0.05% formic acid in water
Mobile phase B: acetonitrile
Column: Phenomenex Gemini C18 45×45 mm with 5 micron particle size
Gradient: 80-50% A over 0.5 min, 50-2% A over 3 min, 4.5 min hold, 0.2 min re-equilibration, 2.0 ml/min flow rate
UV: 220 nm-254 nm DAD
Temperature: 40° C.
Acidic 6 Minute LCMS
Mobile phase A: 0.1% formic acid in water
Mobile phase B: 0.1% formic acid in acetonitrile
Column: C18 phase Waters Sunfire 50×4.6 mm with 5 micron particle size
Gradient: 95-5% A over 3 min, 1 min hold, 2 min re-equilibration, 1.5 ml/min flow rate
UV: 210 nm-450 nm DAD
Temperature: 50° C.
Basic 6 Minute LCMS
Mobile phase A: 0.1% ammonium hydroxide in water
Mobile phase B: 0.1% ammonium hydroxide in acetonitrile
Column: C18 phase Fortis 50×4.6 mm with 5 micron particle size
Gradient: 95-5% A over 3 min, 1 min hold, 2 min re-equilibration, 1 ml/min flow rate
UV: 210 nm-450 nm DAD
Temperature: 50° C.
Acidic 30 Minute LCMS
Mobile phase A: 0.1% formic acid in water
Mobile phase B: 0.1% formic acid in acetonitrile
Column: Phenomenex C18 phase Gemini 150×4.6 mm with 5 micron particle size
Gradient: 98-2% A over 18 min, 2 min hold, 1 ml/min flow rate
UV: 210 nm-450 nm DAD
Temperature: 50° C.
Basic 30 Minute LCMS
Mobile phase A: 10 mM ammonium acetate in water
Mobile phase B: 10 mM ammonium acetate in methanol
Column: Phenomenex Phenyl Hexyl 150×4.6 mm with 5 micron particle size
Gradient: 98-2% A over 18 min, 2 min hold, 1 ml/min flow rate
UV: 210 nm-450 nm DAD
Temperature: 50° C.

EXAMPLE 1

4-[4-Chloro-3-(trifluoromethyl)phenoxy]-N-(cyclopropylsulfonyl)benzamide

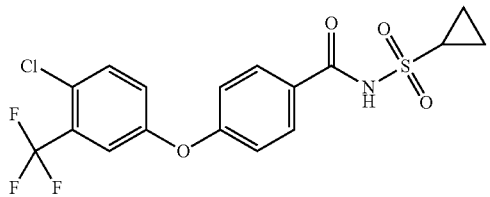 [SMILES: O=C(NS(=O)(=O)C1CC1)c1ccc(Oc2ccc(Cl)c(C(F)(F)F)c2)cc1]

Method A

To a solution of 4-[4-chloro-3-(trifluoromethyl)phenoxy] benzoic acid (Preparation 2, 509 mg, 1.6 mmol) in dichloromethane was added 4-dimethylaminopyridine (589 mg, 4.8 mmol) and 1-ethyl-3-(dimethylaminopropyl)carbodiimide (921 mg, 4.8 mmol). The reaction mixture was stirred at room temperature for 15 minutes. N,N-diisopropylethyl amine (1.2 g, 9.3 mmol) was then added, followed by cyclopropanesulfonamide (584 mg, 4.8 mmol). The reaction mixture was stirred at room temperature overnight. The reaction was quenched by the addition of water and the mixture extracted with ethyl acetate. The organic phase was washed sequentially with a saturated aqueous solution of potassium hydrogen sulphate and brine, dried over anhydrous magnesium sulphate, filtered and concentrated in vacuo. The residue was purified by silica gel column chromatography (20-100% ethyl acetate in heptane elution) to afford the title compound as a clear oil (248 mg, 37%).

$^1$HNMR (CDCl$_3$): δ 1.15 (m, 2H), 1.41 (m, 2H), 3.16 (m, 1H), 7.08 (m, 2H), 7.15 (m, 1H), 7.40 (d, 1H), 7.50 (d, 1H), 7.90 (m, 2H), 8.90 (s, 1H).

LCMS Rt=3.41 minutes MS m/z 420 [MH]+

EXAMPLE 2

5-Chloro-4-(3,4-dichlorophenoxy)-2-fluoro-N-(methylsulfonyl)benzamide

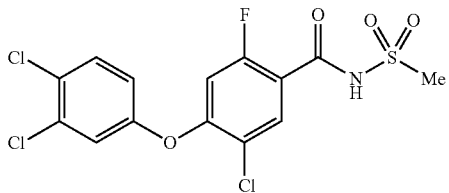 [SMILES: CS(=O)(=O)NC(=O)c1cc(Cl)c(Oc2ccc(Cl)c(Cl)c2)cc1F]

Method B

To an oven dried flask was added sodium hydride (60% dispersion in mineral oil, 22 mg, 0.53 mmol) and anhydrous tetrahydrofuran (10 mL) and the reaction mixture was cooled to 0° C. in an ice bath. Methanesulfonamide (50 mg, 0.53 mmol) was added slowly over 1 minute, then the reaction mixture was warmed to room temperature over 30 minutes. 4-Methyl phenyl 5-chloro-4-(3,4-dichlorophenoxy)-2-fluorobenzoate (Preparation 3, 150 mg, 0.35 mmol) was added and the reaction mixture was heated to 70° C. overnight. The reaction mixture was quenched slowly with iced water and the mixture extracted with ethyl acetate. The organic phase was dried over anhydrous magnesium sulphate, filtered and concentrated in vacuo to give a yellow residue. The residue was purified by silica gel column chromatography (10% methanol in ethyl acetate elution) to afford the title compound as a colourless oil (163 mg, 100%).

¹HNMR (CDCl₃): δ 3.03 (s, 3H), 6.42 (d, 1H), 6.80 (d, 1H), 7.03 (s, 1H), 7.38 (d, 1H), 7.92 (s, 1H).

LCMS Rt=4.21 minutes MS m/z 412 [MH]+

EXAMPLE 3

4-(4-Chloro-2-ethylphenoxy)-2,5-difluoro-N-(methylsulfonyl)benzamide

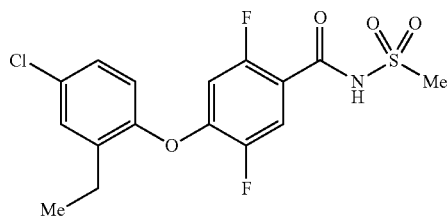 [SMILES: CCc1cc(Cl)ccc1Oc1cc(F)c(C(=O)NS(C)(=O)=O)cc1F]

Method C

4-Chloro-2-ethylphenol (Preparation 6, 104 mg, 0.66 mmol), 2,4,5-trifluoro-N-(methylsulfonyl)benzamide (Preparation 7, 140 mg, 0.55 mmol) and potassium carbonate (228 mg, 1.66 mmol) were stirred in dimethylsulfoxide (5 mL) at 90° C. overnight. The crude reaction mixture was purified by reverse phase column chromatography (Trilution method) to afford the title compound (35 mg, 16%).

¹HNMR (d₆-DMSO): δ 1.10 (m, 3H), 2.60 (m, 2H), 3.30 (s, 3H), 6.90 (m, 1H), 7.00 (m, 1H), 7.30 (m, 1H), 7.45 (m, 1H), 7.80 (m, 1H).

LCMS Rt=4.03 minutes MS m/z 388 [M-H]

EXAMPLE 4

4-(3,4-Dichlorophenoxy)-3-ethyl-N-(methylsulfonyl)benzamide

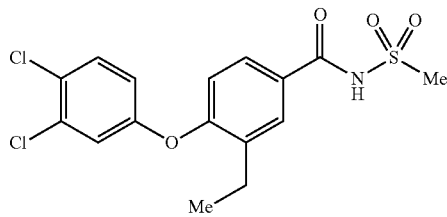 [SMILES: CCc1cc(C(=O)NS(C)(=O)=O)ccc1Oc1ccc(Cl)c(Cl)c1]

Method D 4-(3,4-Dichlorophenoxy)-3-ethylbenzoic acid (Preparation 9, 75 mg, 0.24 mmol), methanesulphonamide (91.7 mmol, 0.96 mmol) and 2-(1H-7-azabenzotriazol-1-yl)-1,1,3,3-tetramethyl uronium hexafluorophosphate (110 mg, 0.29 mmol) were dissolved in anhydrous N,N-dimethylformamide. N,N-diisopropylethylamine (0.21 mL, 1.2 mmol) was added and the reaction mixture was stirred at room temperature for 48 hours. A 1M aqueous solution of hydrogen chloride was added and the mixture extracted with ethyl acetate. The combined organic phase was concentrated in vacuo. The residue was purified initially by reverse phase column chromatography (Trilution method) followed by silica gel column chromatography (40%-100% ethyl acetate in heptane) to afford the title compound (15 mg, 16%).

¹HNMR (CDCl₃): δ 1.23 (m, 3H), 2.70 (m, 2H), 3.40 (s, 3H), 6.92 (m, 2H), 7.09 (m, 1H), 7.40 (m, 1H), 7.65 (m, 1H), 7.80 (m, 1H).

LCMS Rt=3.63 minutes MS m/z 388 [MH]+, 386 [M-H]−

EXAMPLE 5

5-chloro-4-(3-ethoxyphenoxy)-2-fluoro-N-(methylsulfonyl)benzamide

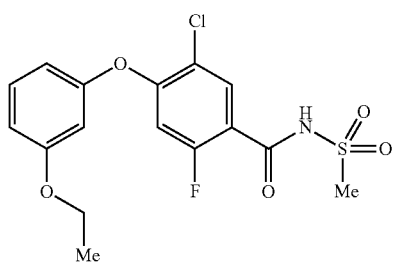 [SMILES: CCOc1cccc(Oc2cc(F)c(C(=O)NS(C)(=O)=O)cc2Cl)c1]

To solution of methyl 5-chloro-2,4-difluorobenzoate (25.9 mg, 0.125 mmol) and 3-ethoxyphenol (17.3 mg, 0.125 mmol) in dimethyl formamide (0.5 mL) was added cesium carbonate (82 mg, 0.25 mmol), the mixture was shaken at 120° C. for 16 hours, filtered and evaporated in vacuo. Water (1 mL) was added and extracted with ethyl acetate (3×1 mL), the combined organic layers were dried over sodium sulphate, filtered and evaporated in vacuo. The residue was dissolved in THF (0.7 mL) and to this solution was added a 1M aqueous solution of lithium hydroxide (0.7 mL) and the mixture was shaken at 30° C. for 16 hours. The reaction mixture was evaporated in vacuo, a 1M aqueous solution of hydrochloric acid (0.7 mL) was added and extracted with ethyl acetate (3×1 mL). The combined organic layers were dried over anhydrous sodium sulphate, filtered and evaporated in vacuo. To this residue was added methanesulfonamide (28.6 mg, 0.300 mmol) and a solution of 4-dimethylaminopyridine (24.4 mg, 0.200 mmol) and EDCl (38.3 mg, 0.200 mmol) in dichloromethane (1 mL), the solution was shaken at 30° C. for 16 hours and evaporated in vacuo. The crude product was purified on a HPLC column (Sepax BR-C18 100*21.2 mm*5 μm, acetonitrile-water (0.1% trifluoroacetic acid) gradient to yield 6.2 mg (16 μmol) 5-chloro-4-(3-ethoxyphenoxy)-2-fluoro-N-(methylsulfonyl)benzamide.

MS m/z=388 [MH]+LCMS Rt=3.220 minutes

| Column | Welch XB-C18 2.1 × 50 mm 5 μm |
|---|---|
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 10% B |
| Time 0.00 min | 10% B |
| Time 0.50 min | 10% B |

EXAMPLE 6

3-chloro-N-(methylsulfonyl)-4-(2-naphthyloxy)benzamide

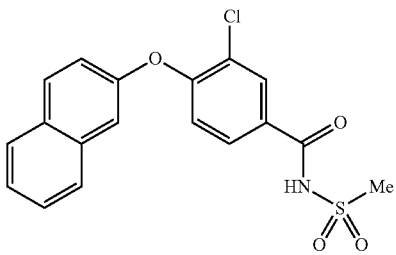 [SMILES: CS(=O)(=O)NC(=O)c1ccc(Oc2ccc3ccccc3c2)c(Cl)c1]

This compound was synthesised according to Example 5 using methyl 3-chloro-4-fluorobenzoate (23.6 mg, 0.125 mmol) and 18.0 mg (0.125 mmol) 2-naphthol (18.0 mg, 0.125 mmol), purified on a HPLC column (Grace Vydac C18 200*20 mm*5 μm, acetonitrile-water (0.1% trifluoroacetic acid) gradient) to yield 6.01 mg (16.0 μmol) of the title compound.

MS m/z=376 [MH]+ LCMS Rt=2.794 minutes

| Column | Welch XB-C18 2.1 × 50 mm 5 μm |
|---|---|
| Temperature | 50° C. |
| Mobile Phase A | 0.0375% TFA in water |
| Mobile Phase B | 0.01875% TFA in acetonitrile |
| Gradient - Initial | 25% B |
| Time 0.00 mins | 25% B |
| Time 0.50 mins | 25% B |
| Time 3.50 mins | 100% B |
| Time 4.00 mins | 25% B |
| Time 4.70 mins | 25% B |
| Flow rate | 0.8 ml/min |
| Injection volume | 2 μl |
| Agilent 1200 HPLC/1956 MSD/SEDEX 75 ELSD | |
| Ionization Mode | API-ES |
| Polarity | Positive |

EXAMPLE 7

5-chloro-4-[3-chloro-4-(trifluoromethoxy)phenoxy]-2-fluoro-N-(methylsulfonyl)benzamide

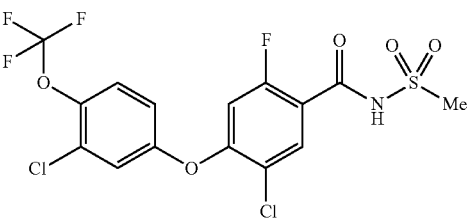 [SMILES: CS(=O)(=O)NC(=O)c1cc(Cl)c(Oc2ccc(OC(F)(F)F)c(Cl)c2)cc1F]

Method E

To a solution of methanesulfonamide (27 mg, 0.283 mmol) in tetrahydrofuran (1.7 mL) was added potassium tert-butoxide and the mixture stirred under nitrogen for 20 minutes. 4-Methylphenyl 5-chloro-4-[3-chloro-4-(trifluoromethoxy)phenoxy]-2-fluorobenzoate (Preparation 167, 106 mg, 0.223 mmol) was then added and the reaction heated to 55° C. for 18 hours. The reaction was quenched by the addition of 10% citric acid (aq) (2 mL) and ethyl acetate (4 mL). The layers were separated, the organic layer was washed with brine (2 ml), dried over magnesium sulfate and concentrated in vacuo to afford a white solid which was purified using silica gel column chromatography eluting with ethyl acetate:heptane 80:20 followed by preparative HPLC to furnish the title compound.

$^1$HNMR (CDCl$_3$): δ 3.43 (s, 3H), 6.70 (m, 1H), 7.02 (m, 1H), 7.28 (m, 1H), 7.41 (m, 1H), 8.25 (m, 1H).

LCMS Rt=3.68 minutes MS m/z 462 [MH]+

The compound of Example 7 can also be prepared according to the following procedure:

5-Chloro-4-[3-chloro-4-(trifluoromethoxy)phenoxy]-2-fluorobenzoic acid (Preparation 162, 29.6 g, 0.0769 mol) and methanesulfonamide (13.5 g, 0.142 mol) were dissolved in tetrahydrofuran (150 mL). Then N-ethyl-N-isopropylpropan-2-amine (41 mL, 0.230 mol) and 2,4,6-tripropyl-1,3,5,2,4,6-trioxatriphosphinane 2,4,6-trioxide in ethyl acetate (120 mL, 0.230 mol) were added and the mixture stirred at reflux for 18 hours. After cooling the reaction mixture to room temperature, the solution was concentrated in vacuo and the residue suspended in water (150 mL), then extracted with ethyl acetate (150 mL). The organic layer was separated and washed with water (2×150 mL). The organic layer was collected, dried over sodium sulfate, filtered and concentrated in vacuo to give a beige solid. The solid was taken in isopropanol (100 mL), heated to 50° C. and stirred until all the compound was in solution. The reaction mixture was cooled down to room temperature and the solid obtained was collected by filtration. The title compound was isolated as a pale yellow solid (22.30 g, 63%).

LC Rt=6.674 minutes $^1$H NMR (400 MHz; CDCl$_3$): δ 3.46 (s, 3H), 6.72 (d, 1H), 7.04 (dd, 1H), 7.24 (d, 1H), 7.42 (d, 1H), 8.27 (d, 1H), 8.69 (br s, 1H)

EXAMPLE 8

4-[4-chloro-3-(trifluoromethyl)phenoxy]-2-fluoro-5-methyl-N-(methylsulfonyl)benzamide

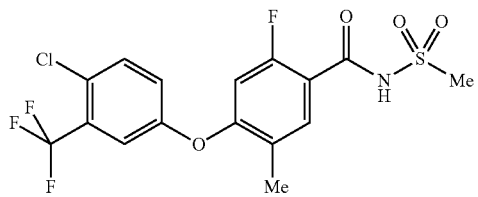 [SMILES: Cc1cc(C(=O)NS(C)(=O)=O)c(F)cc1Oc1ccc(Cl)c(C(F)(F)F)c1]

Method F

To a solution of 4-[4-chloro-3-(trifluoromethyl)phenoxy]-2-fluoro-5-methylbenzaldehyde (Preparation 14, 98 mg, 0.304 mmol) in iso-propyl acetate (2.5 mL) was added methanesulfonamide (29 mg, 0.304 mmol) and bis(tert-butylcarbonyloxy)iodobenzene (124 mg, 0.304 mmol). The mixture was stirred for 5 minutes before the addition of bis[rhodium (alpha, alpha, alpha, alpha'-tetramethyl-1,3-benzenedipropionic acid)] (12 mg, 0.015 mmol). The reaction was stirred at room temperature for 18 hours. The reaction mixture was diluted with ethylacetate (40 mL) and washed with water (2×40 mL) and brine (40 mL) before drying over magnesium sulfate and concentrating in vacuo to afford a crude oil. This was purified using reverse phase column chromatography eluting with acetonitrile:water (plus 0.1% aqueous formic acid) 5:95 to 100:0 followed by recrystallisation of the residue in a mixture of tert-butylmethylether:Heptane 1:3 to furnish 33 mg of the title compound (26%).

$^1$HNMR (CDCl$_3$): δ 2.35 (s, 3H), 3.40 (s, 3H), 6.50 (m, 1H), 7.15 (m, 1H), 7.40 (m, 1H), 7.60 (m, 1H), 8.00 (m, 1H), 8.70 (br s, 1H).

LCMS Rt=3.45 minutes MS m/z 426 [MH]+

EXAMPLE 9

5-chloro-4-(3-chloro-4-(trifluoromethyl)phenoxy)-2-fluoro-N-(methylsulfonyl)benzamide

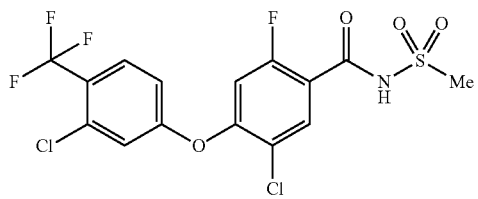 [SMILES: CS(=O)(=O)NC(=O)c1cc(Cl)c(Oc2ccc(C(F)(F)F)c(Cl)c2)cc1F]

To 3-chloro-4-(trifluoromethyl)phenol (Preparation 16, 110 mg, 0.56 mmol) and 5-chloro-2,4-difluoro-N-(methylsulfonyl)benzamide (Preparation 13, 150 mg, 0.56 mmol) dissolved in dimethylsulfoxide (5 ml) was added potassium carbonate (232 mg, 1.68 mmol) and the mixture stirred at 90° C. for 18 hours under nitrogen. The mixture was poured onto ammonium chloride (aq) and extracted with ethyl acetate (3×20 mL), washed with water (3×20 mL) and dried (MgSO$_4$). Purification of the crude product by silica gel column chromatography using 80% Ethyl acetate in heptane furnished the title compound as white solid (12.2 mg, 4.9%).

LCMS Rt=2.87 minutes MS m/z 446 [MH]+

$^1$HNMR (400 MHz, CDCl$_3$): δ 3.30 (s, 3H), 6.58 (m, 1H), 6.79 (m, 1H), 6.95 (m, 1H), 7.58 (m, 1H), 7.93 (m, 1H).

EXAMPLE 10

4-(3,4-dichlorophenoxy)-3-methoxy-N-(methylsulfonyl)benzamide

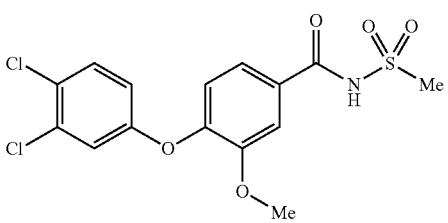 [SMILES: COc1cc(C(=O)NS(C)(=O)=O)ccc1Oc1ccc(Cl)c(Cl)c1]

Method G

To a solution of 4-(3,4-dichlorophenoxy)-3-methoxybenzamide (Preparation 17, 140 mg, 0.448 mmol) in THF (10 mL) was added LiHMDS (1M solution in THF, 0.898 mL, 0.898 mmol) and the mixture stirred for 30 minutes. Methanesulfonyl chloride (103 mg, 0.896 mmol) was then added and the reaction stirred at room temperature for 18 hours. The reaction was partitioned between 1N HCl (aq) and ethyl acetate, the organic layer collected, dried over magnesium sulfate and concentrated in vacuo before purification using reverse phase column chromatography using the Trilution system to afford the title compound as a white powder 94 mg, 54%.

$^1$HNMR (d$_6$-DMSO): δ 3.39 (s, 3H), 3.81 (s, 3H), 6.92 (m, 1H), 7.10 (m, 2H), 7.60 (m, 2H), 7.75 (m, 1H), 12.15 (br s, 1H).

LCMS Rt=3.33 minutes MS m/z 390 [MH]+

EXAMPLE 11

5-chloro-4-[4-chloro-2-(difluoromethoxy)phenoxy]-2-fluoro-N-(methylsulfonyl)benzamide

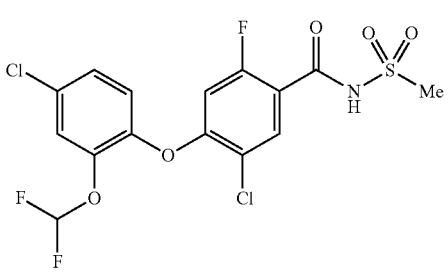 [SMILES: CS(=O)(=O)NC(=O)c1cc(Cl)c(Oc2ccc(Cl)cc2OC(F)F)cc1F]

To a solution of ethyl 5-chloro-4-[4-chloro-2-(difluoromethoxy)phenoxy]-2-fluorobenzoate (Preparation 131, 0.070 g, 0.000177 mol) in tetrahydrofuran (2.50 mL) and water (2.50 mL) was added lithium hydroxide (0.050 g, 0.00209 mol). The reaction mixture was stirred at room temperature under nitrogen for 4 hours. The reaction was diluted with ethyl acetate (10.0 mL) and washed with a saturated aqueous solution of brine (10.0 mL). The organic layer was separated, dried with sodium sulphate, filtered and concentrated in vacuo. The crude was taken up in dichloromethane (5.0 mL) and N-[3-(dimethylamino)propyl]-N'-ethylcarbodiimide hydrochloride (0.051 g, 0.000266 mol), N,N-dimethylpyridin-4-amine (0.049 g, 0.000401) and methanesulfonamide (0.026 g, 0.000273 mol) were added and the mixture was stirred at room temperature under nitrogen for 16 hours. The reaction was diluted in dichloromethane (10.0 mL) and washed twice with an aqueous solution of hydrochloric acid (2M, 15.0 mL). The biphasic system was passed through a separation cartridge to collect the organic layer, which was then concentrated in vacuo. The crude was purified using silica gel column chromatography eluting with 0-100% EtOAc in heptane, 4 g. The compound obtained was then triturated in tert-butyl methyl ether to yield title compound as a pale pink solid (0.020 g, 25% yield).

$^1$H NMR (400 MHz; $d_6$-DMSO): δ 3.20 (s, 3H), 6.90 (m, 1H), 7.15-7.40 (t, 1H), 7.30 (m, 1H), 7.40 (m, 1H), 7.58 (s, 1H), 7.93 (d, 1H), 12.20-12.40 (br s, 1H).

LCMS Rt=1.92 minutes MS m/z 444 [MH]+

EXAMPLE 12

4-[4-chloro-3-(trifluoromethyl)phenoxy]-3,6-difluoro-2-methoxy-N-(methylsulfonyl)benzamide

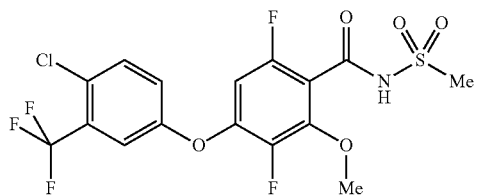 [SMILES: COc1c(F)c(Oc2ccc(Cl)c(C(F)(F)F)c2)cc(F)c1C(=O)NS(C)(=O)=O]

To a solution of 3,4,6-trifluoro-2-methoxybenzaldehyde (Preparation 29, 0.118 g, 0.000280 mol) and potassium carbonate (0.097 g, 0.000702 mol) in dimethyl sulfoxide (3.5 mL) was added 4-chloro-3-(trifluoromethyl)phenol (0.0565 g, 0.000287 mol) portion wise. The reaction mixture was stirred at room temperature under nitrogen for 1 hour. The reaction was diluted with ethyl acetate (15.0 mL) and washed twice with water (10.0 mL). The organic layer was separated, dried with sodium sulphate, filtered and concentrated in vacuo. The residue was dissolved in iso-propyl acetate (3.0 mL) and methanesulfonamide (0.0226 g, 0.000238 mol) and bis(tert-butylcarbonyloxy)iodobenzene (0.145 g, 0.000375 mol) were added The mixture was stirred for 5 minutes before the addition of bis[rhodium(alpha, alpha, alpha', alpha'-tetramethyl-1,3-benzenedipropionic acid)] (0.005 g, 0.00007 mol). The reaction was stirred at 55° C. under nitrogen for 2 hours. The solvent was concentrated in vacuo to afford a crude oil, which was purified using silica gel column chromatography eluting with 0-50% EtOAc in heptanes to furnish a solid. This was further triturated in heptane:acetone (9:1 mixture, 10.0 mL) to yield the title compound as a pale orange solid (0.025 g, 19%).

$^1$H NMR (400 MHz; CDCl$_3$): δ 3.42 (s, 3H), 4.14 (d, 3H), 6.48-6.52 (m, 1H), 7.16-7.19 (m, 1H), 7.40-7.41 (m, 1H), 7.54-7.56 (m, 1H), 8.89 (s, 1H)

LCMS Rt=1.60 minutes MS m/z 460 [MH]+

EXAMPLE 13

4-[3-chloro-4-(difluoromethoxy)phenoxy]-2,5-difluoro-N-(methylsulfonyl)benzamide

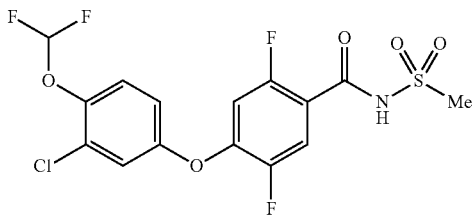 [SMILES: CS(=O)(=O)NC(=O)c1cc(F)c(Oc2ccc(OC(F)F)c(Cl)c2)cc1F]

Method H

To a solution of methanesulfonamide (47 mg, 0.501 mmol) in acetonitrile (2 mL) was added 2,3,4,6,7,8,9,10-octahydropyrimido[1,2-a]azepine (75 μl, 0.501 mmol) and the mixture stirred under nitrogen for 5 minutes. 4-methylphenyl 4-[3-chloro-4-(difluoromethoxy)phenoxy]-2,5-difluorobenzoate (Preparation 72, 148 mg, 0.336 mmol) was then added and the reaction heated to 45° C. for 4 hours. The reaction was concentrated in vacuo and the crude diluted in dichloromethane and washed twice with an aqueous solution of 10% citric acid. The organic layer was washed twice with water and collected, dried over magnesium sulfate and concentrated in vacuo to afford a white solid, which was triturated with a 9:1 mixture of heptane:acetone to afford 122 mg, 72% of the title compound.

$^1$H NMR (400 MHz; $d_6$-DMSO): δ 3.37 (s, 3H), 7.06-7.51 (t, 1H), 7.15-7.25 (m, 2H), 7.40-7.55 (m, 2H), 7.80 (d, 1H).

LCMS Rt=1.41 minutes

MS m/z 428 [MH]+, 426 [MH]−,

EXAMPLE 14

4-(4-chloro-3-(trifluoromethyl)phenoxy)-2-fluoro-N-(methylsulfonyl)benzamide

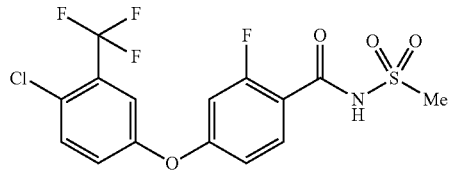 [SMILES: CS(=O)(=O)NC(=O)c1ccc(Oc2ccc(Cl)c(C(F)(F)F)c2)cc1F]

A solution of 4-(4-chloro-3-(trifluoromethyl)phenoxy)-2-fluorobenzoic acid (Preparation 44, 400 mg, 1.19 mmol), DMAP (365 mg, 2.97 mmol, 2.5 eq), diisopropylethylamine (0.7 mL, 2.97 mmol) and EDCl (700 mg, 2.97 mmol) in dichloromethane (10 mL) was allowed to stir for 10 minutes at room temperature under nitrogen. Methane sulphonamide (400 mg, 3.57 mmol) was added in one portion and the reaction mixture left to stir for 16 hours. The reaction was quenched with 6N HCl (20 mL) and the organic layer removed. The DCM layer was extracted into 1N NaOH (30 mL) and the organic layer discarded. The aqueous phase was adjusted to pH 5 using acetic acid and extracted into ethyl acetate (2×30 mL). The organic layer was dried (MgSO₄), filtered and evaporated to give the title compound as a white solid (168 mg, 34%).

¹H NMR (400 MHz, CDCl₃) δ 3.35 (3H, s), 6.70 (1H, m), 6.83 (1H, m), 7.16 (1H, m), 7.38 (1H, m), 7.50 (1H, m), 8.05 (1H, m)

LCMS Rt=3.36 minutes MS m/z 410 [M-H]−

EXAMPLE 15

4-[4-chloro-3-(trifluoromethyl)phenoxy]-N-(methylsulfonyl)benzamide

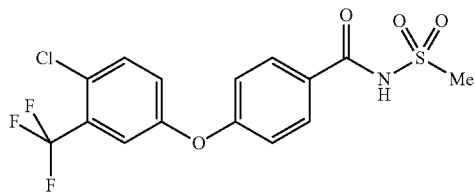 [SMILES: CS(=O)(=O)NC(=O)c1ccc(Oc2ccc(Cl)c(C(F)(F)F)c2)cc1]

To a solution of 4-[4-chloro-3-(trifluoromethyl)phenoxy]benzamide (Preparation 46, 38 g, 120 mmol) in anhydrous THF (200 ml) was added 1.0M lithium 1,1,1,3,3,3-hexamethyldisilazan-2-ide solution in THF (301 ml, 301 mmol) at room temperature via syringe. After 30 minutes stirring, methanesulfonyl chloride (34.5 g, 301 mmol) was added to the reaction mixture, and the resulting mixture was stirred for 18 hours at room temperature. The reaction was quenched by addition of saturated aqueous NH₄Cl solution. The solvent was reduced in vacuo and the residue was diluted with EtOAc (100 ml) and water (100 ml). The aqueous phase was acidified with 2N aqueous HCl solution and extracted with EtOAc (3×50 ml). The combined organic phase was dried over MgSO₄, filtered, and concentrated in vacuo to give an orange solid. The solid was purified by reverse phase column chromatography eluting with acetonitrile:water (plus 0.1% aqueous formic acid) 5:95 to 100:0. The purified material was partitioned between EtOAc (100 ml) and pH2 aqueous HCl solution. The combined organic phase was washed dried over MgSO₄, filtered, and concentrated in vacuo to give 32 g of product as a white solid. The solid was recrystallised in IPA to give 24.9 g of the title compound.

¹H NMR (400 MHz; d₆-DMSO): δ 3.37 (s, 3H), 7.16-7.22 (m, 2H), 7.44 (m, 1H), 7.59 (m, 1H), 7.79 (m, 1H), 7.99-8.04 (m, 2H).

LCMS Rt=3.26 minutes MS m/z 392 [M-H]−.

EXAMPLE 16

5-chloro-4-[4-chloro-3-(trifluoromethyl)phenoxy]-2-fluoro-N-(methylsulfonyl)benzamide

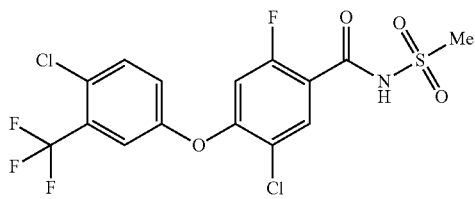 [SMILES: CS(=O)(=O)NC(=O)c1cc(Cl)c(Oc2ccc(Cl)c(C(F)(F)F)c2)cc1F]

To a stirred solution of 5-chloro-4-(4-chloro-3-(trifluoromethyl)phenoxy)-2-fluorobenzoic acid (Preparation 32, 219 mg, 0.58 mmol) in DCM (3 mL) were added EDCl (167 mg, 0.87 mmol) and DMAP (106 mg, 0.87 mmol) and the reaction stirred at room temperature for 30 minutes. Methanesulfonamide (83 mg, 0.87 mmol) was added and the stirring continued at room temperature for 16 hours. DCM (25 mL) and 2M aq. HCl (5 mL) were added and the two layers separated. The organic extract was washed with 2M aq. HCl (5 mL) and brine (10 mL), dried (MgSO₄), filtered and the solvent removed in vacuo. The crude material was purified by silica gel column chromatography eluting with EtOAc:heptane:AcOH (50:50:0.5), followed by recrystallisation from hot IPA to yield the title compound (89 mg, 34%) as a white solid.

¹H NMR (CDCl₃, 400 MHz): δ 3.44 (s, 3H), 6.66 (m, 1H), 7.20 (m, 1H), 7.44 (m, 1H), 7.58 (m, 1H), 8.24 (m, 1H) and 8.72 (br s, 1H).

LCMS Rt=3.23 minutes MS m/z 444 [M-H]−

The compound of Example 16 can also be prepared according to the following procedure:

To a suspension of sodium hydride (7.39 g, 184.66 mmol) in 2-methyltetrahydrofuran (400 mL) at 0-5° C. was added methanesulphonamide (16.47 g, 173.12 mmol) and the mixture stirred for 1 hour and allowed to reach room temperature. 4-Methylphenyl 5-chloro-4-[4-chloro-3-(trifluoromethyl)phenoxy]-2-fluorobenzoate (Preparation 163, 53 g, 115.41 mmol) in 2-methyltetrahydrofuran (100 mL) was added and the reaction mixture heated at 65° C. for 6 hours and cooled. Water (250 mL) was charged to the stirred reaction mixture and the layers separated. The organic layer was further washed with 1M citric acid solution (200 mL) and concentrated under reduced pressure at 45° C. The resulting solid was stirred in tert butyl methyl ether (250 mL) at 50° C. for 1 hour, cooled to 0-5° C., filtered and dried to give the title compound as an off-white solid (27.5 g, 53%).

HPLC Rt=6.574 minutes

¹H NMR (400 MHz, CDCl₃): δ 3.46 (s, 3H), 6.68 (d, 7H), 7.22 (dd, 1H), 7.45 (d, 1H), 7.62 (d, 1H), 8.28 (d, 1H), 8.70 (d, 1H).

EXAMPLE 17

5-chloro-4-[4-chloro-3-(trifluoromethoxy)phenoxy]-2-fluoro-N-(methylsulfonyl)benzamide

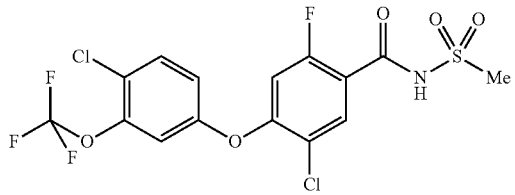 [SMILES: CS(=O)(=O)NC(=O)c1cc(Cl)c(Oc2ccc(Cl)c(OC(F)(F)F)c2)cc1F]

Prepared according to Method E for Example 7 using 4-methylphenyl-5-chloro-4-[4-chloro-3-(trifluoromethoxy)phenoxy]-2-fluorobenzoate (Preparation 147). Purified by trituration in heptane to furnish the title compound.

LCMS Rt=1.74 minutes MS m/z 461 [MH]+

¹HNMR (d₆-DMSO): δ 3.35 (s, 3H), 7.0 (m, 1H), 7.05 (m, 1H), 7.20 (m, 1H), 7.60 (m, 1H), 7.95 (m, 1H).

The following examples were prepared by Method D as described for Example 4 above, using the appropriate Preparations and conditions. Unless otherwise noted, preparation details are as described for the method referred to.

| Ex | Name | Data |
|---|---|---|
| 18 | 5-chloro-4-(2-ethyl-4-fluorophenoxy)-2-fluoro-N-(methylsulfonyl)benzamide | $^1$H NMR (400 MHz; $d_6$-DMSO): δ 1.10 (m, 3H), 2.50 (m, 2H), 3.37 (s, 3H), 6.63 (m, 1H), 7.15 (m, 2H), 7.27 (m, 1H), 7.93 (m, 1H), 12.20 (br s, 1H). |
| 19 | 4-(2-ethyl-4-fluorophenoxy)-2-fluoro-N-(methylsulfonyl)benzamide | $^1$H NMR (400 MHz; $d_6$-DMSO): δ 1.10 (m, 3H), 2.48 (m, 2H), 3.33 (s, 3H), 6.70 (m, 1H), 6.78 (m, 1H), 7.12 (m, 2H), 7.23 (m, 1H), 7.83 (m, 1H), 13.00 (br s, 1H) |
| 20 | 4-(2-ethyl-4-fluorophenoxy)-3-fluoro-N-(methylsulfonyl)benzamide | $^1$H NMR (400 MHz; $d_6$-DMSO): δ 1.10 (m, 3H), 2.50 (m, 2H), 3.38 (s, 3H), 6.83 (m, 1H), 7.10 (m, 2H), 7.15 (m, 1H), 7.75 (m, 1H), 7.98 (m, 1H) |
| 21 | 4-(3,4-dichlorophenoxy)-2,5-difluoro-N-(methylsulfonyl)benzamide | $^1$H NMR (400 MHz; $d^6$-DMSO): δ 3.38 (s, 3H), 7.15 (m, 1H), 7.30 (m, 1H), 7.50 (m, 1H), 7.65 (m, 1H), 7.78 (m, 1H), 12.20 (br s, 1H) |
| 22 | 3-cyano-4-(2-ethyl-4-fluorophenoxy)-N-(methylsulfonyl)benzamide | $^1$H NMR (400 MHz; $CD_3OD$): δ 1.15-1.21 (m, 3H), 2.50-2.60 (m, 2H), 3.17 (s, 3H), 6.70-6.77 (m, 1H), 6.99-7.18 (m, 3H), 8.09-8.16 (m, 1H), 8.37 (s, 1H). |
| 23 | 4-(4-chlorophenoxy)-N-(ethylsulfonyl)benzamide | LCMS Rt = 2.11 minutes MS m/z 340 [MH]+ |
| 24 | 4-(4-chlorophenoxy)-N-(methylsulfonyl)benzamide | LCMS Rt = 2.06 minutes MS m/z 326 [MH]+ |
| 25 | 4-(3,4-dicyanophenoxy)-N-(methylsulfonyl)benzamide | LCMS Rt = 2.45 minutes MS m/z 342 [MH]+ |
| 26 | 4-(4-chlorophenoxy)-N-(cyclopropylsulfonyl)benzamide | LCMS Rt = 2.83 minutes MS m/z 352 [MH]$^+$ |
| 27 | 4-(3,4-dichlorophenoxy)-N-(methylsulfonyl)-3-(trifluoromethyl)benzamide | LCMS Rt = 1.88 minutes MS m/z 426 [M − H]− |
| 28 | 4-(3,4-dichlorophenoxy)-2-fluoro-N-(methylsulfonyl)benzamide | $^1$H NMR (400 MHz; $CD_3OD$): δ 3.00 (s, 3H), 6.82-6.89 (m, 2H), 7.04-7.08 (m, 1H), 7.32 (m, 1H), 7.56-7.60 (m, 1H), 7.74-7.82 (m, 1H). |
| 29 | 3-cyano-4-(3,4-dichlorophenoxy)-N-(methylsulfonyl)benzamide | $^1$H NMR (400 MHz; $d_6$-DMSO): δ 3.34 (s, 3H) 7.13 (m, 1H) 7.33 (m, 1H) 7.72 (m, 1H) 7.78 (m, 1H) 8.17 (m, 1H) 8.48 (m, 1H). |
| 30 | N-(methylsulfonyl)-4-[3-(trifluoromethoxy)phenoxy]benzamide | $^1$H NMR (400 MHz; $CDCl_3$): δ 3.44 (s, 3H), 6.94 (m, 1H), 7.00 (m, 1H), 7.03-7.10 (m, 3H), 7.42 (m, 1H), 7.92 (m, 2H), 9.34 (s, 1H). |
| 31 | 4-(4-chloro-3-(trifluoromethyl)phenoxy)-2,6-difluoro-N-(methylsulfonyl)benzamide | $^1$H NMR (400 MHz; $CDCl_3$): δ 3.15 (s, 3H), 6.38 (m, 2H), 7.11 (m, 1H), 7.32 (m, 1H), 7.48 (m, 1H). |
| 32 | 4-(4-chloro-3-(trifluoromethyl)phenoxy)-2,3,6-trifluoro-N-(methylsulfonyl)benzamide | $^1$H NMR (400 MHz; $CDCl_3$): δ 3.02 (s, 3H), 6.32 (m, 1H), 6.95 (m, 1H), 7.21 (m, 1H), 7.37 (d, 1H). |
| 33 | 4-(3-chloro-4-(trifluoromethyl)phenoxy)-2,5-difluoro-N-(methylsulfonyl)benzamide | $^1$H NMR (400 MHz; $d_6$-DMSO): δ 3.35 (s, 3H), 7.20 (m, 1H), 7.45 (m, 1H), 7.52 (m, 1H), 7.80 (m, 1H), 7.89 (m, 1H), 12.35 (br s, 1H). |
| 34 | 4-(3,4-dichlorophenoxy)-3-fluoro-N-(methylsulfonyl)benzamide | LCMS Rt = 2.25 minutes MS m/z 376 [M − H]− |
| 35 | 4-(2-ethyl-4-fluorophenoxy)-N-(methylsulfonyl)benzamide | LCMS Rt = 3.55 minutes MS m/z 336 [MH]− |
| 36 | 4-(4-(1-methyl-3-(trifluoromethyl)-1H-pyrazol-5-yl)phenoxy)-N-(methylsulfonyl)benzamide | LCMS Rt = 3.61 minutes MS m/z 438 [MH]− |

The following examples were prepared by Method A as described for Example 1 above, using the appropriate Preparations and conditions.

| Ex | Name | Data |
|---|---|---|
| 37 | 4-(4-(1H-imidazol-1-yl)phenoxy)-N-(methylsulfonyl)benzamide | LCMS Rt = 1.88 minutes MS m/z 356 [M − H]− |
| 38 | 4-(2,4-dichlorophenoxy)-N-(methylsulfonyl)benzamide | LCMS Rt = 3.31 minutes MS m/z 360 [MH]+ |

| Ex | Name | Data |
|---|---|---|
| 39 | 4-[4-chloro-2-(trifluoromethoxy)phenoxy]-2-methoxy-N-(methylsulfonyl)benzamide | $^1$HNMR (400 MHz, CDCl$_3$): δ 3.40 (s, 3H), 4.00 (s, 3H), 6.54 (m, 1H), 6.65 (m, 1H), 7.11 (m, 1H), 7.33 (m, 1H), 7.39-7.43 (m, 1H), 8.15 (m, 1H), 10.02 (s, 1H). |
| 40 | 4-(4-chloro-2-methoxyphenoxy)-2-methoxy-N-(methylsulfonyl)benzamide | $^1$HNMR (400 MHz, CDCl$_3$): δ 3.40 (s, 3H), 3.79 (s, 3H), 3.98 (s, 3H), 6.46 (m, 1H), 6.62 (m, 1H), 6.95-7.05 (m, 3H), 8.09 (m, 1H), 10.04 (br s, 1H). |
| 41 | 3-chloro-4-(4-fluorophenoxy)-N-(methylsulfonyl)benzamide | $^1$HNMR (300 MHz, CDCl$_3$): δ 3.40 (s, 3H), 6.8 (m, 1H), 7.12 (m, 4H), 7.62 (m, 1H), 8.0 (m, 1H), 8.60 (br s, 1H). |
| 42 | 4-[4-chloro-3-(trifluoromethyl)phenoxy]-3-fluoro-N-(methylsulfonyl)benzamide | LCMS Rt = 3.56 minutes MS m/z 412 [MH]+, 410 [MH]− |
| 43 | 2-chloro-4-[4-chloro-3-(trifluoromethyl)phenoxy]-N-(methylsulfonyl)benzamide | LCMS Rt = 3.42 minutes MS m/z 428 [MH]+, 426 [M H]−. |
| 44 | 3-chloro-4-[4-chloro-3-(trifluoromethyl)phenoxy]-N-(methylsulfonyl)benzamide | $^1$H NMR (400 MHz; CDCl$_3$): δ 3.46 (s, 3 H) 7.02 (m, 1H) 7.13 (m, 1H) 7.37 (m, 1H) 7.54 (m, 1H) 7.74 (m, 1H) 8.04 (m, 1H). |
| 45 | 4-(4-chloro-3-(trifluoromethyl)phenoxy)-3,5-difluoro-N-(methylsulfonyl)benzamide | $^1$H NMR (400 MHz; CDCl$_3$): δ 3.39 (s, 3H), 7.18-7.23 (m, 1H), 7.43 (m, 1H), 7.61 (m, 1H), 7.72-7.81 (m, 2H). |
| 46 | 4-(4-chloro-3-(trifluoromethyl)phenoxy)-2,3-difluoro-N-(methylsulfonyl)benzamide | $^1$H NMR (400 MHz; CDCl$_3$): δ 3.43 (s, 3H), 6.90 (m, 1H), 7.20 (m, 1H), 7.43 (m, 1H), 7.57 (m, 1H), 7.90 (m, 1H). |
| 47 | 4-(4-chloro-2-methoxyphenoxy)-2,5-difluoro-N-(methylsulfonyl)benzamide | $^1$H NMR (400 MHz, CDCl$_3$): δ 3.42 (s, 3H), 3.79 (s, 3H), 6.41-6.47 (m, 1H), 6.99-7.09 (m, 3H), 7.87-7.93 (m, 1H) |

The following examples were prepared by Method E, as described for Example 7 above using methanesulfonamide, and the appropriate Preparations and conditions.

| Ex | Name | Data |
|---|---|---|
| 48 | 5-chloro-4-[4-chloro-3-(difluoromethoxy)phenoxy]-2-fluoro-N-(methylsulfonyl)benzamide | 1H NMR (400 MHz; d$_6$-DMSO): δ 3.34 (s, 3 H), 7.01 (m, 1H), 7.17 (m, 1H), 7.16-7.53 (t, 1H), 7.25 (m, 1H), 7.67 (m, 1H), 7.97 (m, 1H). |
| 49 | 4-[4-chloro-3-(difluoromethoxy)phenoxy]-2,5-difluoro-N-(methylsulfonyl)benzamide | 1H NMR (400 MHz; d$_6$-DMSO): δ 3.32 (s, 3H), 7.04 (m, 1H), 7.13-7.53 (t, 1H), 7.22-7.29 (m, 2H), 7.66 (m, 1H), 7.79 (m, 1H). |
| 50 | N-(methylsulfonyl)-4-(2-(pyridazin-4-yl)-4-(trifluoromethyl)phenoxy)benzamide | LCMS Rt = 3.22 minutes MS m/z 438 [MH]+ |

The following example was prepared by Method H, as described for Example 13 above using methanesulfonamide, and the appropriate Preparations and conditions.

| Ex | Name | Data |
|---|---|---|
| 51 | 5-chloro-4-[3-chloro-4-(difluoromethoxy)phenoxy]-2-fluoro-N-(methylsulfonyl)benzamide | 1H NMR (400 MHz; d$_6$-DMSO): δ 3.37 (s, 3H), 7.06-7.28 (m, 3H), 7.42-7.49 (m, 2H), 7.97 (m, 1H). |

The following examples were prepared by Method C, as described for Example 3 above, using the appropriate Preparations and conditions.

| Ex | Name | Data |
|---|---|---|
| 52 | 5-chloro-4-(4-chloro-2-methoxyphenoxy)-2-fluoro-N-(methylsulfonyl)benzamide | LCMS Rt = 2.31 minutes MS m/z 408 [MH]+ |
| 53 | 5-chloro-4-[4-chloro-2-(trifluoromethoxy)phenoxy]-2-fluoro-N-(methylsulfonyl)benzamide | LCMS Rt = 2.32 minutes MS m/z 462 [MH]+ |
| 54 | 5-chloro-4-(5-chloro-2-methoxyphenoxy)-2-fluoro-N-(methylsulfonyl)benzamide | LCMS Rt = 2.14 minutes MS m/z 406 [M − H]− |

| Ex | Name | Data |
|---|---|---|
| 55 | 4-(3-chloro-4-(trifluoromethoxy)phenoxy)-2,5-difluoro-N-(methylsulfonyl)benzamide | ¹H NMR (400 MHz; CD₃OD): δ 3.34 (s, 3H), 7.04-7.08 (m, 1H), 7.10-7.14 (m, 1H), 7.34 (d, 1H), 7.49 (dd, 1H), 7.66-7.70 (m, 1H). |
| 56 | 4-(4-chloro-3-(trifluoromethoxy)phenoxy)-2,5-difluoro-N-(methylsulfonyl)benzamide | ¹H NMR (400 MHz; CDCl₃): δ 3.43 (s, 3H), 6.77 (m, 1H), 6.97 (m, 1H), 7.09 (m, 1H), 7.52 (m, 1H), 7.96 (m, 1H). |
| 57 | 4-[4-chloro-3-(trifluoromethyl)phenoxy]-2,5-difluoro-N-(phenylsulfonyl)benzamide | ¹HNMR (d₆-DMSO): δ 7.30 (m, 1H), 7.40 (m, 1H), 7.60 (dd, 3H), 7.75 (m, 3H), 7.41 (m, 2H). |
| 58 | N-(sec-butylsulfonyl)-4-[4-chloro-3-(trifluoromethyl)phenoxy]-2,5-difluorobenzamide | LCMS Rt = 3.94 minutes. MS m/z 470 [M − H]−, |

The following were prepared by Method F, as described for Example 8 above, using the appropriate Preparations and conditions.

| Ex | Name | Data |
|---|---|---|
| 59 | 4-[4-chloro-3-(trifluoromethyl)phenoxy]-3-methoxy-N-(methylsulfonyl)benzamide | ¹H NMR (400 MHz; d₆-DMSO): δ 3.25 (s, 3H), 3.80 (s, 3H), 7.12-7.22 (m, 2H), 7.33 (s, 1H), 7.58-7.68 (m, 2H), 7.75 (s, 1H). |
| 60 | 4-[4-chloro-3-(trifluoromethyl)phenoxy]-5-fluoro-2-methoxy-N-(methylsulfonyl)benzamide | ¹H NMR (400 MHz; d₆-DMSO): δ 3.15 (s, 3H), 3.83 (s, 3H), 7.06-7.08 (m, 1H), 7.16-7.19 (m, 1H), 7.37-7.38 (m, 1H), 7.61-7.64 (m, 1H), 7.66-7.69 (m, 1H), 12.03 (br s, 1H). |
| 61 | 4-(4-chloro-2-methoxyphenoxy)-5-fluoro-2-methoxy-N-(methylsulfonyl)benzamide | ¹H NMR (400 MHz; d₆-DMSO): δ 3.23 (s, 3H), 3.74 (s, 3H), 3.80 (s, 3H), 6.58-6.60 (m, 1H), 6.98-7.03 (m, 2H), 7.24 (m, 1H), 7.54-7.57 (m, 1H), 11.54 (s, 1H) |
| 62 | 4-[4-chloro-3-(trifluoromethyl)phenoxy]-3-cyano-N-(methylsulfonyl)benzamide | LCMS Rt = 2.49 minutes MS m/z 419 [MH]+ 417 [M − H]− |
| 63 | 4-(4-chloro-2-methoxyphenoxy)-3-cyano-N-(methylsulfonyl)benzamide | ¹H NMR (400 MHz; d₆-DMSO): δ 3.36 (s, 3H), 3.77 (s, 3H), 6.81-6.83 (m, 1H), 7.13-7.16 (m, 1H), 7.36-7.38 (m, 2H), 8.09-8.11 (m, 1H), 8.45 (d, 1H), 12.20 (bs, 1H). |
| 64 | 4-(4-chloro-2-methoxyphenoxy)-2-fluoro-N-(methylsulfonyl)benzamide | ¹H NMR (400 MHz; CDCl₃): δ 3.43 (s, 3H), 3.79 (s, 3H), 6.60-6.64 (m, 1H), 6.81-6.83 (m, 1H), 6.99-7.07 (m, 3H), 8.06 (m, 1H), 8.70-8.74 (m, 1H). |
| 65 | 4-(4-chloro-2-methoxyphenoxy)-3-fluoro-N-(methylsulfonyl)benzamide | ¹H NMR (400 MHz; CDCl₃): δ 3.44 (s, 3H), 3.79 (s, 3H), 6.77 (m, 1H), 6.97-7.05 (m, 3H), 7.48-7.51 (m, 1H), 7.71-7.74 (m, 1H), 8.69 (s, 1H). |

The following were prepared by Method G, as described for Example 10 above, using the appropriate Preparations and conditions.

| Ex | Name | Data |
|---|---|---|
| 66 | 2,5-difluoro-4-(2-methoxy-5-(trifluoromethoxy)phenoxy)-N-(methylsulfonyl)benzamide | ¹H NMR (400 MHz, CDCl₃): δ 3.40 (s, 3H), 3.80 (s, 3H), 6.48 (dd, 1H), 7.00-7.10 (m, 2H), 7.20 (d, 1H), 7.93 (dd, 1H), 8.60-8.80 (br, NH). |
| 67 | 4-(5-chloro-2-methoxyphenoxy)-2,5-difluoro-N-(methylsulfonyl)benzamide | ¹H NMR (400 MHz, CDCl₃): δ 3.42 (s, 3H), 3.79 (s, 3H), 6.48 (dd, 1H), 6.89 (d, 1H), 7.15 (d, 1H), 7.26 (dd, 1H), 7.91 (dd, 1H), 8.68 (br.s, 1H). |

-continued

| Ex | Name | Data |
|---|---|---|
| 68 | 2,5-difluoro-4-(2-methoxy-5-(trifluoromethyl)phenoxy)-N-(methylsulfonyl)benzamide | $^1$H NMR (400 MHz, CDCl$_3$): δ 3.42 (s, 3H), 3.86 (s, 3H), 6.46 (m, 1H), 7.13 (m, 1H), 7.42 (m, 1H), 7.58 (m, 1H), 7.92 (m, 1H), 8.66 (br s, 1H). |
| 69 | 2,5-difluoro-4-(4-fluoro-2-methoxyphenoxy)-N-(methylsulfonyl)benzamide | $^1$H NMR (400 MHz, CDCl$_3$): δ 3.42 (s, 3H), 3.79 (s, 3H), 6.41 (m, 1H), 6.73 (m, 1H), 6.79 (m, 1H), 7.11 (m, 1H), 7.90 (m, 1H), 8.66 (br s, 1H). |
| 70 | 4-(4,5-dichloro-2-methoxyphenoxy)-2,5-difluoro-N-(methylsulfonyl)benzamide | $^1$H NMR (400 MHz, CDCl$_3$): δ 3.55 (s, 3H), 3.75 (s, 3H), 6.44 (m, 1H), 7.06 (m, 1H), 7.20 (m, 1H), 7.86 (m, 1H), 8.55-8.65 (br d, 1H). |
| 71 | 2,5-difluoro-4-(5-fluoro-2-methoxyphenoxy)-N-(methylsulfonyl)benzamide | 1H NMR (400 MHz, CDCl$_3$): δ 3.41 (s, 3H), 3.77 (s, 3H), 6.48 (m, 1H), 6.91 (m, 1H), 7.00 (m, 2H), 7.90 (m, 1H), 8.69 (br d, 1H). |
| 72 | 2,5-difluoro-4-[2-methoxy-4-(trifluoromethoxy)phenoxy]-N-(methylsulfonyl)benzamide | 1H NMR (400 MHz, CDCl$_3$): δ 3.41 (s, 3H), 3.80 (s, 3H), 6.44 (m, 1H), 6.89-6.91 (m, 2H), 7.15 (m, 1H), 7.90 (m, 1H), 8.67 (br d, 1H). |
| 73 | 4-[4-chloro-2-(trifluoromethoxy)phenoxy]-2,5-difluoro-N-(methylsulfonyl)benzamide | LCMS Rt = 3.89 minutes MS m/z 446 [MH]$^+$ |
| 74 | 2,5-difluoro-4-(2-methoxy-4-(trifluoromethyl)phenoxy)-N-(methylsulfonyl)benzamide | 1H NMR (400 MHz, CDCl$_3$): δ 3.42 (s, 3H), 3.86 (s, 3H), 6.49 (m, 1H), 7.22-7.32 (m, 3H), 7.92 (m, 1H). |
| 75 | 4-(4-chloro-3-(trifluoromethyl)phenoxy)-2,5-difluoro-N-(methylsulfonyl)benzamide | $^1$H NMR (400 MHz; d$_6$-DMSO): δ 3.30 (s, 3H), 7.38 (m, 1H), 7.41 (m, 1H), 7.63 (m, 1H), 7.80 (m, 2H). |
| 76 | 4-(4-chloro-3-(trifluoromethyl)phenoxy)-N-(isopropylsulfonyl)benzamide | $^1$H NMR (400 MHz; d$_6$-DMSO): δ 1.22 (m, 6H), 3.72 (m, 1H), 7.08 (m, 2H), 7.35 (m, 1H), 7.50 (m, 1H), 7.68 (m, 1H), 7.90 (m, 2H), 11.85 (br s, 1 H). |
| 77 | 2-chloro-4-(4-chloro-3-(trifluoromethyl)phenoxy)-5-fluoro-N-(methylsulfonyl)benzamide | $^1$H NMR (400 MHz, CDCl$_3$): δ 3.45 (s, 3H), 7.05 (m, 1H), 7.15 (m, 1H), 7.37 (m, 1H), 7.55 (m, 1H), 7.80 (m, 1H) |
| 78 | 4-(4-chloro-3-(trifluoromethyl)phenoxy)-3-fluoro-2-methoxy-N-(methylsulfonyl)benzamide | $^1$H NMR (400 MHz, CDCl$_3$): δ 3.42 (s, 3H), 4.23 (m, 3H), 6.81 (m, 1H), 7.15 (m, 1H), 7.39 (m, 1H), 7.53 (m, 1H), 7.95 (m, 1H), 10.06 (s, 1H). |
| 79 | 4-(4-chloro-3-(trifluoromethyl)phenoxy)-2-methoxy-N-(methylsulfonyl)benzamide | $^1$H NMR (400 MHz; d$_6$-DMSO): δ 3.34 (s, 3H), 3.86 (s, 3H), 6.69 (dd, 1H), 6.96 (d, 1H), 7.41 (dd, 1H), 7.55 (d, 1H), 7.66 (d, 1H), 7.78 (d, 1H), 11.31 (s, 1H). |
| 80 | 5-chloro-4-[4-chloro-2-(1-methyl-1H-pyrazol-5-yl)phenoxy]-2-fluoro-N-(methylsulfonyl)benzamide | 1H NMR (400 MHz; d$_6$-DMSO): δ 3.20 (s, 3H), 3.80 (s, 3H), 6.35 (m, 1H), 6.90 (m, 1H), 7.20 (m, 1H), 7.40 (m, 1H), 7.60 (m, 2H), 7.80 (m, 1H). |
| 81 | 4-(3,4-dichlorophenoxy)-3-methyl-N-(methylsulfonyl)benzamide | 1H NMR (400 MHz; d$_6$-DMSO): δ 2.23 (s, 3H), 3.30 (s, 3H), 7.00 (m, 2H), 7.27 (m, 1H), 7.63 (m, 1H), 7.80 (m, 1H), 7.97 (m, 1H), 12.00 (br s, 1H) |
| 82 | 3-chloro-4-(3,4-dichlorophenoxy)-N-(methylsulfonyl)benzamide | 1H NMR (400 MHz; d$_6$-DMSO): δ 3.30 (s, 3H), 6.98 (m, 1H), 7.12 (m, 1H), 7.30 (m, 1H), 7.62 (m, 1H), 7.88 (m, 1H), 8.05 (m, 1H) |
| 83 | 4-(4-chloro-2-(1-methyl-1H-pyrazol-5-yl)phenoxy)-N-(methylsulfonyl)benzamide | LCMS Rt = 3.19 minutes MS m/z 406 [MH]+ |

The compounds of formula (I) that follow were prepared by the procedures described in the aforementioned Schemes, foregoing Examples and the corresponding preparations, using appropriate reagents and conditions, or by routine variation of those processes.

| Ex | Name | MS m/z |
|---|---|---|
| 84 | 4-[4-chloro-3-(trifluoromethyl)phenoxy]-2,5-difluoro-N-(methylsulfonyl)benzamide | 430 |
| 85 | 2,5-difluoro-4-(2-methoxy-4-methylphenoxy)-N-(methylsulfonyl)benzamide | 372 |

-continued

| Ex | Name | MS m/z |
|---|---|---|
| 86 | 2,5-difluoro-4-(2-methoxy-5-methylphenoxy)-N-(methylsulfonyl)benzamide | 372 |
| 87 | 4-(2,3-dichlorophenoxy)-2,5-difluoro-N-(methylsulfonyl)benzamide | 396 |
| 88 | 4-(5-cyano-2-methoxyphenoxy)-2,5-difluoro-N-(methylsulfonyl)benzamide | 383 |
| 89 | 4-(2,5-difluorophenoxy)-2,5-difluoro-N-(methylsulfonyl)benzamide | 364 |
| 90 | 2,5-difluoro-4-(2-isopropoxyphenoxy)-N-(methylsulfonyl)benzamide | 386 |
| 91 | 4-(2-chloro-6-fluorophenoxy)-2,5-difluoro-N-(methylsulfonyl)benzamide | 380 |
| 92 | 2,5-difluoro-4-(3-fluoro-5-methoxyphenoxy)-N-(methylsulfonyl)benzamide | 376 |
| 93 | 2,5-difluoro-4-(2-isopropylphenoxy)-N-(methylsulfonyl)benzamide | 370 |
| 94 | 2,5-difluoro-N-(methylsulfonyl)-4-(2,4,6-trifluorophenoxy)benzamide | 382 |
| 95 | 4-(3-chloro-4-cyanophenoxy)-2,5-difluoro-N-(methylsulfonyl)benzamide | 387 |
| 96 | 4-(2,6-difluorophenoxy)-2,5-difluoro-N-(methylsulfonyl)benzamide | 364 |
| 97 | 2,5-difluoro-N-(methylsulfonyl)-4-(2,3,5-trifluorophenoxy)benzamide | 382 |
| 98 | 4-(2-ethoxyphenoxy)-2,5-difluoro-N-(methylsulfonyl)benzamide | 372 |
| 99 | 4-(4-chloro-3-methylphenoxy)-2,5-difluoro-N-(methylsulfonyl)benzamide | 376 |
| 100 | 2,5-difluoro-N-(methylsulfonyl)-4-[4-(trifluoromethoxy)phenoxy]benzamide | 412 |
| 101 | 4-(3,5-dichlorophenoxy)-2,5-difluoro-N-(methylsulfonyl)benzamide | 396 |
| 102 | 4-(4-chloro-2-methylphenoxy)-2,5-difluoro-N-(methylsulfonyl)benzamide | 376 |
| 103 | 2,5-difluoro-N-(methylsulfonyl)-4-[2-(trifluoromethoxy)phenoxy]benzamide | 412 |
| 104 | 4-(2,6-dimethylphenoxy)-2,5-difluoro-N-(methylsulfonyl)benzamide | 356 |
| 105 | 4-(2,5-dichlorophenoxy)-2,5-difluoro-N-(methylsulfonyl)benzamide | 396 |
| 106 | 2,5-difluoro-4-(4-methylphenoxy)-N-(methylsulfonyl)benzamide | 342 |
| 107 | 2,5-difluoro-4-(2-fluorophenoxy)-N-(methylsulfonyl)benzamide | 346 |
| 108 | 2,5-difluoro-4-(2-fluoro-6-methoxyphenoxy)-N-(methylsulfonyl)benzamide | 376 |
| 109 | 4-(2-chloro-5-methoxyphenoxy)-2,5-difluoro-N-(methylsulfonyl)benzamide | 392 |
| 110 | 4-(2-chloro-5-methylphenoxy)-2,5-difluoro-N-(methylsulfonyl)benzamide | 376 |
| 111 | 2,5-difluoro-4-(2-methylphenoxy)-N-(methylsulfonyl)benzamide | 342 |
| 112 | 4-(4-cyano-3,5-dimethylphenoxy)-2,5-difluoro-N-(methylsulfonyl)benzamide | 381 |
| 113 | 2,5-difluoro-N-(methylsulfonyl)-4-[2-(trifluoromethyl)phenoxy]benzamide | 396 |
| 114 | 4-(2-ethylphenoxy)-2,5-difluoro-N-(methylsulfonyl)benzamide | 356 |
| 115 | 2,5-difluoro-4-(5-fluoro-2-methylphenoxy)-N-(methylsulfonyl)benzamide | 360 |
| 116 | 4-(2-cyano-4-methoxyphenoxy)-2,5-difluoro-N-(methylsulfonyl)benzamide | 383 |
| 117 | 2,5-difluoro-4-(2-methoxyphenoxy)-N-(methylsulfonyl)benzamide | 358 |
| 118 | 4-(4-ethoxyphenoxy)-2,5-difluoro-N-(methylsulfonyl)benzamide | 372 |
| 119 | 2,5-difluoro-N-(methylsulfonyl)-4-(3,4,5-trifluorophenoxy)benzamide | 380 |
| 120 | 4-(2-chloro-4-fluorophenoxy)-2,5-difluoro-N-(methylsulfonyl)benzamide | 380 |
| 121 | 4-[2-chloro-5-(trifluoromethyl)phenoxy]-2,5-difluoro-N-(methylsulfonyl)benzamide | 430 |
| 122 | 2,5-difluoro-4-(2-fluoro-5-methylphenoxy)-N-(methylsulfonyl)benzamide | 360 |
| 123 | 4-(2,4-dichlorophenoxy)-2,5-difluoro-N-(methylsulfonyl)benzamide | 396 |
| 124 | 2,5-difluoro-N-(methylsulfonyl)-4-[3-(trifluoromethoxy)phenoxy]benzamide | 412 |
| 125 | 4-(3-cyanophenoxy)-2,5-difluoro-N-(methylsulfonyl)benzamide | 353 |
| 126 | 4-(2-cyclopropyl-4-fluorophenoxy)-2,5-difluoro-N-(methylsulfonyl)benzamide | 386 |
| 127 | 4-(2,5-dimethylphenoxy)-2,5-difluoro-N-(methylsulfonyl)benzamide | 356 |
| 128 | 4-(3,5-difluorophenoxy)-2,5-difluoro-N-(methylsulfonyl)benzamide | 364 |
| 129 | 4-(4-chlorophenoxy)-2,5-difluoro-N-(methylsulfonyl)benzamide | 362 |
| 130 | 4-(2-cyano-4-fluorophenoxy)-2,5-difluoro-N-(methylsulfonyl)benzamide | 371 |
| 131 | 2,5-difluoro-4-(4-fluorophenoxy)-N-(methylsulfonyl)benzamide | 346 |
| 132 | 4-(4-cyano-2,6-dimethylphenoxy)-2,5-difluoro-N-(methylsulfonyl)benzamide | 381 |
| 133 | 4-(5-chloro-2-methylphenoxy)-2,5-difluoro-N-(methylsulfonyl)benzamide | 376 |
| 134 | 2,5-difluoro-4-(3-methoxyphenoxy)-N-(methylsulfonyl)benzamide | 358 |
| 135 | 4-(4-cyano-2-methoxyphenoxy)-2,5-difluoro-N-(methylsulfonyl)benzamide | 383 |
| 136 | 4-(3,4-difluorophenoxy)-2,5-difluoro-N-(methylsulfonyl)benzamide | 364 |
| 137 | 2,5-difluoro-4-(4-fluoro-2-methoxy-3-methylphenoxy)-N-(methylsulfonyl)benzamide | 390 |

-continued

| Ex | Name | MS m/z |
|---|---|---|
| 138 | 2,5-difluoro-N-(methylsulfonyl)-4-[3-(trifluoromethyl)phenoxy]benzamide | 396 |
| 139 | 2,5-difluoro-4-(3-methoxy-5-methylphenoxy)-N-(methylsulfonyl)benzamide | 372 |
| 140 | 4-(3,5-dimethylphenoxy)-2,5-difluoro-N-(methylsulfonyl)benzamide | 356 |
| 141 | 4-(3,4-dimethylphenoxy)-2,5-difluoro-N-(methylsulfonyl)benzamide | 356 |
| 142 | 2,5-difluoro-4-(3-fluorophenoxy)-N-(methylsulfonyl)benzamide | 346 |
| 143 | 4-(4-chloro-3-fluorophenoxy)-2,5-difluoro-N-(methylsulfonyl)benzamide | 380 |
| 144 | 4-(3-chloro-5-methoxyphenoxy)-2,5-difluoro-N-(methylsulfonyl)benzamide | 392 |
| 145 | 2,5-difluoro-4-(4-fluoro-3-methylphenoxy)-N-(methylsulfonyl)benzamide | 360 |
| 146 | 4-(2-chloro-4-methoxyphenoxy)-2,5-difluoro-N-(methylsulfonyl)benzamide | 392 |
| 147 | 4-(3-ethylphenoxy)-2,5-difluoro-N-(methylsulfonyl)benzamide | 356 |
| 148 | 4-(2-ethoxy-4-methylphenoxy)-2,5-difluoro-N-(methylsulfonyl)benzamide | 386 |
| 149 | 4-(3-chloro-2-fluorophenoxy)-2,5-difluoro-N-(methylsulfonyl)benzamide | 380 |
| 150 | 2,5-difluoro-4-(4-methoxyphenoxy)-N-(methylsulfonyl)benzamide | 358 |
| 151 | 4-(3-chloro-4-methylphenoxy)-2,5-difluoro-N-(methylsulfonyl)benzamide | 376 |
| 152 | 4-(4-cyanophenoxy)-2,5-difluoro-N-(methylsulfonyl)benzamide | 351 |
| 153 | 4-(3-ethoxyphenoxy)-2,5-difluoro-N-(methylsulfonyl)benzamide | 372 |
| 154 | 2,5-difluoro-4-(4-fluoro-2-methylphenoxy)-N-(methylsulfonyl)benzamide | 360 |
| 155 | 4-(3-chloro-5-methylphenoxy)-2,5-difluoro-N-(methylsulfonyl)benzamide | 376 |
| 156 | 4-(3-chlorophenoxy)-2,5-difluoro-N-(methylsulfonyl)benzamide | 362 |
| 157 | 2,5-difluoro-4-(3-methylphenoxy)-N-(methylsulfonyl)benzamide | 342 |
| 158 | 2,5-difluoro-4-(3-isopropylphenoxy)-N-(methylsulfonyl)benzamide | 370 |
| 159 | 2,5-difluoro-4-(4-isopropylphenoxy)-N-(methylsulfonyl)benzamide | 370 |
| 160 | 4-(3-fluorophenoxy)-N-(methylsulfonyl)benzamide | 310 |
| 161 | 4-(3-methoxyphenoxy)-N-(methylsulfonyl)benzamide | 322 |
| 162 | 4-(2,5-dimethylphenoxy)-N-(methylsulfonyl)benzamide | 320 |
| 163 | N-(methylsulfonyl)-4-[3-(trifluoromethyl)phenoxy]benzamide | 360 |
| 164 | 4-(2-chlorophenoxy)-N-(methylsulfonyl)benzamide | 326 |
| 165 | 4-(3,4-difluorophenoxy)-N-(methylsulfonyl)benzamide | 328 |
| 166 | 4-(2,5-difluorophenoxy)-N-(methylsulfonyl)benzamide | 328 |
| 167 | 4-(3,4-dimethylphenoxy)-N-(methylsulfonyl)benzamide | 320 |
| 168 | N-(methylsulfonyl)-4-[4-(trifluoromethoxy)phenoxy]benzamide | 376 |
| 169 | 4-(2-isopropylphenoxy)-N-(methylsulfonyl)benzamide | 334 |
| 170 | 4-(4-chloro-3-methylphenoxy)-N-(methylsulfonyl)benzamide | 340 |
| 171 | 4-(2-fluorophenoxy)-N-(methylsulfonyl)benzamide | 310 |
| 172 | 4-(2,4-dimethylphenoxy)-N-(methylsulfonyl)benzamide | 320 |
| 173 | 4-(4-isopropylphenoxy)-N-(methylsulfonyl)benzamide | 334 |
| 174 | 4-(3,5-dimethylphenoxy)-N-(methylsulfonyl)benzamide | 320 |
| 175 | 4-(4-chloro-2-methoxyphenoxy)-N-(methylsulfonyl)benzamide | 356 |
| 176 | 4-[2-(benzyloxy)phenoxy]-N-(methylsulfonyl)benzamide | 398 |
| 177 | 4-(5-chloro-2-methylphenoxy)-N-(methylsulfonyl)benzamide | 340 |
| 178 | 4-[4-(benzyloxy)phenoxy]-N-(methylsulfonyl)benzamide | 398 |
| 179 | 4-(5-fluoro-2-methylphenoxy)-N-(methylsulfonyl)benzamide | 324 |
| 180 | 4-(2-chloro-5-methylphenoxy)-N-(methylsulfonyl)benzamide | 340 |
| 181 | 4-(3-isopropylphenoxy)-N-(methylsulfonyl)benzamide | 334 |
| 182 | 4-(3,4-dichlorophenoxy)-N-(methylsulfonyl)benzamide | 360 |
| 183 | 4-(2-chloro-4-methoxyphenoxy)-N-(methylsulfonyl)benzamide | 356 |
| 184 | 4-(2,3-dimethylphenoxy)-N-(methylsulfonyl)benzamide | 320 |
| 185 | 4-(2-methoxy-5-methylphenoxy)-N-(methylsulfonyl)benzamide | 336 |
| 186 | 4-(4-methoxyphenoxy)-N-(methylsulfonyl)benzamide | 322 |
| 187 | 4-(3-chloro-5-methylphenoxy)-N-(methylsulfonyl)benzamide | 340 |
| 188 | 4-(5-fluoro-2-methoxyphenoxy)-N-(methylsulfonyl)benzamide | 340 |
| 189 | 4-(2-methoxy-4-methylphenoxy)-N-(methylsulfonyl)benzamide | 336 |
| 190 | 4-[4-chloro-3-(trifluoromethyl)phenoxy]-N-(methylsulfonyl)benzamide | 394 |
| 191 | 4-(2-methylphenoxy)-N-(methylsulfonyl)benzamide | 306 |
| 192 | 4-(3,5-difluorophenoxy)-N-(methylsulfonyl)benzamide | 328 |
| 193 | 4-(2,6-dimethylphenoxy)-N-(methylsulfonyl)benzamide | 320 |
| 194 | 4-(2-chloro-5-methoxyphenoxy)-N-(methylsulfonyl)benzamide | 356 |
| 195 | 4-(2,3-difluorophenoxy)-N-(methylsulfonyl)benzamide | 328 |
| 196 | 4-(2,3-difluoro-4-methoxyphenoxy)-N-(methylsulfonyl)benzamide | 358 |
| 197 | 4-[2-(1-methyl-1H-pyrazol-3-yl)phenoxy]-N-(methylsulfonyl)benzamide | 372 |
| 198 | 4-(3-chloro-4-methylphenoxy)-N-(methylsulfonyl)benzamide | 340 |
| 199 | 4-(4-fluoro-3-methylphenoxy)-N-(methylsulfonyl)benzamide | 324 |
| 200 | 4-(3-chloro-4-fluorophenoxy)-N-(methylsulfonyl)benzamide | 344 |
| 201 | 4-(4-fluoro-2-methylphenoxy)-N-(methylsulfonyl)benzamide | 324 |
| 202 | 4-(3-chlorophenoxy)-N-(methylsulfonyl)benzamide | 326 |
| 203 | 4-(2-chloro-4-methylphenoxy)-N-(methylsulfonyl)benzamide | 340 |

-continued

| Ex | Name | MS m/z |
|---|---|---|
| 204 | 4-(3-methoxy-5-methylphenoxy)-N-(methylsulfonyl)benzamide | 336 |
| 205 | 4-(2-fluoro-5-methylphenoxy)-N-(methylsulfonyl)benzamide | 324 |
| 206 | 4-(4-chloro-2-methylphenoxy)-N-(methylsulfonyl)benzamide | 340 |
| 207 | 4-[2-chloro-5-(trifluoromethyl)phenoxy]-N-(methylsulfonyl)benzamide | 394 |
| 208 | 4-[4-fluoro-3-(trifluoromethyl)phenoxy]-N-(methylsulfonyl)benzamide | 378 |
| 209 | N-(methylsulfonyl)-4-[2-(trifluoromethoxy)phenoxy]benzamide | 376 |
| 210 | 4-[2-chloro-3-(trifluoromethyl)phenoxy]-N-(methylsulfonyl)benzamide | 394 |
| 211 | 4-(2-cyanophenoxy)-N-(methylsulfonyl)benzamide | 317 |
| 212 | 4-(3-chloro-4-cyanophenoxy)-N-(methylsulfonyl)benzamide | 351 |
| 213 | 4-(3-chlorophenoxy)-2-methoxy-N-(methylsulfonyl)benzamide | 356 |
| 214 | 3-chloro-4-(4-chlorophenoxy)-N-(methylsulfonyl)benzamide | 360 |
| 215 | 3-chloro-4-(4-methylphenoxy)-N-(methylsulfonyl)benzamide | 340 |
| 216 | 4-(4-fluoro-3-methylphenoxy)-2-methoxy-N-(methylsulfonyl)benzamide | 354 |
| 217 | 3-fluoro-4-(4-methylphenoxy)-N-(methylsulfonyl)benzamide | 324 |
| 218 | 3-fluoro-4-(4-fluoro-3-methylphenoxy)-N-(methylsulfonyl)benzamide | 342 |
| 219 | 3-fluoro-4-(4-fluorophenoxy)-2-methoxy-N-(methylsulfonyl)benzamide | 358 |
| 220 | 4-(4-chloro-3-fluorophenoxy)-N-(methylsulfonyl)benzamide | 344 |
| 221 | 4-(4-chloro-3-fluorophenoxy)-3-fluoro-2-methoxy-N-(methylsulfonyl)benzamide | 392 |
| 222 | 4-(4-chlorophenoxy)-3-fluoro-2-methoxy-N-(methylsulfonyl)benzamide | 374 |
| 223 | 4-(3-chlorophenoxy)-3-fluoro-N-(methylsulfonyl)benzamide | 344 |
| 224 | 4-(3-chloro-4-methylphenoxy)-3-fluoro-2-methoxy-N-(methylsulfonyl)benzamide | 388 |
| 225 | 4-(3-chlorophenoxy)-3-fluoro-2-methoxy-N-(methylsulfonyl)benzamide | 374 |
| 226 | 3-fluoro-2-methoxy-4-(4-methylphenoxy)-N-(methylsulfonyl)benzamide | 354 |
| 227 | 3-fluoro-4-(4-fluoro-3-methylphenoxy)-2-methoxy-N-(methylsulfonyl)benzamide | 372 |
| 228 | 4-(4-chloro-3-fluorophenoxy)-2-methoxy-N-(methylsulfonyl)benzamide | 374 |
| 229 | 4-(4-chlorophenoxy)-3-fluoro-N-(methylsulfonyl)benzamide | 344 |
| 230 | 4-(4-chloro-3-methylphenoxy)-3-fluoro-2-methoxy-N-(methylsulfonyl)benzamide | 388 |
| 231 | 4-(4-chloro-3-methylphenoxy)-2-methoxy-N-(methylsulfonyl)benzamide | 370 |
| 232 | 4-(3-chloro-4-fluorophenoxy)-3-fluoro-2-methoxy-N-(methylsulfonyl)benzamide | 392 |
| 233 | 4-(3-chloro-4-fluorophenoxy)-2-methoxy-N-(methylsulfonyl)benzamide | 374 |
| 234 | 4-(3,4-dichlorophenoxy)-3-fluoro-2-methoxy-N-(methylsulfonyl)benzamide | 408 |
| 235 | 4-(4-chlorophenoxy)-2-methoxy-N-(methylsulfonyl)benzamide | 356 |
| 236 | 3-cyano-N-(methylsulfonyl)-4-[3-(trifluoromethyl)phenoxy]benzamide | 385 |
| 237 | 4-(4-fluorophenoxy)-3-methyl-N-(methylsulfonyl)benzamide | 324 |
| 238 | 4-(3-chlorophenoxy)-3-methyl-N-(methylsulfonyl)benzamide | 340 |
| 239 | 3-methoxy-N-(methylsulfonyl)-4-[3-(trifluoromethoxy)phenoxy]benzamide | 406 |
| 240 | 4-(4-chlorophenoxy)-3-methyl-N-(methylsulfonyl)benzamide | 340 |
| 241 | 4-[4-fluoro-3-(trifluoromethyl)phenoxy]-3-methoxy-N-(methylsulfonyl)benzamide | 408 |
| 242 | 4-(3,5-dichlorophenoxy)-3-fluoro-2-methoxy-N-(methylsulfonyl)benzamide | 408 |
| 243 | 2-cyano-N-(methylsulfonyl)-4-[4-(trifluoromethyl)phenoxy]benzamide | 385 |
| 244 | N-(methylsulfonyl)-4-(2-naphthyloxy)benzamide | 342 |
| 245 | 4-(biphenyl-4-yloxy)-N-(methylsulfonyl)benzamide | 366 |
| 246 | 3-chloro-N-(methylsulfonyl)-4-(2-naphthyloxy)benzamide | 376 |
| 247 | N-(methylsulfonyl)-4-(1-naphthyloxy)benzamide | 342 |
| 248 | 3-chloro-4-(2-chlorophenoxy)-N-(methylsulfonyl)benzamide | 360 |
| 249 | 3-chloro-4-(2-methoxyphenoxy)-N-(methylsulfonyl)benzamide | 356 |
| 250 | 3-chloro-4-(3-methylphenoxy)-N-(methylsulfonyl)benzamide | 338 |
| 251 | 4-(2-ethoxyphenoxy)-N-(methylsulfonyl)benzamide | 334 |
| 252 | 3-chloro-N-(methylsulfonyl)-4-phenoxybenzamide | 324 |
| 253 | 4-(4-ethoxyphenoxy)-N-(methylsulfonyl)benzamide | 336 |
| 254 | 4-(3-methylphenoxy)-N-(methylsulfonyl)benzamide | 304 |
| 255 | 3-chloro-4-(3-methoxyphenoxy)-N-(methylsulfonyl)benzamide | 356 |
| 256 | 3-chloro-4-(2-methylphenoxy)-N-(methylsulfonyl)benzamide | 338 |
| 257 | 3-chloro-4-(4-methoxyphenoxy)-N-(methylsulfonyl)benzamide | 356 |
| 258 | 3-chloro-N-(methylsulfonyl)-4-(1-naphthyloxy)benzamide | 376 |
| 259 | 4-(3-ethoxyphenoxy)-N-(methylsulfonyl)benzamide | 336 |
| 260 | 4-(2-methoxyphenoxy)-N-(methylsulfonyl)benzamide | 322 |
| 261 | 4-(biphenyl-3-yloxy)-N-(methylsulfonyl)benzamide | 368 |

-continued

| Ex | Name | MS m/z |
|---|---|---|
| 262 | 3-chloro-4-(3-fluorophenoxy)-N-(methylsulfonyl)benzamide | 342 |
| 263 | 3-chloro-4-(3-ethoxyphenoxy)-N-(methylsulfonyl)benzamide | 370 |
| 264 | 3-chloro-4-(3-cyanophenoxy)-N-(methylsulfonyl)benzamide | 349 |
| 265 | 3-cyano-4-(4-ethoxyphenoxy)-N-(methylsulfonyl)benzamide | 359 |
| 266 | 3-chloro-N-(methylsulfonyl)-4-[3-(trifluoromethyl)phenoxy]benzamide | 392 |
| 267 | 3-cyano-4-(2-methoxyphenoxy)-N-(methylsulfonyl)benzamide | 345 |
| 268 | 4-(biphenyl-2-yloxy)-N-(methylsulfonyl)benzamide | 366 |
| 269 | 3-cyano-N-(methylsulfonyl)-4-(2-naphthyloxy)benzamide | 365 |
| 270 | 3-chloro-4-(4-cyanophenoxy)-N-(methylsulfonyl)benzamide | 349 |
| 271 | 3-cyano-N-(methylsulfonyl)-4-[2-(trifluoromethyl)phenoxy]benzamide | 383 |
| 272 | 4-(biphenyl-3-yloxy)-3-cyano-N-(methylsulfonyl)benzamide | 391 |
| 273 | 3-cyano-4-(2-ethoxyphenoxy)-N-(methylsulfonyl)benzamide | 359 |
| 274 | 3-cyano-4-(4-methoxyphenoxy)-N-(methylsulfonyl)benzamide | 345 |
| 275 | 3-cyano-4-(2-methylphenoxy)-N-(methylsulfonyl)benzamide | 329 |
| 276 | 4-(2-chlorophenoxy)-3-cyano-N-(methylsulfonyl)benzamide | 349 |
| 277 | 3-cyano-4-(3-methoxyphenoxy)-N-(methylsulfonyl)benzamide | 345 |
| 278 | 3-chloro-N-(methylsulfonyl)-4-[2-(trifluoromethyl)phenoxy]benzamide | 394 |
| 279 | 3-chloro-4-(2-cyanophenoxy)-N-(methylsulfonyl)benzamide | 349 |
| 280 | 4-(biphenyl-4-yloxy)-3-cyano-N-(methylsulfonyl)benzamide | 391 |
| 281 | 3-chloro-4-(3-ethoxyphenoxy)-N-(methylsulfonyl)benzamide | 359 |
| 282 | 3-chloro-4-(2-fluorophenoxy)-N-(methylsulfonyl)benzamide | 344 |
| 283 | 3-cyano-N-(methylsulfonyl)-4-(1-naphthyloxy)benzamide | 365 |
| 284 | 3-cyano-4-(3-fluorophenoxy)-N-(methylsulfonyl)benzamide | 333 |
| 285 | 5-chloro-2-fluoro-N-(methylsulfonyl)-4-(2-naphthyloxy)benzamide | 392 |
| 286 | 5-chloro-4-(4-cyanophenoxy)-2-fluoro-N-(methylsulfonyl)benzamide | 367 |
| 287 | 5-chloro-2-fluoro-N-(methylsulfonyl)-4-(1-naphthyloxy)benzamide | 392 |
| 288 | 5-chloro-4-(2-ethoxyphenoxy)-2-fluoro-N-(methylsulfonyl)benzamide | 386 |
| 289 | 5-chloro-2-fluoro-4-(3-methoxyphenoxy)-N-(methylsulfonyl)benzamide | 372 |
| 290 | 5-chloro-4-(3-cyanophenoxy)-2-fluoro-N-(methylsulfonyl)benzamide | 367 |
| 291 | 5-chloro-2-fluoro-4-(4-methylphenoxy)-N-(methylsulfonyl)benzamide | 356 |
| 292 | 5-chloro-4-(3-chlorophenoxy)-2-fluoro-N-(methylsulfonyl)benzamide | 376 |
| 293 | 5-chloro-4-(2-cyanophenoxy)-2-fluoro-N-(methylsulfonyl)benzamide | 367 |
| 294 | 5-chloro-4-(4-ethoxyphenoxy)-2-fluoro-N-(methylsulfonyl)benzamide | 386 |
| 295 | 5-chloro-4-(4-chlorophenoxy)-2-fluoro-N-(methylsulfonyl)benzamide | 376 |
| 296 | 5-chloro-2-fluoro-4-(4-fluorophenoxy)-N-(methylsulfonyl)benzamide | 360 |
| 297 | 5-chloro-2-fluoro-4-(2-methylphenoxy)-N-(methylsulfonyl)benzamide | 356 |
| 298 | 5-chloro-4-(3-ethoxyphenoxy)-2-fluoro-N-(methylsulfonyl)benzamide | 388 |
| 299 | 5-chloro-2-fluoro-4-(2-fluorophenoxy)-N-(methylsulfonyl)benzamide | 360 |
| 300 | 5-chloro-4-(2-chlorophenoxy)-2-fluoro-N-(methylsulfonyl)benzamide | 376 |
| 301 | 5-chloro-2-fluoro-4-(4-methoxyphenoxy)-N-(methylsulfonyl)benzamide | 372 |
| 302 | 3-cyano-4-(3-methylphenoxy)-N-(methylsulfonyl)benzamide | 329 |
| 303 | 4-[4-chloro-2-(1-methyl-1H-pyrazol-5-yl)phenoxy]-3-cyano-N-(methylsulfonyl)benzamide | 431 |
| 304 | 4-(4-methylphenoxy)-N-(methylsulfonyl)benzamide | 306 |
| 305 | N-(ethylsulfonyl)-4-(4-fluorophenoxy)benzamide | 324 |
| 306 | N-(ethylsulfonyl)-4-(3-fluorophenoxy)benzamide | 324 |
| 307 | N-(ethylsulfonyl)-4-phenoxybenzamide | 306 |
| 308 | N-(ethylsulfonyl)-4-(4-methylphenoxy)benzamide | 320 |
| 309 | 4-(4-fluorophenoxy)-N-(methylsulfonyl)benzamide | 310 |
| 310 | 4-[4-cyano-3-(trifluoromethyl)phenoxy]-N-(methylsulfonyl)benzamide | 383 [M − H]− |
| 311 | 4-[4-(1H-imidazol-1-yl)phenoxy]-N-(methylsulfonyl)benzamide | 358 |
| 312 | N-(methylsulfonyl)-4-{4-[1-methyl-3-(trifluoromethyl)-1H-pyrazol-5-yl]phenoxy}benzamide | 457 [MNH$_4$]+ |
| 313 | 5-chloro-2-fluoro-N-(methylsulfonyl)-4-[2-pyridazin-4-yl-4-(trifluoromethyl)phenoxy]benzamide | 490 |
| 314 | 2,5-difluoro-4-[2-methoxy-5-(trifluoromethoxy)phenoxy]-N-(methylsulfonyl)benzamide | 440 [M − H]− |

EXAMPLE 315

4-(3,4-Dichlorobenzyl)-N-(methylsulfonyl)benzamide

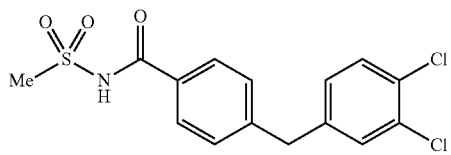 [SMILES: CS(=O)(=O)NC(=O)c1ccc(Cc2ccc(Cl)c(Cl)c2)cc1]

To a solution of 4-(3,4-dichlorobenzyl)benzoic acid (Preparation 148,150 mg, 0.54 mmol) in dichloromethane (25 mL) was added methanesulphonamide (153 mg, 1.61 mmol), 4-dimethylaminopyridine (196 mg, 1.61 mmol) and N-(3-dimethylaminopropyl)-N'-ethylcarbodiimide hydrochloride (307 mg, 1.61 mmol) and the mixture was stirred at room temperature for 5 hours. The mixture was diluted with dichloromethane, washed with water and 1M hydrochloric acid solution, dried over Na$_2$SO$_4$ and the solvent evaporated in vacuo. The crude product was purified by silica gel column chromatography eluting with 95:5 dichloromethane:methanol to afford the title compound (102 mg, 53%).

LCMS Rt=7.26 minutes, MS m/z 356 [M-H]−

$^1$HNMR (400 MHz, DMSO): δ 3.34 (s, 3H), 4.04 (s, 2H), 7.25 (d, 1H), 7.40 (d, 2H), 7.56 (d, 2H), 7.88 (d, 2H), 12.03 (br s, 1H)

EXAMPLE 316

N-(Methylsulfonyl-1)-4-[3-(trifluoromethoxy)benzyl]benzamide

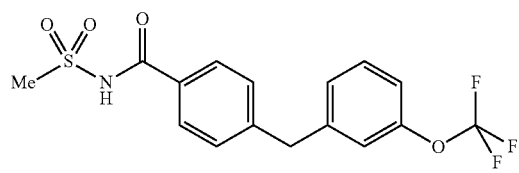 [SMILES: CS(=O)(=O)NC(=O)c1ccc(Cc2cccc(OC(F)(F)F)c2)cc1]

To a solution of 4-[3-(trifluoromethoxy)benzyl]benzoic acid (Preparation 150, 300 mg, 1.02 mmol) in dichloromethane (50 mL) was added methanesulphonamide (290 mg, 3.05 mmol), 4-dimethylaminopyridine (373 mg, 3.05 mmol) and N-(3-dimethylaminopropyl)-N'-ethylcarbodiimide hydrochloride (583 mg, 3.05 mmol) and the mixture was stirred at room temperature for 5 hours. The mixture was diluted with dichloromethane, washed with 1M hydrochloric acid solution and water, dried over $Na_2SO_4$ and the solvent evaporated in vacuo. The crude product was purified by preparative HPLC to afford the title compound (95 mg, 25%).

LCMS Rt=3.52 minutes, MS m/z 374 [MH]+

$^1$HNMR (400 MHz, DMSO): δ 3.35 (s, 3H), 4.09 (s, 2H), 7.20 (d, 1H), 7.25-7.34 (m, 2H), 7.39-7.45 (m, 3H), 7.88 (d, 2H), 12.02 (br s, 1H)

EXAMPLE 317

4-[(3,4-Dichlorophenyl)sulfanyl]-N-(methylsulfonyl)benzamide

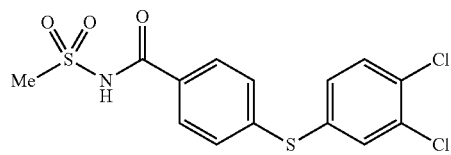 [SMILES: CS(=O)(=O)NC(=O)c1ccc(Sc2ccc(Cl)c(Cl)c2)cc1]

To a stirred solution of 4-[(3,4-dichlorophenyl)sulfanyl]benzoic acid (Preparation 151, 200 mg, 0.67 mmol) in dichloromethane (5 mL) was added methanesulphonamide (192 mg, 2.01 mmol), 4-dimethylaminopyridine (245 mg, 2.01 mmol) and N-(3-dimethylaminopropyl)-M-ethylcarbodiimide hydrochloride (384 mg, 2.01 mmol) and the mixture was stirred at room temperature for 18 hours. The mixture was diluted with dichloromethane, washed with 1M hydrochloric acid solution and water, dried over $Na_2SO_4$ and the solvent evaporated in vacuo. The crude product was purified by preparative HPLC to afford the title compound as a white solid (34 mg, 12%).

LCMS Rt=3.12 minutes, MS m/z 376 [MH]+

$^1$HNMR (400 MHz, DMSO): δ 3.19 (s, 3H), 7.26-7.30 (m, 1H), 7.34 (d, 2H), 7.49-7.52 (m, 2H), 7.93 (d, 2H) [acylsulphonamide NH not observed]

EXAMPLE 318

N-(Methylsulfonyl)-4-{[3-(trifluoromethoxy)phenyl]sulfanyl}benzamide

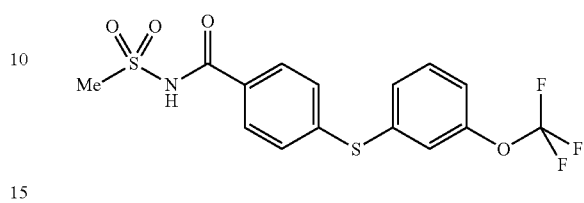

To a stirred solution of 4-{[3-(trifluoromethyl)phenyl]sulfanyl}benzoic acid (Preparation 152, 400 mg, 1.26 mmol) in benzene (4 mL) was added thionyl chloride (2.0 mL, 6.34 mmol) and 2 drops of dimethylformamide. The mixture was stirred for 2 hours and then concentrated under reduced pressure. The residue was suspended in dichloromethane and the solvent evaporated and this process repeated twice. The crude acid chloride was suspended in dichloromethane (10 mL) and methanesulphonamide (359 mg, 3.78 mmol) added followed by N-ethyldiisopropylamine (1.0 mL, 6.30 mmol) and the mixture was stirred at room temperature for 12 hours. The mixture was diluted with water (30 mL) and extracted dichloromethane (3×30 mL). The extracts were combined, dried over $Na_2SO_4$ and the solvent evaporated in vacuo. Purification by silica gel column chromatography eluting with hexane:ethyl acetate (7:3) gave the desired product (60 mg, 20%) in 87% purity. Further purification by preparative HPLC gave the title compound (30 mg, 10%).

LCMS Rt=3.08 minutes, MS m/z 390 [M-H]−

$^1$HNMR (400 MHz, DMSO): δ 2.97 (s, 3H), 7.24 (s, 1H), 7.29-7.32 (m, 2H), 7.37-7.40 (d, 2H), 7.49-7.53 (m, 1H), 7.94-7.96 (d, 2H) [acylsulphonamide NH not observed]

EXAMPLE 319

4-(4-Chloro-2-methoxybenzyl)-2,5-difluoro-N-(methylsulfonyl)benzamide

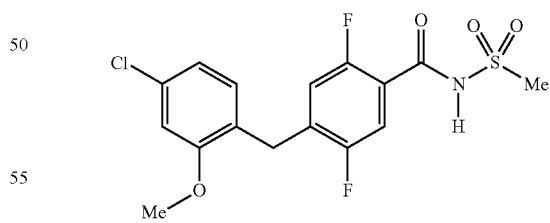

4-(Bromomethyl)-2,5-difluoro-N-(methylsulfonyl)benzamide (Preparation 164, 100 mg, 0.27 mmol), (4-chloro-2-methoxyphenyl)boronic acid (55 mg, 0.295 mmol), tetrakis(triphenylphosphine)palladium (31 mg, 0.027 mmol), aqueous potassium carbonate solution (1.8 M, 0.45 mL, 0.804 mmol) and tetrahydrofuran (15 mL) were combined and stirred under nitrogen at reflux for 6 hours. After cooling, the mixture was filtered through Celite™ and the filtrate evaporated. The residue was dissolved in water (20 mL) and acidified with aqueous potassium hydrogen sulphate solution (0.5 M) to pH 2 and the mixture extracted with ethyl acetate (1×30 mL). The organic layer was separated and back-washed with brine (2×20 mL). The organic layer was separated, dried over sodium sulphate, filtered and evaporated to give an orange oil. The oil was purified using silica gel column chromatography eluting with heptane to ethyl acetate:heptane 1:1 to give a solid. The solid was further purified by reverse phase HPLC to give the title compound (38 mg, 36%) as a white solid.

LCMS Rt=2.32 minutes MS m/z 390 [MH]+

EXAMPLE 320

3-chloro-4-(4-chloro-3-(trifluoromethyl)phenoxy)-2-fluoro-N-(methylsulfonyl)benzamide

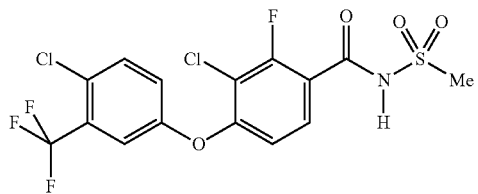 [SMILES: CS(=O)(=O)NC(=O)c1ccc(Oc2ccc(Cl)c(C(F)(F)F)c2)c(Cl)c1F]

3-chloro-4-(4-chloro-3-(trifluoromethyl)phenoxy)-2-fluorobenzoic acid (Preparation 153, 0.133 g, 0.360 mmol) was slurried in dichloromethane (0.6 mL). N-(3-dimethylaminopropyl)-N'-ethylcarbodiimide hydrochloride (100 mg, 0.54 mmol), 1-hydroxybenzotriazole (49 mg, 0.36 mmol) and N,N-diisopropylethylamine (75 µL, 0.43 mmol) were added to the slurry. The reaction mixture was stirred 20 minutes then methanesulfonamide (100 mg, 1.1 mmol) was added and the stirring continued for 18 hours at ambient temperature. The solvent was removed in vacuo to leave a residue. The residue was purified by semi-preparative reverse phase HPLC (Phenomenex 100×21.2 mm 10 micron C18 column. 20 mL/minutes. Gradient 85% A to 100% B over 25 minutes. Solvent A: 7800 water/200 acetonitrile/8 trifluoroacetic acid. Solvent B: 7200 acetonitrile/800 water/8 trifluoroacetic acid, 254 nM UV detection) to afford the title compound as a white solid (132 mg).

$^1$HNMR (d$_6$-DMSO): δ 3.37 (s, 3H), 7.06 (dd, 1H), 7.47 (dd, 1H), 7.63-7.69 (m, 2H), 7.82 (d, 1H), 12.38 (br s, 1H).

LCMS Rt=1.30 minutes MS m/z 444 [M-H]−

EXAMPLE 321

N-(methylsulfonyl)-4-(3-(trifluoromethyl)phenylamino)benzamide

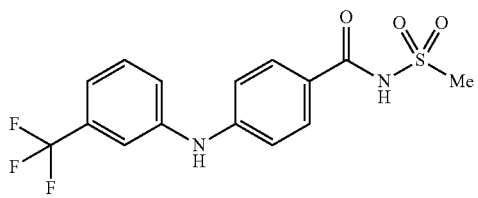 [SMILES: CS(=O)(=O)NC(=O)c1ccc(Nc2cccc(C(F)(F)F)c2)cc1]

To a solution of 4-(3-(trifluoromethyl)phenylamino)benzoic acid (150 mg, 0.533 mmol) in DMF (4 mL) were added HATU (243 mg, 0.640 mmol), methanesulfonamide (152 mg, 1.60 mmol) and DIPEA (0.296 mL) and the reaction stirred at room temperature for 16 hours. Methanesulfonamide (152 mg, 1.60 mmol) was added and the reaction stirred at room temperature for 72 hours. After this time the reaction was quenched by the addition of potassium hydrogen sulfate (20 mL) and the aqueous extracted with dichlormethane (3×20 mL). The combined organics were washed with brine (40 mL), filtered through a phase separation cartridge and then the solvent was removed under reduced pressure to give an oil (325 mg). The crude was purified by preparative HPLC to give the title compound.

LCMS Rt=3.36 minutes MS m/z 359 [MH]+

EXAMPLE 322

4-(3,4-dichlorobenzyl)-3-methoxy-N-(methylsulfonyl)benzamide

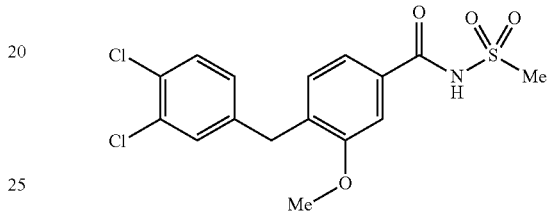

To a solution of 4-(3,4-dichlorobenzyl)-3-methoxybenzamide (Preparation 155, 155 mg, 0.50 mmol) in anyhydrous THF (5 mL) was added 1M LiHMDS (1.25 mL, 1.25 mmol) via syringe. The mixture was stirred for 20 minutes before adding mesyl chloride (0.116 mL, 1.50 mmol) and then stirred for 18 hours at room temperature. The reaction was quenched with the addition of 2M HCl (20 mL), and the aqueous was extracted with EtOAc (3×20 mL). The combined organics were concentrated in vacuo and the residue was purified by silica gel column chromatography eluting with a gradient of 25% EtOAc in heptane to 100% EtOAc. The title compound was obtained as a white solid (40 mg, 21%).

LCMS Rt=3.29 minutes, MS m/z 388 [MH]+

EXAMPLE 323

4-(2-chlorophenylthio)-N-(methylsulfonyl)benzamide

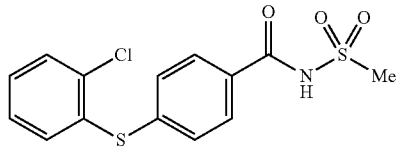 [SMILES: CS(=O)(=O)NC(=O)c1ccc(Sc2ccccc2Cl)cc1]

4-(2-chlorophenylthio)benzoic acid (132 mg, 0.50 mmol), 4-dimethylaminopyridine (12.2 mg, 0.10 mmol) and 1-ethyl-3-(dimethylaminopropyl)carbodiimide (192 mg, 1.00 mmol) were dissolved in anhydrous N,N-dimethylformamide (4 mL) and stirred for 60 minutes.

To this solution was added methanesulphonamide (71 mg, 0.75 mmol) and the reaction mixture was stirred at room temperature for 18 hours. The reaction was quenched by the addition of water (10 mL) and the mixture extracted with ethyl acetate (2×6 mL), dried over anhydrous magnesium sulfate, filtered and concentrated in vacuo to give 50 mg of a crude oil which was purified by preparative HPLC to afford the title compound.

LCMS Rt=2.31 minutes, MS m/z 342 [MH]+

EXAMPLE 324

4-(2-methoxyphenylthio)-N-(methylsulfonyl)benzamide

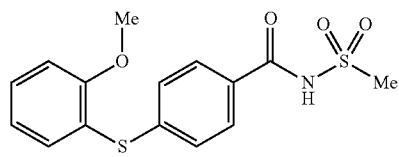 [SMILES: COc1ccccc1Sc1ccc(C(=O)NS(C)(=O)=O)cc1]

4-(2-methoxyphenylthio)benzoic acid (126 mg, 0.48 mmol), 4-dimethylaminopyridine (12.2 mg, 0.10 mmol) and 1-ethyl-3-(dimethylaminopropyl)carbodiimide (195 mg, 0.97 mmol) were dissolved in anhydrous N,N-dimethylformamide (4 mL) and stirred for 60 minutes. To this solution was added methanesulphonamide (70 mg, 0.72 mmol) and the reaction mixture was stirred at room temperature for 18 hours. The reaction was quenched by the addition of water (10 mL) and the mixture extracted with ethyl acetate (3×10 mL), dried over anhydrous magnesium sulfate, filtered and concentrated in vacuo to give 50 mg of a crude oil which was purified by preparative HPLC title compound.

LCMS Rt=1.93 minutes MS m/z 338 [MH]+

EXAMPLE 325

5-chloro-4-(3,4-dichlorophenylthio)-2-fluoro-N-(methylsulfonyl)benzamide

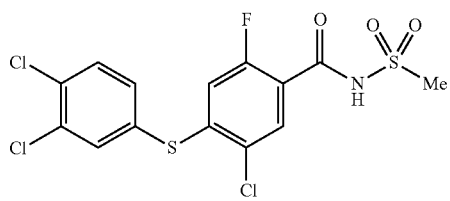 [SMILES: CS(=O)(=O)NC(=O)c1cc(Cl)c(Sc2ccc(Cl)c(Cl)c2)cc1F]

N,N-Diisopropylethylamine (0.248 mL, 1.422 mmol) and methansulfonamide (135 mg, 1.42 mmol) were added to a mixture of 5-chloro-4-(3,4-dichlorophenylthio)-2-fluorobenzoic acid (Preparation 159, 250 mg, 0.71 mmol), 4-dimethylaminopyridine (130 mg, 1.07 mmol), 1-[3-(dimethylamino)propyl]-3-ethylcarbodiimide (204 mg, 1.07 mmol) in DCM (4.4 mL) and the reaction stirred at room temperature for 18 hours. The reaction was concentrated to dryness and the residue taken up in EtOAc (30 mL), washed with 1N aq. HCl (2×5 mL), brine (4×5 mL), dried over MgSO$_4$, filtered and evaporated to give a yellow solid. The solid was purified using silica gel column chromatography eluting with 19:1 DCM:heptanes to afford the title compound as a white solid (221 mg, 73%).

LCMS Rt=4.12 minutes, 427 [MH]−

$^1$H-NMR (400 MHz, CDCl$_3$): δ 3.41 (s, 3H), 6.47 (d, 1H), 7.41 (dd, 1H), 7.61 (d, 1H), 7.68 (d, 1H), 8.06 (d, 1H), 8.66 (br s, 1H)

EXAMPLE 326

4-(4-chloro-3-(trifluoromethyl)phenoxy)-2-methoxy-N-(methylsulfonyl)benzamide

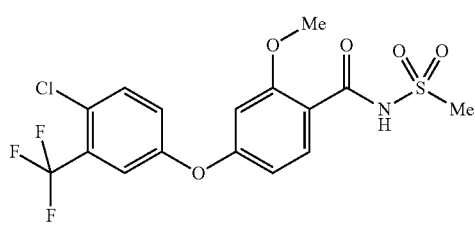 [SMILES: COc1cc(Oc2ccc(Cl)c(C(F)(F)F)c2)ccc1C(=O)NS(C)(=O)=O]

A solution of 4-(4-chloro-3-(trifluoromethyl)phenoxy)-2-methoxybenzaldehyde (Preparation 166, 0.470 g, 1.42 mmol) in tert-butyl acetate (8 mL) was prepared, then methanesulfonamide (0.135 g, 1.42 mmol) and bis(t-butylcarbonyloxy)iodobenzene (0.577 g, 1.42 mmol) were added. After stirring for 5 minutes, bis[rhodium(tetramethyl-1,3-benzenedipropionic acid)] (0.054 g, 0.07 mmol) was added and the reaction mixture was stirred at room temperature for 18 hours. The reaction was diluted with ethyl acetate (50 mL) and washed with water (50 mL). The organic layer was dried over magnesium sulfate, the filtrate was evaporated and the residue was purified by reverse phase to give a solid product. This product was dissolved in heptane/ethyl acetate 3:1, some of the ethyl acetate was removed in vacuo until a solid start to precipitate and then was left to stand for 18 hours. The resulting crystalline solid was collected by filtration to give the title compound as a light brown crystalline solid (0.386 g, 64%).

LCMS Rt=2.56 minutes, m/z 424 [MH]$^+$ $^1$HNMR (400 MHz, CDCl$_3$): δ 3.40 (s, 3H), 4.00 (s, 3H), 6.60 (d, 1H), 6.65 (s, 1H), 7.20 (dd, 1H), 7.40 (d, 1H), 7.55 (d, 1H), 8.20 (d, 1H), 10.00 (s, 1H).

EXAMPLE 327

4-(2-cyanophenoxy)-2,5-difluoro-N-(methylsulfonyl)benzamide

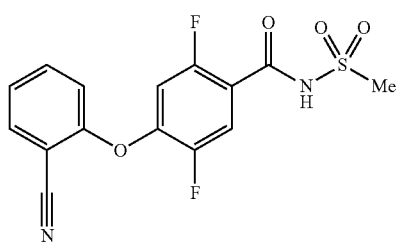 [SMILES: CS(=O)(=O)NC(=O)c1cc(F)c(Oc2ccccc2C#N)cc1F]

To 2-fluorobenzonitrile (12.1 mg, 0.100 mmol) was added potassium carbonate (27.6 mg, 0.200 mmol) and a solution of 2,5-difluoro-4-hydroxy-N-(methylsulfonyl)benzamide (Preparation 34, 32.7 mg 0.130 mmol) in dimethyl sulfoxide (1.0 mL). The reaction mixture was shaken at 120° C. for 5 hours. The reaction mixture was purified on an HPLC column (DIKMA Diamonsil(2) C18 200*20 mm*5 um, acetonitrile-water (0.225% formic acid) gradient) to afford the title compound (3.50 mg, 9.93 μmol).

LCMS Rt=2.877 minutes MS m/z 353 [MH]+

LCMS conditions

| | |
|---|---|
| Column | Welch XB-C18 2.1 × 50 mm 5 μm |
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 1% B |
| Time 0.00 mins | 1% B |
| Time 0.50 mins | 5% B |
| Time 4.00 mins | 100% B |
| Time 4.30 mins | 1% B |
| Time 4.70 mins | 1% B |
| Flow rate | 0.8 ml/min |
| Injection volume | 2 μl |
| Agilent | 1200 HPLC/1956 MSD/SEDEX 75 ELSD |
| Ionization Mode | API-ES |
| Polarity | Positive |

PREPARATION 1

Methyl 4-[4-chloro-3-(trifluoromethyl)phenoxy]benzoate

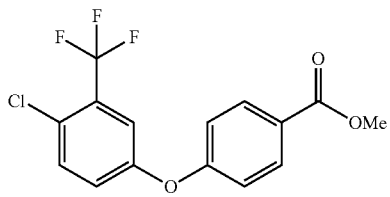 [SMILES: COC(=O)c1ccc(Oc2ccc(Cl)c(C(F)(F)F)c2)cc1]

4-Chloro-3-(trifluoromethyl)phenol (1.19 g, 6.06 mmol), methyl 4-fluorobenzoate (0.934 g, 6.06 mmol) and potassium carbonate (2.51 g, 18.2 mmol) were stirred in dimethylsulfoxide (10 mL) at 120° C. overnight under an atmosphere of nitrogen. The temperature was then increased to 130° C. and the reaction mixture stirred for a further 17 hours. The reaction mixture was cooled to room temperature. Water (100 mL) was added and the mixture extracted with ethyl acetate (3×50 mL). The combined organic phase was washed sequentially with water (50 mL) and brine (50 mL), dried over magnesium sulphate, filtered and concentrated in vacuo to afford the title compound as a yellow oil (1.92 g, 96%, contains residual dimethylsulfoxide). This material was taken on crude in subsequent steps.

$^1$HNMR ($d_6$-DMSO): δ 3.82 (s, 3H), 7.18 (m, 2H), 7.42 (m, 1H), 7.60 (m, 1H), 7.78 (m, 1H), 8.00 (m, 2H).

LCMS Rt=3.71 minutes MS m/z 331 [MH]+

PREPARATION 2

4-[4-Chloro-3-(trifluoromethyl)phenoxy]benzoic acid

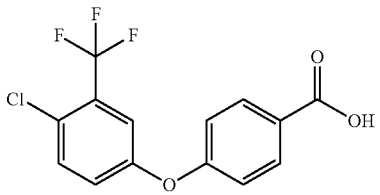 [SMILES: O=C(O)c1ccc(Oc2ccc(Cl)c(C(F)(F)F)c2)cc1]

Methyl 4-[4-chloro-3-(trifluoromethyl)phenoxy]benzoate (Preparation 1, 2.7 g, 8.34 mmol) was dissolved in methanol (50 mL) followed by addition of a 1M aqueous solution of lithium hydroxide (50 mL, 50 mmol) whereupon a precipitate was observed. The reaction mixture was heated to 50° C. to aid dissolution and the reaction mixture then stirred at 50° C. 18 hours. The reaction mixture was concentrated in vacuo. The resulting residue was dissolved in a 1M aqueous solution of sodium carbonate (~100 mL) and extracted with ethyl acetate (30 mL). The organic phase was concentrated in vacuo to give a yellow solid. The solid was partitioned between tert-butylmethyl ether and a 1M aqueous solution of sodium carbonate. The organic phase was washed sequentially with a 2M aqueous solution of hydrogen chloride and brine, dried over anhydrous magnesium sulphate, filtered and concentrated in vacuo to afford the title compound as an off-white solid (1.44 g, 55%).

$^1$HNMR ($d_6$-DMSO): δ 7.15 (m, 2H), 7.40 (m, 1H), 7.58 (m, 1H), 7.78 (m, 1H), 7.99 (m, 2H), 12.90 (br s, 1H).

LCMS Rt=3.43 minutes MS m/z 315 [MH]-

PREPARATION 3

4-Methylphenyl 5-chloro-4-(3,4-dichlorophenoxy)-2-fluorobenzoate

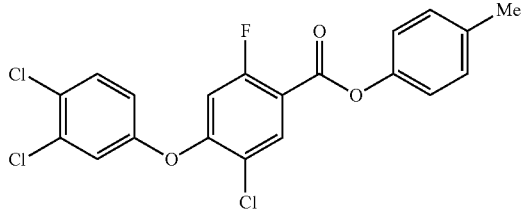 [SMILES: Cc1ccc(OC(=O)c2cc(Cl)c(Oc3ccc(Cl)c(Cl)c3)cc2F)cc1]

3,4-Dichlorophenol (110 mg, 0.67 mmol) and potassium carbonate (20 mg, 1.42 mmol) were stirred in dimethylsulfoxide (20 mL). After 5 minutes, 4-methylphenyl 5-chloro-2,4-difluorobenzoate (Preparation 10, 200 mg, 0.71 mmol) was added and the reaction mixture was stirred at room temperature overnight. The reaction mixture was diluted with ethyl acetate and washed with a 1M aqueous solution of sodium hydroxide. The aqueous phase was extracted with ethyl acetate. The combined organic phase was dried over magnesium sulphate, filtered and concentrated in vacuo to give a white solid. The solid was purified by silica gel column chromatography (50% ethyl acetate in heptane elution) to afford the title compound as a white solid (286 mg, 95%).

$^1$HNMR (CDCl$_3$): δ 2.38 (s, 3H), 6.68 (d, 1H), 6.95 (d, 1H), 7.08 (d, 2H), 7.17-7.24 (m, 3H), 7.80 (d, 1H), 8.21 (d, 1H).

LCMS Rt=7.03 minutes MS m/z 425 [MH]+

PREPARATION 4

1-(5-chloro-2-methoxyphenyl)ethanol

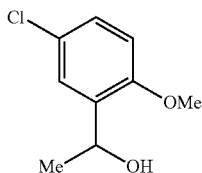 [SMILES: COc1ccc(Cl)cc1C(C)O]

To a solution of 1-(5-chloro-2-methoxyphenyl)ethanone (7.97 g, 43.1 mmol) in anhydrous tetrahydrofuran (40 mL) at 0° C. was added a 1M solution of lithium aluminium hydride In THF (14.2 mL, 14.2 mmol). After 3 hours, ethyl acetate (200 mL) was added and the mixture was washed with a 1M aqueous solution of hydrogen chloride (50 mL). The organic phase was concentrated in vacuo to afford the title compound (6.97 g, 86%)

$^1$HNMR (d$_6$-DMSO): δ 1.20 (m, 3H), 3.80 (s, 3H), 4.90 (m, 1H), 5.15 (m, 1H), 6.95 (m, 1H), 7.20 (m, 1H), 7.40 (m, 1H).

LCMS Rt=2.21 minutes

PREPARATION 5

4-Chloro-2-ethyl-1-methoxybenzene

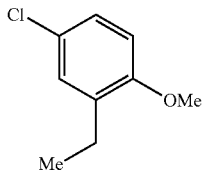 [SMILES: CCc1cc(Cl)ccc1OC]

1-(5-Chloro-2-methoxyphenyl)ethanol (Preparation 4, 6.97 g, 37.3 mmol), was dissolved in trifluoroacetic acid (20 mL). Triethylsilane (29.8 mL, 187 mmol) was added and the reaction mixture stirred at room temperature overnight. The reaction mixture was concentrated in vacuo. The resulting residue was dissolved in ethyl acetate and washed with water. The organic phase was separated and concentrated in vacuo to afford the title compound (9 g, 141%, contains residual triethylsilane). This material was taken on crude in subsequent steps.

$^1$HNMR (d$_6$-DMSO): δ 1.10 (m, 3H), 2.50 (m, 2H), 3.40 (s, 3H), 7.90 (m, 1H), 8.10 (m, 2H).

LCMS Rt=3.87 minutes

PREPARATION 6

4-Chloro-2-ethylphenol

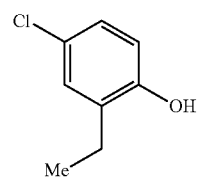

To a solution of 4-chloro-2-ethyl-1-methoxybenzene (Preparation 5, 7.0 g, 41.0 mmol) in dichloromethane (20 mL) at 0° C. was added a 1M solution of boron tribromide in dichloromethane (20.5 mL, 20.5 mmol). After 2 hours, further boron tribromide solution (20 mL, 20.0 mmol) was added. After a further 2 hours, methanol was added and the reaction mixture concentrated in vacuo. The residue was purified by silica gel column chromatography (5%-40% ethyl acetate in heptane) to afford the title compound (3.7 g, 58%).

$^1$HNMR (d$_6$-DMSO): δ 1.10 (m, 3H), 2.50 (m, 2H), 6.75 (m, 1H), 7.00 (m, 1H), 7.05 (s, 1H), 9.50 (s, 1H).

LCMS Rt=2.50 minutes Ms m/z 155 [MH]–

PREPARATION 7

2,4,5-Trifluoro-N-(methylsulfonyl)benzamide

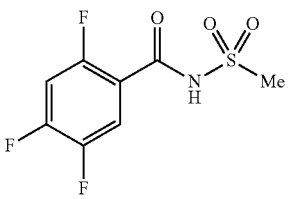 [SMILES: CS(=O)(=O)NC(=O)c1cc(F)c(F)cc1F]

2,4,5-Trifluorobenzoic acid (15 g, 85.2 mmol), 1-ethyl-3-(dimethylaminopropyl)carbodiimide (24.45 g, 128 mmol) and 4-dimethylaminopyridine (15.6 g, 128 mmol) were stirred in dichloromethane at room temperature for 15 minutes under an atmosphere of nitrogen. Methanesulfonamide (12.15 g, 128 mmol) and triethylamine (23.8 g, 254 mmol) were added and the reaction stirred at room temperature overnight. A 1M aqueous solution of hydrogen chloride was added and the mixture was extracted with ethyl acetate. The organic phase was washed sequentially with brine, dried over anhydrous magnesium sulphate, filtered and concentrated in vacuo. The resulting residue was recrystallised from a mixture of ethyl acetate and heptane to afford the title compound (7.8 g, 36%).

$^1$HNMR (CDCl$_3$): δ 3.40 (s, 3H), 7.05 (m, 1H), 8.00 (m, 1H), 8.70 (s, 1H).

LCMS Rt=1.70 minutes MS m/z 252 [MH]–

PREPARATION 8

3-Bromo-4-(3,4-dichlorophenoxy)benzoic acid

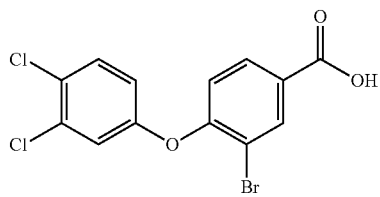 [SMILES: O=C(O)c1ccc(Oc2ccc(Cl)c(Cl)c2)c(Br)c1]

Methyl 3-bromo-4-fluorobenzoate (Preparation 122, 500 mg, 2.15 mmol), 3,4-dichlorophenol (350 mg, 2.15 mmol) and caesium carbonate (1.4 g, 4.29 mmol) were stirred in dimethylsulfoxide (10 mL). The reaction mixture was heated to 120° C. and stirred overnight under an atmosphere of nitrogen. A 1M aqueous solution of sodium hydroxide was added and the mixture extracted with ethyl acetate. The aqueous phase was acidified and extracted with ethyl acetate. The organic phase from the second extraction was concentrated in vacuo and the resulting residue was purified by silica gel column chromatography (30%-100% ethyl acetate in heptane) to afford the title compound as a white solid (244 mg, 31%).

LCMS Rt=3.58 minutes MS m/z 359 [MH]−

PREPARATION 9

4-(3,4-Dichlorophenoxy)-3-ethylbenzoic acid

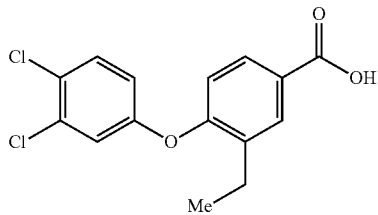 [SMILES: CCc1cc(C(=O)O)ccc1Oc1ccc(Cl)c(Cl)c1]

3-Bromo-4-(3,4-dichlorophenoxy)benzoic acid (Preparation 8, 240 mg, 0.663 mmol) was dissolved in anhydrous tetrahydrofuran (3 mL) and cooled to 0° C. Bis(tributylphosphine)palladium (0) (33.7 mg, 0.07 mmol) was added followed by the slow addition of a 1M solution of diethyl zinc in hexane (3.32 mL, 3.32 mmol). The reaction mixture was stirred overnight under an atmosphere of nitrogen. The reaction mixture was then quenched with a 1M aqueous solution of hydrogen chloride and extracted with ethyl acetate. The combined organic phase was concentrated in vacuo and the resulting residue then purified by reverse phase column chromatography (Trilution method) to afford the title compound as a white solid (75 mg, 36%).

$^1$HNMR (d$_6$-DMSO): δ 1.19 (m, 3H), 2.62 (m, 2H), 7.00 (m, 2H), 7.33 (m, 1H), 7.63 (m, 1H), 7.80 (m, 1H), 7.90 (m, 1H), 12.90 (br s, 1H).

LCMS Rt=3.67 minutes MS m/z 309 [MH]−

PREPARATION 10

4-methylphenyl 5-chloro-2,4-difluorobenzoate

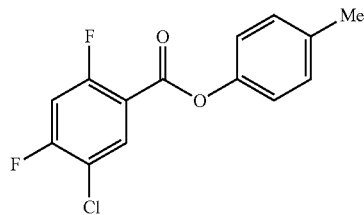 [SMILES: Cc1ccc(OC(=O)c2cc(Cl)c(F)cc2F)cc1]

5-chloro-2,4-difluorobenzoic acid (1.17 g, 0.00608 mol) was dissolved in thionyl dichloride (5.0 mL) and the reaction mixture was heated to 60° C. under nitrogen for 5 hours. The solvent was concentrated in vacuo and the residue was azeotroped twice with dichloromethane (10.0 mL) and once with toluene (10.0 mL). The crude was taken up in dichloromethane (15.0 mL) and cooled to 0° C. with an ice bath under nitrogen. Then N,N-diethylethanamine (1.05 mL, 0.00753 mol) and p-cresol (0.665 g, 0.00615 mol) dissolved in dichloromethane (10.0 mL) were added using a dropping funnel over 10 minutes. The resulting mixture was left to warm up to room temperature for 16 hours. The reaction was concentrated in vacuo and the crude was diluted in ethyl acetate (15.0 mL), washed twice with a saturated aqueous solution of sodium hydrogen carbonate (10.0 mL). The organic layer was then dried over sodium sulfate, filtered, and concentrated in vacuo. Resulting crude was taken up in heptane (10.0 mL), put in a sonication bath for 5 minutes and the resulting solid was isolated by filtration. Title compound was obtained as white solid (1.20 g, 0.00425 mol, 70%).

LCMS Rt=1.89 minutes MS m/z 283 [MH]+
$^1$H NMR (400 MHz, D$_6$-DMSO): δ 2.31 (s, 3H), 7.15-7.20 (d, 2H), 7.25-7.30 (d, 2H), 7.80 (t, 1H), 8.28 (t, 1H)

PREPARATION 11

4-methylphenyl 5-chloro-4-[3-chloro-4-(trifluoromethyl)phenoxy]-2-fluorobenzoate

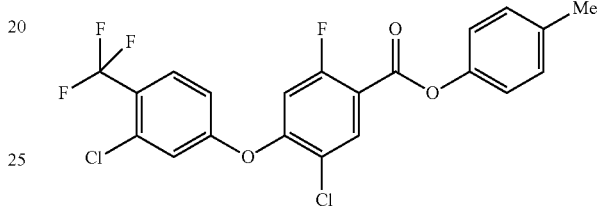

To a solution of 3-chloro-4-(trifluoromethyl)phenol (Preparation 16, 100 mg, 0.470 mmol) in DMSO (1 mL) was added potassium carbonate (0.84 mg, 0.611 mmol) and the mixture stirred for 5 minutes. 4-methylphenyl-5-chloro-2,4-difluorobenzoate (Preparation 10, 0.133 mg, 0.470 mmol) was then added and the reaction stirred under nitrogen for 3 hours. The reaction was quenched by the addition of water (2 mL) and ethyl acetate (3 ml). The organic layer was separated, dried over magnesium sulfate and concentrated in vacuo to afford a white solid that was purified using silica gel column chromatography eluting with ethyl acetate:heptane 3:97 to furnish the title compound (100 mg, 47%).

$^1$HNMR (CDCl$_3$): δ 2.40 (s, 3H), 6.75 (m, 1H), 7.00 (m, 2H), 7.01 (m, 1H), 7.22 (m, 3H), 7.38 (m, 1H), 8.24 (m, 1H).

LCMS Rt=5.86 minutes no mass ion detected.

PREPARATION 12

4-Methylphenyl 2,4,5-trifluorobenzoate

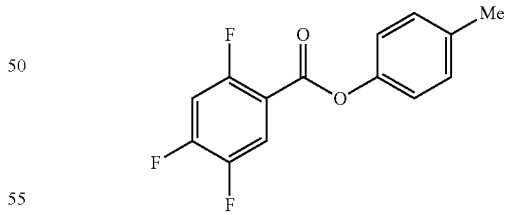

Thionyl chloride (50 mL, 680 mmol) was added to 2,4,5-trifluorobenzoic acid (10 g, 57 mmol) and the mixture stirred at 55° C. for 18 hours. After cooling, the excess thionyl chloride was removed in vacuo. The resulting crude oil was azeotroped twice with DCM (30 mL) and toluene (20 mL) and the residue redissolved in DCM (50 mL), then cooled to 0° C. with an ice bath. A mixture of 4-methylphenol (6.4 g, 59 mmol) and triethylamine (10 mL, 71 mmol) in DCM (20 mL) was added over 30 minutes. The reaction was allowed to warm up to room temperature over 1 hour. The crude reaction mixture was partitioned between EtOAc (200 mL) and saturated sodium bicarbonate solution (70 mL). The aqueous layer was separated and extracted with EtOAc (100 mL). The combined organic extracts were combined, washed with saturated sodium bicarbonate solution (70 mL) and water (100 mL), dried over magnesium sulfate and concentrated in vacuo to provide a crude solid, which was purified by silica gel chromatography eluting with 5% EtOAc in heptane to provide the title compound (10.08 g, 66%) as a white solid.

The title compound can also be prepared according to the following method: 4-methylphenol (80.0 g, 739.8 mmol) was added to a suspension of 2,4,5-trifluorobenzoic acid (136.8 g, 776.8 mmol) and 1,1-carbonyldiimidazole (83-85% wt, 163.6 g, 849.7 mmol) in EtOAc (1.20 L) at 40° C. The reaction mixture was stirred at 40° C. for 2 hours, then cooled to 20° C. and washed with water (480 mL), a 0.5 M aqueous solution of sodium hydroxide (2×400 mL) and water (400 mL). The organics were concentrated in vacuo and azeotroped with heptane to give a yellow oil. Heptane (640 mL) was added and the mixture was stirred at room temperature for 16 hours. A seed was used to facilitate the formation of a precipitate. The resulting suspension was cooled to 10° C. and filtered. The residue was washed with cold heptane (80 mL) and dried to afford the title compound as an off white solid (147.5 g, 75%):

$^1$HNMR (400 MHz, CDCl$_3$): δ 2.40 (s, 3H), 7.10 (m, 3H), 7.24 (m, 2H), 7.95 (m, 1H).

LCMS Rt=3.53 minutes

PREPARATION 13

5-chloro-2,4-difluoro-N-(methylsulfonyl)benzamide

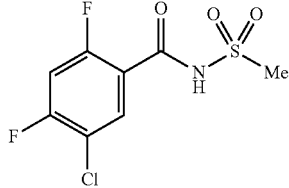 [SMILES: CS(=O)(=O)NC(=O)c1cc(Cl)c(F)cc1F]

5-chloro-2,4-difluorobenzoic acid (0.291 g, 1.511 mmol), N-Ethyl-N'-(3-dimethylaminopropyl)carbodiimide hydrochloride (0.438 g, 2.285 mmol) and 4-dimethylaminopyridine (0.420 g, 3.438 mmol) were suspended in DCM (5 mL). Methanesulfonamide (0.222 g, 2.334 mmol) was added and the mixture was stirred at room temperature for 18 hours. The reaction mixture was diluted with DCM (10 mL) and washed with aqueous HCl solution (2 M, 2×15 mL). The organic layer was dried with a phase separating cartridge and concentrated in vacuo to yield the title compound as a white solid (0.388 g):

LCMS Rt=1.43 minutes. MS m/z 268 [M-H]$^-$ $^1$H NMR (400 MHz; d$^6$-DMSO): δ 3.38 (s, 3H), 7.65 (t, 1H), 7.95 (t, 1H)

PREPARATION 14

4-[4-chloro-3-(trifluoromethyl)phenoxy]-2-fluoro-5-methylbenzaldehyde

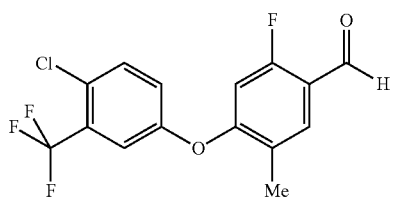 [SMILES: Cc1cc(C=O)c(F)cc1Oc1ccc(Cl)c(C(F)(F)F)c1]

To a solution of 2,4-difluoro-5-methylbenzaldehyde (100 mg, 0.64 mmol) and 4-chloro-3-trifluoromethylphenol (126 mg, 0.64 mmol) in DMSO was added potassium carbonate. The reaction was stirred at room temperature for 36 hours. The reaction was diluted with ethyl acetate (30 mL) and washed with water (2×50 mL), dried over magnesium sulfate and concentrated in vacuo. The residue was purified using reverse phase column chromatography eluting with acetonitrile:water (plus 0.1% aqueous formic acid) 5:95 to 100:0 to furnish the title compound as a white solid 104 mg, 49%.

$^1$HNMR (400 MHz, CDCl$_3$): δ 2.30 (s, 3H), 6.45 (m, 1H), 7.15 (m, 1H), 7.40 (m, 1H), 7.55 (m, 1H), 7.80 (m, 1H), 10.20 (s, 1H).

LCMS Rt=3.74 minutes MS m/z 333 [MH]+

PREPARATION 15

(2-(3-chloro-4-(trifluoromethyl)phenoxy)ethyl)trimethylsilane

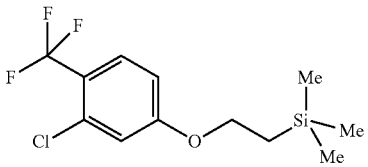 [SMILES: C[Si](C)(C)CCOc1ccc(C(F)(F)F)c(Cl)c1]

To 2-chloro-4-fluoro-(trifluoromethyl)benzene (2.39 g, 1.2 mmol) and 2-(trimethylsilyl)ethanol (2.13 g, 1.8 mmol) in anhydrous tetrahydrofuran (100 mL) was added sodium hydride (0.72 g, 1.8 mmol, 60% in mineral oil). The resulting mixture was stirred at room temperature for 18 hours under nitrogen. The reaction mixture was poured onto water and acidified with aqueous potassium hydrogen sulfate and extracted with ethyl acetate (3×30 mL), dried (MgSO$_4$), filtered and concentrated in vacuo to afford 3.1 g (87%) of the title compound as a colourless oil.

LCMS Rt=2.63 minutes MS m/z not observed $^1$HNMR (400 MHz, CDCl$_3$): δ 0.0 (s, 9H), 0.96 (m, 2H), 3.74 (m, 2H), 6.77 (m, 1H), 6.97 (m, 1H), 7.46 (m, 1H).

PREPARATION 16

3-chloro-4-(trifluoromethyl)phenol

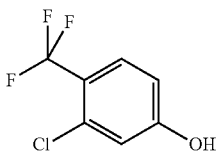

To a solution of (2-(3-chloro-4-(trifluoromethyl)phenoxy)ethyl)trimethylsilane (Preparation 15, 3.1 g, 10 mmol) in 1,4-dioxane (5 mL) was added tetrabutylammonium fluoride (10 mL, 1M in THF) and the resulting mixture was stirred at room temperature for 18 hours under nitrogen. The mixture was poured onto water and neutralised with aq. ammonium chloride and extracted with ethyl acetate (3×30 mL). The organic layer was separated and washed with 1M sodium hydroxide (3×30 mL). The aqueous layers were separated, combined, acidified with aqueous 2M HCl and re-extracted with ethyl acetate (3×30 mL), dried (MgSO₄), filtered and concentrated in vacuo to afford 2.46 g of a pale yellow oil. The crude oil was purified by silica gel column chromatography eluting with a gradient of 0-50% ethyl acetate in heptane to afford 619 mg (31%) of the title compound as a colourless oil.

LCMS Rt=2.97 minutes MS m/z 195 [M-H]+

¹HNMR (400 MHz, CDCl₃): δ 6.64 (br s, 1H), 6.76 (m, 1H), 6.96 (m, 1H), 7.50 (m, 1H),

PREPARATION 17

4-(3,4-dichlorophenoxy)-3-methoxybenzamide

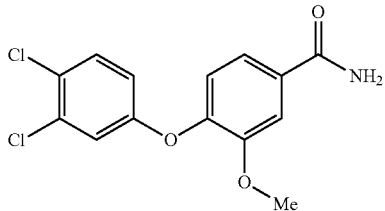 [SMILES: COc1cc(C(N)=O)ccc1Oc1ccc(Cl)c(Cl)c1]

A mixture of 3,4-dichlorophenol (539 mg, 3.31 mmol), 4-fluoro-3-methoxybenzonitrile (500 mg, 3.31 mmol) and cesium carbonate (2.16 g, 6.62 mmol) in DMSO (5 mL) was heated to 120° C. for 18 hours. The reaction was cooled before the addition of 1N NaOH. The reaction was extracted with ethyl acetate and the organic layer separated and concentrated in vacuo. The residue was purified using silica gel column chromatography eluting with 0-20% EtOAc in heptane to furnish the title compound as a white solid, 142 mg, 14%.

¹H NMR (400 MHz; d₆-DMSO): δ 3.78 (s, 3H), 6.82 (m, 1H), 7.17 (m, 2H), 7.40 (br s, 1H), 7.55 (m, 2H), 7.65 (m, 1H), 8.00 (br s, 1H).

LCMS Rt=3.03 minutes MS m/z 312 [MH]+

PREPARATION 18

5-chloro-4-[4-chloro-2-(1-methyl-1H-pyrazol-5-yl) phenoxy]-2-fluorobenzamide

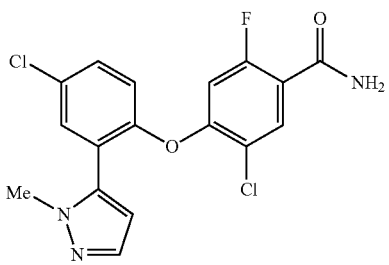 [SMILES: Cn1nccc1-c1cc(Cl)ccc1Oc1cc(F)c(C(N)=O)cc1Cl]

To a solution of 5-chloro-4-[4-chloro-2-(1-methyl-1H-pyrazol-5-yl)phenoxy]-2-fluorobenzonitrile (Preparation 19, 290 mg, 0.801 mmol) in DMSO (0.8 mL) was added hydrogen peroxide (545 μL, 16 mmol) followed by potassium carbonate (221 mg, 1.60 mmol). The reaction was stirred at room temperature for 18 hours. The reaction was then purified directly using trilution reverse phase chromatography to furnish the title compound (320 mg, 105%).

¹H NMR (400 MHz; d₆-DMSO): δ 3.75 (s, 3H), 6.35 (m, 1H), 6.95 (m, 1H), 7.20 (m, 1H), 7.40 (m, 1H), 7.60 (m, 2H), 7.70 (m, 2H), 7.80 (m, 1H).

LCMS Rt=2.92 minutes MS m/z 380 [M H]+

PREPARATION 19

5-chloro-4-[4-chloro-2-(1-methyl-1H-pyrazol-5-yl) phenoxy]-2-fluorobenzonitrile

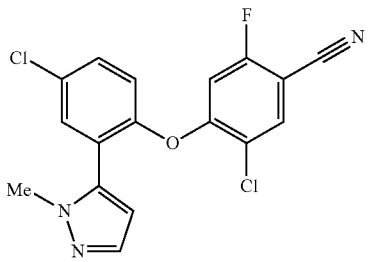 [SMILES: Cn1nccc1-c1cc(Cl)ccc1Oc1cc(F)c(C#N)cc1Cl]

To a solution of (4-chloro-2-(1-methyl)-1H-pyrazol-5-yl) phenol (Preparation 48, 264 mg, 1.27 mmol) in DMSO (5 mL) was added 2,4-difluoro-5-chlorobenzonitrile (200 mg, 1.15 mmol) and potassium carbonate (637 mg, 4.61 mmol). The reaction was heated to 90° C. for 18 hours before cooling and partitioning between ethyl acetate (50 mL) and water (20 mL). The organic layer was separated and concentrated in vacuo to afford a residue that was purified using silica gel column chromatography eluting with ethylacetate:heptane 0:1 to 6:4 to furnish the title compound (417 mg, 69%).

¹H NMR (400 MHz; d₆-DMSO): δ 3.75 (s, 3H), 6.30 (m, 1H), 7.10 (m, 1H), 7.40 (m, 2H), 7.65 (m, 2H), 8.20 (m, 1H).

LCMS Rt=1.85 minutes MS m/z 362 [MH]+

PREPARATION 20

2-fluoro-4-(2-ethyl-4-fluorophenoxy)-5-chlorobenzoic acid

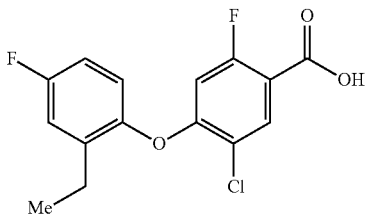 [SMILES: CCc1cc(F)ccc1Oc1cc(F)c(C(=O)O)cc1Cl]

To a solution of 2-ethyl-4-fluorophenol (364 mg, 2.60 mmol) in DMSO (10 mL) was added cesium carbonate (1690 mg, 5.19 mmol) and the mixture stirred at room temperature for 5 minutes. 5-chloro-2,4-difluorobenzoic acid (500 mg, 2.6 mmol) was added and the reaction heated to 110° C. for 18 hours. The reaction was cooled and quenched by the addition of 1N HCl (30 mL) and extracted into ethyl acetate (3×30 mL). The organic layers were combined, washed with brine (30 mL) and concentrated in vacuo before purifying using silica gel column chromatography eluting with ethylacetate: heptane 12:88 to 100:0 to furnish the title compound as a white solid (465 mg, 57%).

¹H NMR (400 MHz; d₆-DMSO): δ 1.10 (m, 3H), 2.50 (m, 2H), 6.60 (m, 1H), 7.12 (m, 2H), 7.27 (m, 1H), 8.00 (m, 1H), 13.40 (br s, 1H).
LCMS Rt=3.47 minutes MS m/z 311 [MH]−

PREPARATION 21

4,5-dichloro-2-methoxyphenol

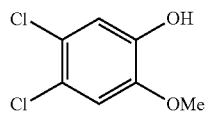 [SMILES: COc1cc(Cl)c(Cl)cc1O]

A suspension of 4,5-dichlorocatechol (1 g, 5.62 mmol), potassium carbonate (780 mg, 5.62 mmol), and methyl iodide (0.34 mL, 5.62 mmol) in N,N-dimethylformamide (20 mL) was stirred rapidly at 130° C. for 20 hours, under a nitrogen atmosphere. The reaction mixture was allowed to cool to room temperature before diluting with ethyl acetate (50 mL). The mixture was washed with water (50 mL), saturated aqueous sodium bicarbonate (50 mL), and saturated brine solution (50 mL). The organic layer was separated and dried over sodium sulphate, and evaporated under reduced pressure to a deep brown solid. The crude material was purified by flash chromatography (eluting with 1:1 heptane/dichloromethane) to afford 4,5-dichloro-2-methoxyphenol as a white solid (490 mg, 45%).
¹H NMR (400 MHz, CDCl₃): δ 3.88 (s, 3H), 6.90 (s, 1H), 7.00 (s, 1H).
LCMS Rt=2.28 minutes MS m/z 191 [M-H]−

PREPARATION 22

2-methoxy-4-(trifluoromethyl)phenol

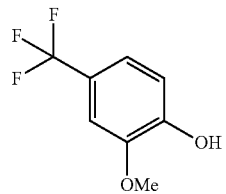 [SMILES: COc1cc(C(F)(F)F)ccc1O]

To a solution of 2-methoxy-4-(trifluoromethyl)benzaldehyde (1.0 g, 4.90 mmol) in dichloromethane (15 mL) was added m-chloroperoxybenzoic acid (1.48 g, 6.61 mmol). The resulting clear solution was stirred for 16 hours at room temperature. Overnight a white precipitate had formed that was filtered off. The filtrate was evaporated to a white solid, which was dissolved in ethyl acetate (25 mL) and washed with saturated aqueous sodium bicarbonate. The organic layer was dried over sodium sulphate, and evaporated to a white solid. This solid was redissolved in methanol (15 mL), and treated with triethylamine (2 mL, 10 mmol). After stirring for two hours, the mixture was concentrated in vacuo. The residue was taken up in ethyl acetate (25 mL), and washed with 1N citric acid solution (20 mL) and brine (20 mL). The organic layer was dried over sodium sulphate, and evaporated to an oil. This crude material was then purified by eluting through a short pad of silica with dichloromethane, which afforded the title compound as a clear oil (536 mg, 57%)

¹H NMR (400 MHz, CDCl₃): δ 3.95 (s, 3H), 6.95 (dd, 1H), 7.10 (m, 1H), 7.15 (d, 1H).
LCMS Rt: 2.16 minutes MS m/z 191 [M-H]⁻

PREPARATION 23

4-[4-chloro-2-(trifluoromethoxy)phenoxy]-2-methoxybenzoic acid

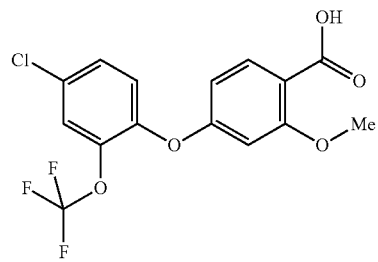 [SMILES: COc1cc(Oc2ccc(Cl)cc2OC(F)(F)F)ccc1C(=O)O]

To a solution of 4-[4-chloro-2-(trifluoromethoxy)phenoxy]-2-methoxybenzonitrile (Preparation 103, 230 mg, 0.66 mmol) in 10 mL of ethylene glycol/water (8:2) was added KOH flakes (380 mg, 6.6 mmol). The reaction mixture was heated to 120° C. for 64 hours. After cooling to room temperature the residue was partitioned between EtOAc (80 mL) and water (75 mL), the aqueous layer was separated, acidified with 2M HCl and extracted with EtOAc (2×50 mL). The organic layers were combined, dried over MgSO₄ and evaporated in vacuo to yield 167 mg of the title compound as yellow oil.
¹HNMR (400 MHz, CDCl₃): δ 4.04 (s, 3H), 6.55 (dd, 1H), 6.69 (d, 1H), 7.11 (d, 1H), 7.33 (dd, 1H), 7.41 (s, 1H), 8.14 (d, 1H).
LCMS: Rt=1.72 MS m/z 363 [MH]+ and 361 [M-H]−.

PREPARATION 24

4-chloro-2-(trifluoromethoxy)phenol

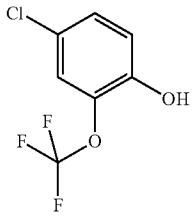 [SMILES: Oc1ccc(Cl)cc1OC(F)(F)F]

A solution of copper(II)chloride dihydrate (37.2 mmol, 6.34 g) and lithium chloride (18.6 mmol, 788 mg) in DMF (60 mL) was heated to 80° C. before the addition of 2-(trifluoromethoxy)phenol (18.6 mmol, 4 g) dropwise. The reaction was stirred at 100° C. for 72 hours. After cooling, the reaction mixture was partitioned between EtOAc (60 mL) and water (120 mL), extracted with EtOAc (60 mL). The organic layer was washed with water (60 mL), dried over MgSO₄, filtered and concentrated in vacuo. The crude material was purified by silica gel column chromatography, eluting product with a gradient of 0-100% DCM in heptane to yield the title compound as a waxy solid (637 mg, 10%). This was used in the next step with no further purification.

¹HNMR (400 MHz, CDCl₃): δ 5.34 (s, 1H), 6.91 (d, 1H), 7.10 (dd, 1H), 7.15-7.19 (m, 1H)

LCMS Rt=3.05 minutes MS m/z 211 [M-H]–

PREPARATION 25

3-chloro-4-(difluoromethoxy)phenol

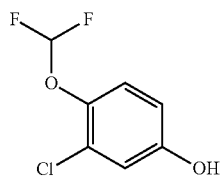 [SMILES: Oc1ccc(OC(F)F)c(Cl)c1]

To a solution of 4-bromo-2-chloro-1-(difluoromethoxy) benzene (Preparation 27, 0.83 g, 3.2 mmol) in THF (16 ml) was added 4,4,4',4',5,5,5',5'-octamethyl-2,2'-bi-1,3,2-dioxaborolane (0.90 g, 3.6 mmol), Pd(dppf)Cl₂ (0.12 g, 0.16 mmol), and potassium acetate (0.98 g, 9.7 mmol) under N₂ and the resulting mixture was heated to reflux for 2 hours. The reaction mixture was concentrated in vacuo and the residue filtered through a silica gel cake with arbocel on top washing through with EtOAc. The filtrate was concentrated in vacuo to give a crude product of 2-[3-chloro-4-(difluoromethoxy)phenyl]-4,4,5,5-tetramethyl-1,3,2-dioxaborolane. A solution of crude of 2-[3-chloro-4-(difluoromethoxy)phenyl]-4,4,5,5-tetramethyl-1,3,2-dioxaborolane (1.0 g, 3.3 mmol) in acetone (10 ml) was added to an aqueous oxone solution (2.6 g, 3.9 mmol, 10 mL) dropwise with stirring at 0° C. for 1 hour. The reaction mixture was partitioned between water (20 ml) and EtOAc (20 ml), the combined organic phase was washed with brine, dried over sodium sulphate, filtered, and concentrated in vacuo to give a crude product, which was purified by silica gel chromatography eluting with 0-40% EtOAc in Heptane to afford the title compound (0.53 g, 82% yield) as a pale brown oil.

¹HNMR (400 MHz, CDCl₃): δ 6.45 (m, 1H), 6.73 (d, 1H), 6.95 (d, 1H), 7.13 (t, 1H).

LCMS Rt=1.33 minutes MS m/z 195 [MH]⁺, 193 [M-H]⁻

PREPARATION 26

4-chloro-3-(difluoromethoxy)phenol

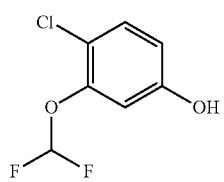

Prepared according to Preparation 25 using 4-bromo-2-(difluoromethoxy)chlorobenzene (Preparation 28, 1.5 g, 5.9 mmol).

¹HNMR (400 MHz, CDCl₃): δ 6.52 (t, 1H), 6.68 (d, 1H), 6.78 (t, 1H), 7.29 (d, 1H).

LCMS Rt=1.27 minutes MS m/z 193 [M-H]⁻

PREPARATION 27

4-bromo-2-chloro-(difluoromethoxy)benzene

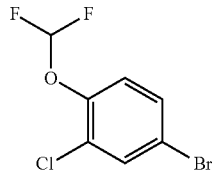 [SMILES: FC(F)Oc1ccc(Br)cc1Cl]

4-bromo-2-chlorophenol (1.0 g, 4.8 mmol) was dissolved in DMF (35 ml) and water (5 ml) was added followed by sodium chloro(difluoro)acetate (2.0 g, 12 mmol) and cesium carbonate (3.1 g, 9.6 mmol). The mixture was stirred for 15 minutes at room temperature and then heated to 100° C. for 2 hours under nitrogen. The mixture was partitioned between water (50 ml) and tBuOMe (50 ml). The organic phase was separated, washed brine, dried over sodium sulphate, filtered, and concentrated in vacuo to give a crude product. The crude product was purified by silica gel chromatography eluting with 0-30% EtOAc in heptanes to give a title compound (0.83 g, 67% yield) as colourless oil.

¹HNMR (400 MHz, CDCl₃): δ 6.52 (t, 1H), 7.14 (t, 1H), 7.40 (d, 1H), 7.62 (d, 1H).

LCMS Rt=1.66 minutes No mass ion detected.

PREPARATION 28

4-bromo-2-(difluoromethoxy)chlorobenzene

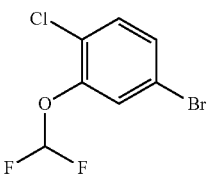 [SMILES: FC(F)Oc1cc(Br)ccc1Cl]

Prepared according to Preparation 27 using 5-bromo-2-chlorophenol (1.5 g, 7.2 mmol).

¹HNMR (400 MHz, CDCl₃): δ 6.54 (t, 1H), 7.32 (d, 2H), 7.41 (m, 1H).

LCMS Rt=1.70 minutes No mass ion detected.

PREPARATION 29

3,4,6-trifluoro-2-methoxybenzaldehyde

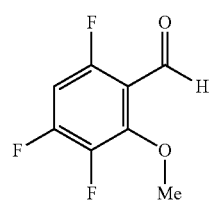 [SMILES: COc1c(F)c(F)cc(F)c1C=O]

Paraformaldehyde (0.960 g, 0.01066 mol) and magnesium chloride (0.505 g, 0.005304 mol) were suspended in tetrahydrofuran (10.0 mL). Triethylamine (0.75 mL, 0.0054 mol) was added and the mixture was stirred under nitrogen for 10 minutes. 2,3,5-trifluorophenol (0.524 g, 0.00027 mol) was then added and the reaction mixture was stirred at reflux for 16 hours. The reaction mixture was filtered and the filtrate was diluted with an aqueous solution of hydrochloric acid (2.0 M, 15.0 mL). The product was extracted with tert-butyl methyl ether (20.0 mL). The organic layer was dried over sodium sulfate, filtered, and concentrated in vacuo. The residue was dissolved in dimethylformamide (5.0 mL). Potassium carbonate (0.55 g, 0.003979 mol), followed by methyl iodide (0.175 mL, 0.00072 mol) were added to the mixture, which was stirred at 50° C. under nitrogen for 3 hours, then left to stir at room temperature for 72 hours. The reaction was diluted with an aqueous solution of saturated brine (15.0 mL) and the product was extracted with tert-butyl methyl ether (20.0 mL). The organic layers were combined, then dried over sodium sulfate, filtered, and concentrated in vacuo. The title compound was purified using silica gel column chromatography (gradient of 0-10% ethyl acetate in heptane, 40 g SiO$_2$) to afford the title compound as a colourless oil (0.080 g, 0.000432 mol, 16%).

LCMS Rt=1.07 minutes $^1$H NMR (400 MHz, CDCl$_3$): δ 4.14-4.15 (d, 3H), 6.68-6.74 (m, 1H), 10.27 (m, 1H)

PREPARATION 30

Ethyl 5-chloro-2,4-difluorobenzoate

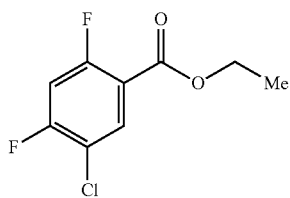 [SMILES: CCOC(=O)c1cc(Cl)c(F)cc1F]

5-chloro-2,4-difluorobenzoic acid (0.176 g, 0.000914 mol) was dissolved in thionyl chloride (2.0 mL). The reaction mixture stirred at 50° C. under nitrogen for 16 hours. The reaction mixture was concentrated in vacuo and azeotroped twice with dichloromethane (10.0 mL). The residue was taken up in dichloromethane (5.0 mL) and absolute ethanol (1.0 mL) was added dropwise to the reaction mixture, which was stirred at room temperature under nitrogen for 2 hours. The reaction mixture was concentrated in vacuo, dissolved in ethyl acetate (10.0 mL) and washed with a saturated aqueous solution of sodium hydrogen carbonate. The organic layer was dried over sodium sulfate, filtered, and concentrated in vacuo to give the title compound as a yellow oil (0.171 g, 0.000777 mol, 85%).

LCMS Rt=1.74 minutes $^1$H NMR (400 MHz, d$_6$-DMSO): δ 1.30 (t, 3H), 4.30 (s, 2H), 7.70 (m, 1H), 8.08 (m, 1H)

PREPARATION 31

4-chloro-2-(difluoromethoxy)phenol

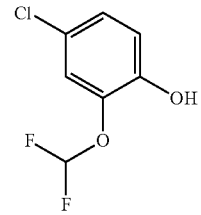 [SMILES: Oc1ccc(Cl)cc1OC(F)F]

To an ice cold suspension of 2-(difluoromethoxy)phenol (6.54 g, 0.00408 mol), aluminum trichloride (0.0544 g, 0.000408 mol) and 1,1'-thiodibenzene (0.068 mL, 0.000408 mol) was added sulfuryl dichloride (3.61 mL, 0.0449 mmol) dropwise. The reaction was allowed to warm to room temperature and stirred for 16 hours. The reaction was diluted in dichloromethane (10.0 mL) and purified using silica gel column chromatography eluting with 0-20% EtOAc in heptane. The title compound was isolated as a colourless oil (2.33 g, 0.01195 mol, 29%).

LCMS Rt=1.44 minutes MS m/z 193 [M-H]–

$^1$H NMR (400 MHz, CDCl$_3$): δ 5.50 (s, 1H), 6.36-6.73 (t, 1H), 6.96-6.98 (d, 1H), 7.11-7.13 (dd, 1H), 7.14-7.15 (m, 1H).

PREPARATION 32

5-chloro-4-[4-chloro-3-(trifluoromethyl)phenoxy]-2-fluorobenzoic acid

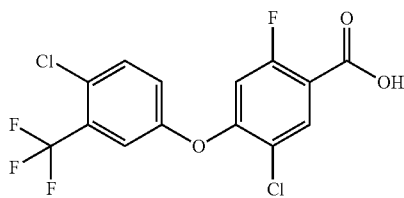 [SMILES: O=C(O)c1cc(Cl)c(Oc2ccc(Cl)c(C(F)(F)F)c2)cc1F]

t-butyl-5-chloro-4-(4-chloro-3-(trifluoromethyl)phenoxy)-2-fluorobenzoate (Preparation 50, 245 mg, 0.58 mmol) was dissolved in TFA (4 mL) and the reaction stirred at room temperature for 2 h. The TFA was removed under reduced pressure to give the title compound (219 mg, quant.) as an off-white solid.

$^1$H NMR (CDCl$_3$, 400 MHz): δ 6.66 (1H, d), 7.18 (1H, d), 7.44 (1H, s), 7.56 (1H, d) and 8.20 (1H, d).

LCMS Rt=3.36 minutes MS m/z 368 [M-H]–

PREPARATION 33

4-[4-chloro-3-(trifluoromethyl)phenoxy]-2-(methoxymethyl)benzoic acid

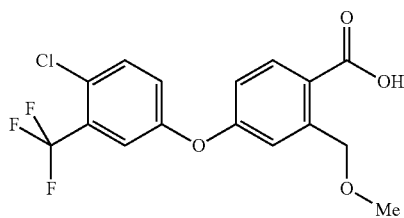 [SMILES: COCc1cc(Oc2ccc(Cl)c(C(F)(F)F)c2)ccc1C(=O)O]

To a solution of methyl 4-[4-chloro-3-(trifluoromethyl)phenoxy]-2-(methoxymethyl)benzoate (Preparation 34, 0.140 g, 0.000374 mol) in tetrahydrofuran (3.00 mL) and water (3.00 mL) was added lithium hydroxide (0.050 g, 0.00209 mol) and the reaction stirred at room temperature under nitrogen for 2 hours. Then more lithium hydroxide (0.500 g, 0.0209 mol) was added and the reaction stirred at room temperature under nitrogen for 16 hours. The reaction was diluted with ethyl acetate (10.0 mL) and washed with water (10.0 mL). The organic layer was separated, dried with sodium sulphate, filtered and concentrated in vacuo to yield title compound as a pale yellow foam (0.134 g, 0.000374 mol, 99% yield).

LCMS Rt=1.60 minutes MS m/z 359 [M-H]–

$^1$H NMR (400 MHz, d$_6$-DMSO): δ 3.30 (s, 3H), 4.78 (s, 2H), 6.88-6.91 (m, 1H), 7.06 (d, 1H), 7.26-7.29 (m, 1H), 7.44 (d, 1H), 7.70 (d, 1H), 7.77 (d, 1H).

PREPARATION 34 methyl 4-[4-chloro-3-(trifluoromethyl)phenoxy]-2-(methoxymethyl)benzoate

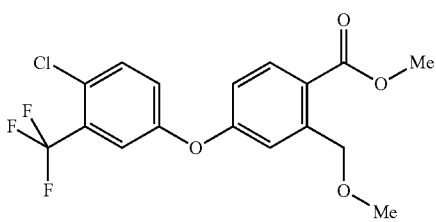 [SMILES: COCc1cc(Oc2ccc(Cl)c(C(F)(F)F)c2)ccc1C(=O)OC]

Prepared according to Preparation 1 using methyl 4-fluoro-2-(methoxymethyl)benzoate (Preparation 35) and 4-chloro-3-(trifluoromethyl)phenol at 120° C. for 48 hours. The title compound was isolated after purification using silica gel column chromatography eluting with 0-10% EtOAc in heptane as a colourless oil (0.140 g, 0.000374, 33% yield).

LCMS Rt=1.63 minutes MS m/z 375 [MH]+

$^1$H NMR (400 MHz, d$_6$-DMSO): δ 3.32 (s, 3H), 3.80 (s, 3H), 4.72 (s, 2H), 7.04-7.07 (m, 1H), 7.21 (m, 1H), 7.40-7.43 (m, 1H), 7.60 (m, 1H), 7.77 (d, 1H), 7.93 (d, 1H).

PREPARATION 35 methyl 4-fluoro-2-(methoxymethyl)benzoate

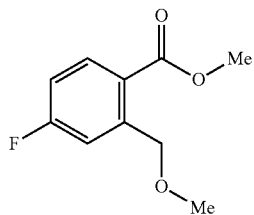 [SMILES: COCc1cc(F)ccc1C(=O)OC]

To a solution of 4-fluoro-2-(hydroxymethyl)benzoic acid (Preparation 36, 0.185 g, 0.001087 mol) in tetrahydrofuran (5.0 mL) was added sodium hydride (0.110 g, 0.0028 mmol, 60% in mineral oil) portion wise. The reaction was stirred for 15 minutes at room temperature under nitrogen. Then 0.17 mL iodomethane (0.17 mL, 0.00272 mol) was added and the reaction mixture stirred at room temperature under nitrogen for 16 hours. The reaction was quenched with an aqueous solution of hydrochloric acid (2.0M, 10.0 mL) and product was extracted with ethyl acetate (15.0 mL). The organic phase was dried over sodium sulfate, filtered and concentrated in vacuo. The residue was dissolved in dimethyl sulfoxide (3.0 mL), then potassium carbonate (0.170 g, 0.00123 mol) and iodomethane (0.17 mL, 0.00272 mol) were added. The reaction mixture was stirred at 60° C. under nitrogen for 2 hours. The reaction was diluted with ethyl acetate (15.0 mL) and washed three times with water (15.0 mL). The organic phase was dried over sodium sulfate, filtered and concentrated in vacuo. Title compound was isolated after purification using silica gel column chromatography eluting with 0-10% EtOAc in heptane as a colourless oil (0.135 g, 0.000681, 67% yield).

LCMS Rt=1.49 minutes $^1$H NMR (400 MHz, DMSO): δ 3.36 (s, 3H), 3.80 (s, 3H), 4.72 (s, 2H), 7.21-7.26 (m, 1H), 7.34-7.37 (d-d, 1H), 7.92-7.96 (m, 1H).

PREPARATION 36

4-fluoro-2-(hydroxymethyl)benzoic acid

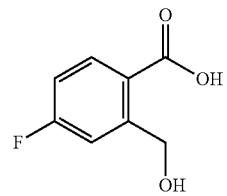

To a solution of 5-fluoro-2-benzofuran-1 (3H)-one (0.235 g, 0.00154 mol) in methanol (2.50 mL) and water (2.50 mL) was added potassium hydroxide (0.500 g, 0.00891 mol) and the reaction mixture was stirred at 50° C. under nitrogen for 2 hours. The reaction was diluted with an aqueous solution of hydrochloric acid (2.0 M, 10.0 mL). The aqueous layer was then extracted twice with ethyl acetate (2×15 mL). The organic layers were combined, then dried over sodium sulfate, filtered and concentrated in vacuo. The title compound was obtained after trituration in dichloromethane (8.0 mL) as a white solid (0.218 g, 0.00128 mol, 83% yield).

LCMS Rt=0.79 minutes MS m/z 169 [M-H]–

$^1$H NMR (400 MHz, d$_6$-DMSO): δ 4.82 (s, 2H), 7.12-7.17 (m, 1H), 7.43-7.47 (m, 1H), 7.91-7.95 (q, 1H)

PREPARATION 37

4-(4-chloro-3-(trifluoromethyl)phenoxy)-3,5-difluorobenzoic acid

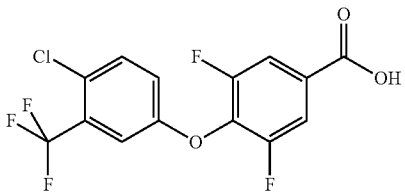 [SMILES: O=C(O)c1cc(F)c(Oc2ccc(Cl)c(C(F)(F)F)c2)c(F)c1]

Hydrochloric acid (6M, 20 mL) was added to a solution of 4-(4-chloro-3-(trifluoromethyl)phenoxy)-3,5-difluorobenzamide (Preparation 86, 440 mg, 1.25 mmol) in dioxan (10 mL). The reaction mixture was stirred at 120° C. for 5 h. After cooling the solvent was removed in vacuo and the aqueous residue was extracted with ethyl acetate (2×30 mL). The combined organic layers were washed with brine (1×20 mL), dried (MgSO₄), filtered and concentrated in vacuo. The residue was purified using silica gel column chromatography eluting with dichloromethane:methanol (from 98:2 to 85:15) then triturated with heptane to yield the title compound as a white solid (259 mg, 59%)

¹H NMR (400 MHz; d6-dmso): δ 7.35 (dd, 1H), 7.58 (s, 1H), 7.68 (d, 1H), 7.77 (d, 2H), 13.70 (bs, 1H).

LCMS Rt=3.56 minutes MS m/z 351 [M H]+

PREPARATION 38 tert-butyl 2,4,6-trifluorobenzoate

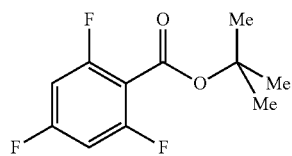 [SMILES: CC(C)(C)OC(=O)c1c(F)cc(F)cc1F]

To a solution of 2,4,6-trifluorobenzoic acid (2.0 g, 11.3 mmol) and dimethylaminopyridine (139 mg, 1.14 mmol) in tert-butanol (30 mL) was added di-tert-butyldicarbonate (4.95 g, 22.7 mmol), and the reaction heated to 40° C. for 18 hours. The reaction was quenched with 1M HCl and extracted into ethyl acetate. The combined organics were washed with 1M NaOH, followed by brine then concentrated in vacuo to afford the title compound as a pale yellow oil (2.63 g, 100%).

LCMS Rt=3.16 minutes

¹HNMR (400 MHz, CDCl₃): δ 1.58 (s, 9H), 6.67 (t, 2H).

PREPARATION 39

2,3,4,6-tetrafluorobenzoic acid

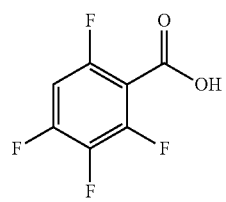 [SMILES: O=C(O)c1c(F)cc(F)c(F)c1F]

To a mixture of MeCN (20 mL), water (10 mL), carbon tetrachloride (20 mL) was added (2,3,4,6-tetrafluorophenyl)methanol (1.50 g, 8.33 mmol), sodium periodate (8.91 g, 41.6 mmol) and finally ruthenium (III) chloride (345 mg, 1.67 mmol). The reaction was stirred at room temperature for 6 hours before the mixture was filtered through Arbocel washing the pad thouroughly with ethyl acetate and directly purified by silica gel column chromatography eluting with ethyl acetate to afford the title compound as a colourless oil (1.60 g, 100%).

LCMS Rt=1.74 minutes

¹HNMR (400 MHz, CD₃OD): δ 5.06 (m, 1H).

PREPARATION 40 tert-butyl 2,3,4,6-tetrafluorobenzoate

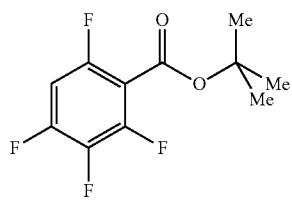 [SMILES: CC(C)(C)OC(=O)c1c(F)cc(F)c(F)c1F]

To a solution of 2,3,4,6-tetrafluorobenzoic acid (Preparation 39, 1.60 g, 8.88 mmol), dimethylaminopyridine (102 mg, 0.83 mmol) in tertbutanol (20 mL) was added di-tert-butyldicarbonate (3.63 g, 16.7 mmol) and the reaction stirred at 40° C. for 18 hours. The reaction was quenched with 1M HCl and extracted into ethyl acetate before washing with 1M NaOH then brine. The organic layer was concentrated in vacuo and purified by silica gel column chromatography eluting with 1:1 ethyl acetate:heptane to afford a colourless oil (1.25 g, 60%).

LCMS Rt=3.84 minutes

¹HNMR (400 MHz, CDCl₃): δ 1.57 (s, 9H), 6.73-6.85 (m, 1H).

PREPARATION 41 tert-butyl 2,4,5-trifluorobenzoate

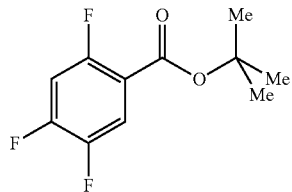

2,4,5-Trifluorobenzoic acid (10.0 g, 56.8 mmol) was dissolved in tert-butanol (280 mL). Di-tert-butyl dicarbonate (24.8 g, 114 mmol) was added portionwise followed by DMAP (0.694 g, 5.68 mmol) and the mixture stirred at 30° C. under nitrogen for 16 hours. EtOAc (400 mL) was added and the mixture washed with an aqueous solution of HCl (1M, 2×50 mL), then with a saturated aqueous solution of sodium hydrogen carbonate (2×50 mL), and finally with brine (2×50 mL). The organic layer was dried over sodium sulfate, filtered, and concentrated in vacuo to afford the title compound as a colourless oil (12.31 g, 93%):

¹HNMR (400 MHz, CDCl₃): δ 1.58 (s, 9H), 6.93-6.99 (m, 1H), 6.68-6.74 (m, 1H)

PREPARATION 42

2,4,5-trifluoro-N-(Phenylsulfonyl)benzamide

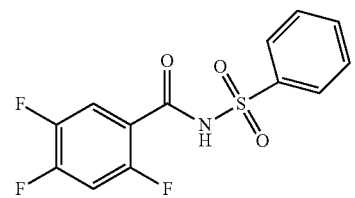 [SMILES: O=C(NS(=O)(=O)c1ccccc1)c1cc(F)c(F)cc1F]

To a solution of 2,4,5-trifluorobenzoic acid (0.50 g, 2.8 mmol) in dichloromethane (5 mL) was added N-di-isopropylethylamine (1.8 mL, 1.3 g, 8.5 mmol), WSCDI (0.82 g, 4.2 mmol) and DMAP (0.52 g, 4.2 mmol). After 10 minutes phenylsulfonamide (0.45 g, 4.2 mmol) was added and the reaction left at room temperature for 18 hours. The reaction mixture was concentrated in vacuo and the residue purified by reverse phase chromatography using CH$_3$CN/water as eluent (5:95-95/5 over 30 mins) to yield the title compound (0.60 g, 67%) as a white solid $^1$HNMR (400 MHz, d$_6$-DMSO): δ 7.60-7.80 (m, 5H), 8.00 (m, 2H).

LCMS Rt=2.77 minutes MS m/z 314 [M-H]+

PREPARATION 43

N-(sec-butylsulfonyl)-2,4,5-trifluorobenzamide

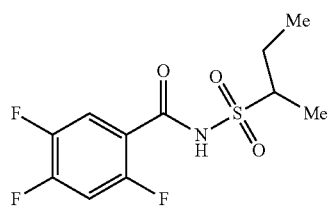 [SMILES: CCC(C)S(=O)(=O)NC(=O)c1cc(F)c(F)cc1F]

Prepared according to Preparation 42 using 2,4,5-trifluorobenzoic acid (0.25 g, 1.4 mmol) and butane-2-sulfonamide (0.0.29 g, 2.1 mmol) to yield the title compound (0.19 g, 45%) as a white solid.

$^1$HNMR (d$_6$-DMSO 400 MHz) δ 1.0 (m, 3H), 1.3 (s, 3H), 1.6 (m, 1H), 1.9 (m, 1H), 3.5 (m, 1H), 7.7 (m, 1H), 7.8 (m, 1H).

LCMS Rt=2.26 minutes MS m/z 294 [M-H]+

PREPARATION 44-(4-chloro-3-(trifluoromethyl)phenoxy)-2-fluorobenzoic acid

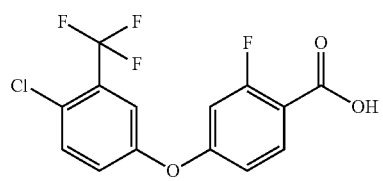 [SMILES: O=C(O)c1ccc(Oc2ccc(Cl)c(C(F)(F)F)c2)cc1F]

To a solution of ethyl 4-(4-chloro-3-(trifluoromethyl)phenoxy)-2-fluorobenzoate (Preparation 45, 1.80 g, 4.96 mmol) in THF (10 mL) was added 2N LiOH solution (7.5 mL) and the reaction mixture was left to stir at room temperature for 16 hours. The THF was removed under vacuum and the white residue was acidified to pH 1 using 6N HCl. The resulting solution was extracted with ethyl acetate (2×30 mL) then washed with brine (20 mL), dried (MgSO$_4$), filtered and evaporated. The resulting solid (mixture of regioisomers) was chromatographed by reverse phase using a Biotage cartridge (340 g SiO$_2$) and MeCN:water as eluent. The clean desired product was isolated as a white solid (24%, 400 mg).

$^1$H NMR (400 MHz, CDCl$_3$) δ 6.75 (1H, m), 6.85 (1H, m), 7.20 (1H, m), 7.40 (1H, m), 7.58 (1H, m), 8.05 (1H, m).

LCMS Rt=3.42 minutes MS m/z 333 [M-H]−

PREPARATION 45 ethyl 4-(4-chloro-3-(trifluoromethyl)phenoxy)-2-fluorobenzoate

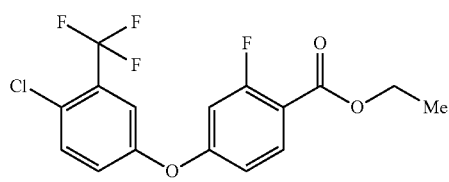 [SMILES: CCOC(=O)c1ccc(Oc2ccc(Cl)c(C(F)(F)F)c2)cc1F]

To a solution of 4-chloro-3-(trifluoromethyl)phenol (1.05 g, 5.34 mmol) in DMSO (10 mL) was added potassium carbonate (2.20 g 13.4 mmol, 2.5 eq.) and the suspension was left to stir for 5 minutes after which, ethyl 2,4-difluorobenzoate (1.0 g, 5.34 mmol) was added and the reaction mixture left to stir at 110° C. under nitrogen for 16 hours. The reaction mixture was cooled to room temperature and quenched with 1N NaOH (10 mL) then extracted into ethyl acetate (2×30 mL). The combined organic layers were washed with brine (30 mL), dried (MgSO$_4$), filtered and evaporated. The resulting residue was purified by column chromatography (SiO$_2$, 1:1 ethyl acetate: heptane) to give the desired product (mixture of regioisomers) as a colourless oil (1.8 g, 93% yield). This was taken directly on to the next step.

LCMS Rt=4.42 minutes

PREPARATION 46

4-[4-chloro-3-(trifluoromethyl)phenoxy]benzamide

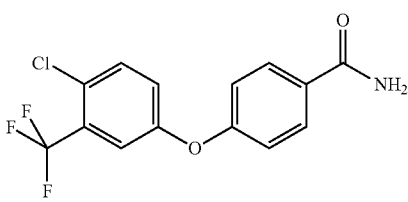 [SMILES: NC(=O)c1ccc(Oc2ccc(Cl)c(C(F)(F)F)c2)cc1]

To a solution of 4-[4-chloro-3-(trifluoromethyl)phenoxy] benzonitrile (Preparation 47, 48 g, 161 mmol) in DMSO (500 ml) was added K$_2$CO$_3$ (45 g, 323 mmol) followed by dropwise addition of a 30 wt % aqueous hydrogen peroxide solution (27 ml, 806 mmol) at 15° C. The reaction mixture was stirred for 1 hour at room temperature and the mixture was poured into water (500 ml) to afford a preciptate. The precipitated solid was collected by filtration, azeotroped with toluene, and dried over in vacuo to give 51 g of titled compound.

$^1$H NMR (400 MHz; d$_6$-DMSO): δ 7.11-7.19 (m, 2H), 7.31-7.40 (m, 1H), 7.53 (d, 1 H), 7.75 (d, 1H), 7.92-7.97 (m, 2H).

LCMS Rt=3.10 minutes MS m/z 316 [MH]$^+$, 314 [M-H]$^-$.

PREPARATION 47

4-[4-chloro-3-(trifluoromethyl)phenoxy]benzonitrile

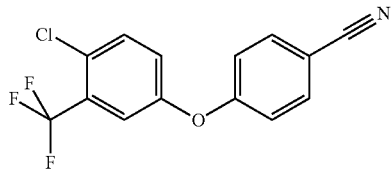 [SMILES: N#Cc1ccc(Oc2ccc(Cl)c(C(F)(F)F)c2)cc1]

To a solution of 4-chloro-3-(trifluoromethyl)phenol (31.5 g, 160 mmol) in DMSO (200 ml) was added $K_2CO_3$ (46.5 g, 337 mmol) at room temperature under nitrogen. After 5 minutes stirring, 4-fluorobenzonitrile (19.4 g, 160 mmol) was added to the mixture in one portion and the resulting mixture was stirred at 100° C. for 18 hours. The reaction mixture was allowed to cool to room temperature and poured into ice-cold 1N aqueous NaOH solution with vigorous stirring. The precipitated solid was collected by filtration and under vacuum to afford 50 g of the title compound.

$^1$H NMR (400 MHz; $d_6$-DMSO): δ 7.21 (d, 2H), 7.36-7.48 (m, 1H), 7.60 (s, 1H), 7.75 (d, 1H), 7.80-7.89 (m, 2H).

LCMS Rt=3.60 minutes MS m/z 298 [MH]$^+$.

PREPARATION 48

4-chloro-2-(1-methyl-1H-pyrazol-5-yl)phenol and 4-chloro-2-(1-methyl-1H-pyrazol-3-yl)phenol

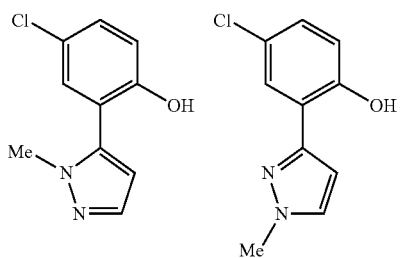 [SMILES: Cn1nccc1-c1cc(Cl)ccc1O ; Cn1ccc(-c2cc(Cl)ccc2O)n1]

To a suspension of 6-chlorochromone (2.00 g, 11.1 mol) in ethanol (35 mL) was added methylhydrazine sulfate (1.85 g, 12.8 mmol) and triethylamine (2.0 mL, 14.0 mmol). The reaction was heated to reflux for 18 hours. After cooling, the reaction was concentrated in vacuo and the residue purified by flash column chromatography eluting with 0-100% ethyl acetate/hexane gradient. Two regioisomeric products in a 1:4 A:B ratio were obtained with the major being the less polar and the minor being more polar.

A=4-chloro-2-(1-methyl-1H-pyrazol-5-yl)phenol

LCMS Rt=1.43 minutes MS m/z 209 [MH]+

$^1$H NMR (CDCl$_3$) δ 2.96 (s, 3H), 5.52 (m, 1H), 6.40 (d, 1H), 6.99 (d, 1H), 7.22 (d, 1H), 7.34 (dd, 1H), 7.65 (d, 1H).

B=4-chloro-2-(1-methyl-1H-pyrazol-3-yl)phenol

LCMS Rt=1.58 minutes MS m/z 209 [MH]+

$^1$H NMR (CDCl$_3$) δ 3.98 (s, 3H), 6.61 (d, 1H), 7.00 (d, 1H), 7.17 (dd, 1H), 7.44 (d, 1H), 7.54 (d, 1H), 10.85 (s, 1H).

PREPARATION 49

2-pyridazin-4-yl-4-(trifluoromethyl)phenol

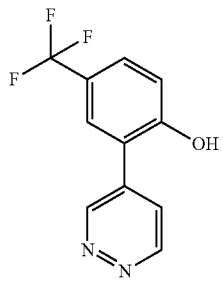

To a 5 L jacketed vessel was added acetonitrile (9 L) and the solvent was sparged with nitrogen for 2 hours. To the solvent was added cesium fluoride (335.8 g, 2.21 moles), 4-(tributylstannyl)pyridazine (408 g, 1.11 moles), 4-trifluoromethyl-6-iodophenol (318.33 g, 1.11 moles), palladium tetrakis triphenylphosphine (61.31 g, 53.05 mmole) and copper (I) iodide (40 g, 210 mmol) at 20° C. The resulting orange suspension was heated to 45-50° C. for 2 hours. The reaction was cooled and partitioned between ter-tbutylmethylether (2×5 L) and 2N (aq) HCl (2×5 L). The resulting biphasic solution was filtered and the layers separated. The aqueous phases were combined and basified with 4M (aq) sodium hydroxide solution (6 L) to obtain a pH=4-5. The resulting suspension was extracted into ethyl acetate (10 L) and the organic layer concentrated to dryness to afford the title compound (204 g, 60%) as an orange solid.

LCMS Rt=1.44 minutes MS m/z 241 [MH]+

$^1$H NMR (400 MHz, $d_6$-DMSO): δ 7.20 (d, 1H), 7.65 (d-d, 1H), 7.80 (s, 1H), 7.90 (m, 1H), 9.25 (d, 1H), 9.50 (s, 1H), 11.10 (s, 1H)

PREPARATION 50 tert-butyl 5-chloro-4-[4-chloro-3-(trifluoromethyl) phenoxy]-2-fluorobenzoate

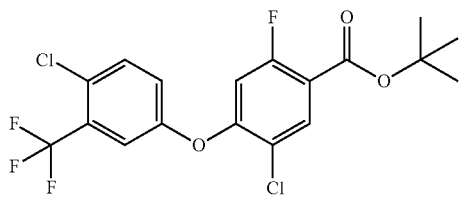 [SMILES: CC(C)(C)OC(=O)c1cc(Cl)c(Oc2ccc(Cl)c(C(F)(F)F)c2)cc1F]

To a stirred solution of tert-butyl 5-chloro-2,4-difluorobenzoate (Preparation 51, 200 mg, 0.80 mmol) in DMSO (4 mL) was added $K_2CO_3$ (333 mg, 2.41 mmol) followed by 4-chloro-3-(trifluoromethyl)phenol (190 mg, 0.97 mmol) and the reaction stirred at room temperature for 18 h. Water (10 mL) and EtOAc (15 mL) were added and the layers separated. The aqueous layer was extracted with EtOAc (15 mL). The combined organic extracts were washed with brine (15 mL),

PREPARATION 51 tert-butyl 5-chloro-2,4-difluorobenzoate

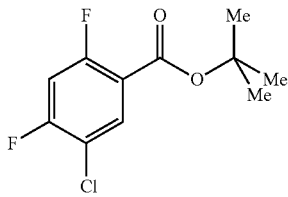

5-chloro-2,4-difluorobenzoic acid (190 g, 986.8 mol) and N,N-dimethylpyridin-4-amine (12.05 g, 0.0986 mol) were dissolved tert-butanol (1 L). Di-tert-butyl dicarbonate (445 g, 2.039 mol) was added and the reaction heated to 50° C. for 16 hours. The solvent was concentrated in vacuo and the crude was taken up in ethyl acetate (300 mL). The organic layer was washed subsequently with a solution of hydrochloric acid (1M, 300 mL), aqueous brine (2×150 mL) and an aqueous solution of saturated sodium hydrogen carbonate. The organic layer was collected, dried over sodium sulfate, filtered and concentrated in vacuo to give title compound as a dark orange oil (243 g, 99%).

$^1$H NMR (400 MHz; CDCl$_3$): δ 1.61 (s, 9H), 6.97 (dd, 1H), 7.96 (dd, 1H)

LC Rt=7.032 minutes.

PREPARATION 52

2,5-difluoro-4-(2-methoxy-5-fluorophenoxy)benzonitrile

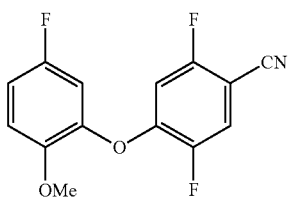 [SMILES: COc1ccc(F)cc1Oc1cc(F)c(C#N)cc1F]

To a solution of 2-methoxy-5-fluorophenol (226 mg, 1.59 mmol) in dimethylsulfoxide (10 mL) was added 2,4,5-trifluorobenzonitrile (250 mg, 1.59 mmol) and potassium carbonate (220 mg, 1.59 mmol) This suspension was stirred for 18 hours at room temperature. The reaction mixture was poured in saturated aqueous ammonium chloride solution (20 mL), and extracted with dichloromethane (3×40 mL). The combined organic layers were dried over sodium sulphate, and evaporated to afford the title compound as a clear oil (444 mg, 100%). This was used in the next reaction with no further purification.

LCMS Rt: 3.32 minutes MS m/z 280 [MH]$^+$

PREPARATION 53

2,5-difluoro-4-(2-methoxy-5-fluorophenoxy)benzamide

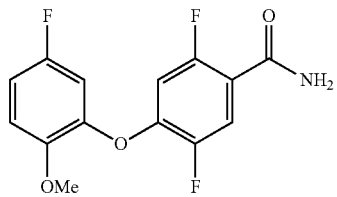 [SMILES: COc1ccc(F)cc1Oc1cc(F)c(C(N)=O)cc1F]

To a solution of 2,5-difluoro-4-(2-methoxy-5-fluorophenoxy)benzonitrile (Preparation 52, 444 mg, 1.59 mmol) in dimethylsulfoxide (10 mL) was added potassium carbonate (440 mg, 3.18 mmol), and hydrogen peroxide (commercial 30% solution, 0.95 mL, 9.49 mmol) This suspension was stirred for 3 hours at room temperature. The reaction mixture was then quenched with saturated aqueous potassium bisulphate solution (20 mL), and the precipitated solid filtered off to afford the title compound (499 mg, 100%). This was used in the next step with no further purification.

LCMS Rt: 3.32 minutes MS m/z 298 [MH]$^+$

PREPARATION 54

2-methoxy-4-(trifluoromethoxy)phenol

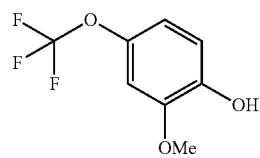 [SMILES: COc1cc(OC(F)(F)F)ccc1O]

To a solution of 2-methoxy-4-(trifluoromethoxy)benzaldehyde (1.0 g, 4.542 mmol) in dichloromethane (15 mL) was added m-chloroperoxybenzoic acid (2.04 g, 9.08 mmol). The resulting clear solution was stirred for 16 hours at room temperature. A white precipitate had formed and this was filtered off. The filtrate was evaporated to a white solid, which was diluted with ethyl acetate (25 mL) and washed with saturated aqueous sodium bicarbonate. The organic layer was dried over sodium sulphate, and evaporated to a white solid. This solid was redissolved in methanol (15 mL), and treated with triethylamine (2 mL, 10 mmol). After stirring for two hours, the solvents were evaporated. The residue was taken up in ethyl acetate (25 mL), and washed with 1N citric acid solution (20 mL) and brine (20 mL) dried over sodium sulphate, and evaporated to an oil. This crude material was then purified by eluting through a short pad of silica with dichloromethane, which afforded the title compound as a clear oil (650 mg, 57%)

$^1$H NMR (400 MHz, CDCl$_3$): δ 3.90 (s, 3H), 6.70-6.80 (m, 2H), 6.90 (d, 1H).

LCMS Rt: 2.24 minutes MS m/z 207 [M-H]$^-$

--- dried (MgSO$_4$) filtered and the solvent removed under reduced pressure to give the title compound (245 mg, 72%) as a solid.

$^1$H NMR (CDCl$_3$, 400 MHz): δ 1.58 (9H, s), 6.66 (1H, d), 7.14 (1H, dd), 7.36 (1H, d), 7.54 (1H, d) and 8.00 (1H, d).

PREPARATION 55

2,5-difluoro-4-(2-methoxy-4-(trifluoromethoxy)phenoxy)benzonitrile

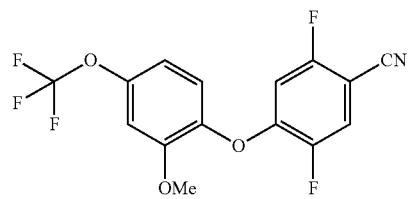 [SMILES: COc1cc(OC(F)(F)F)ccc1Oc1cc(F)c(C#N)cc1F]

To a solution of 2-methoxy-4-(trifluoromethoxy)phenol (Preparation 54, 331 mg, 1.59 mmol) in dimethylsulfoxide (10 mL) was added 2,4,5-trifluorobenzonitrile (250 mg, 1.59 mmol) and potassium carbonate (220 mg, 1.59 mmol) This suspension was stirred for 18 hours at room temperature. The reaction mixture was quenched with saturated aqueous ammonium chloride solution (20 mL), and extracted with dichloromethane (3×40 mL). The combined organic layers were dried over sodium sulphate, filtered and evaporated to afford the title compound as a clear oil (549 mg, 100%). This was used in the next reaction with no further purification.

LCMS Rt: 3.45 minutes MS m/z 346 [MH]$^+$

PREPARATION 56

2,5-difluoro-4-(2-methoxy-4-(trifluoromethoxy)phenoxy)benzamide

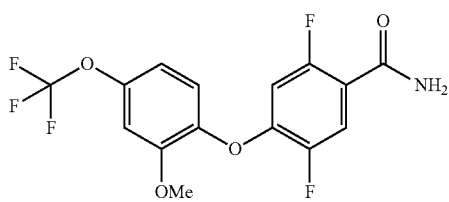 [SMILES: COc1cc(OC(F)(F)F)ccc1Oc1cc(F)c(C(N)=O)cc1F]

To a solution of 2-methoxy-4-(trifluoromethoxy)phenoxy)benzonitrile (Preparation 55, 549 mg, 1.59 mmol) in dimethylsulfoxide (6 mL) was added potassium carbonate (440 mg, 3.18 mmol), and hydrogen peroxide (commercial 30% solution, 1.08 mL, 9.54 mmol) This suspension was stirred for 3 hours at room temperature. The reaction was quenched with a saturated aqueous potassium bisulphate solution (20 mL), and the mixture extracted with ethyl acetate (25 mL). The organic layer was separated, washed with brine (20 mL), dried over magnesium sulphate, filtered and evaporated to afford the title compound (552 mg, 100%). This was used in the next step with no further purification.

LCMS Rt: 3.11 minutes MS m/z 364 [MH]$^+$

PREPARATION 57

4-{4-[1-methyl-3-(trifluoromethyl)-1H-pyrazol-5-yl]phenoxy}benzoic acid

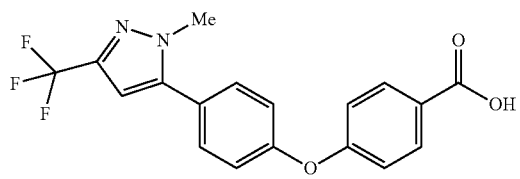 [SMILES: Cn1nc(C(F)(F)F)cc1-c1ccc(Oc2ccc(C(=O)O)cc2)cc1]

A suspension of 4-(4-iodophenoxy)benzoic acid (Preparation 143, 470 mg, 1.38 mmol), 1-methyl-3-trifluoromethylpyrazole-5-boronic acid (322 mg, 1.66 mmol), palladium tetrakis triphenyl phosphine (239 mg, 0.207 mmol) and cesium carbonate (1.35 g, 4.15 mmol) in dioxane/water (10 mL/5 mL) was heated to 80° C. for 6 hours then left to stir at room temperature overnight. The reaction was quenched by the addition of 1N HCl and extracted into ethyl acetate. The organic layer was collected, dried over magnesium sulfate and concentrated in vacuo to furnish the crude title compound that was taken on directly to the next step.

PREPARATION 58

4-[4-(1H-imidazol-1-yl)phenoxy]benzoic acid

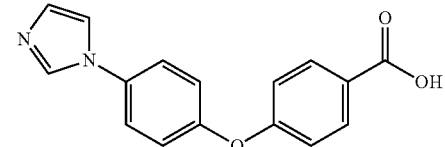

4-[4-(1H-imidazol-1-yl)phenoxy]benzoic acid can be prepared according to Preparations 1 and 2 using 4-(imidazol-1-yl)phenol and methyl-4-fluorobenzoate.

The following Preparations were prepared by the method described for Preparation 20, using appropriate reagents and conditions.

| Prep | Name | Data |
|---|---|---|
| 59 | 3-cyano-4-(2-ethyl-4-fluorophenoxy)benzoic acid | $^1$H NMR (400 MHz; CDCl$_3$): δ 1.14-1.24 (m, 3H), 2.50-2.59 (m, 2H), 6.65-6.73 (m, 1H), 6.92-7.08 (m, 3H), 8.09-8.17 (m, 1H), 8.20 (s, 1H). |
| 60 | 4-(3,4-dichlorophenoxy)-3-(trifluoromethyl)benzoic acid | $^1$H NMR (400 MHz; d$_6$-DMSO): δ 7.19 (m, 1H), 7.65 (m, 1H), 7.72 (m, 1H), 8.19 (m, 2H), 8.28 (m, 1H). |

-continued

| Prep | Name | Data |
|---|---|---|
| 61 | 3-cyano-4-(3,4-dichlorophenoxy)benzoic acid | $^1$H NMR (400 MHz; d$_6$-DMSO): δ 7.10 (d, 1 H) 7.32 (d, 1 H) 7.72 (d, 1 H) 7.78 (d, 1 H) 8.12-8.18 (m, 1 H) 8.36 (d, 1 H). |

The following preparations were prepared by the method described for Preparation 38, using appropriate reagents and conditions.

| Prep | Name | Data |
|---|---|---|
| 62 | tert-butyl 2,3,4-trifluorobenzoate | $^1$H NMR (400 MHz; CDCl$_3$): δ 1.50 (s, 9H), 7.35 (m, 1H), 7.67 (m, 1H). |

The following Preparations were prepared by the method described for preparation 50, using appropriate reagents and conditions.

| Prep | Name | Data |
|---|---|---|
| 63 | tert-butyl 4-(4-chloro-3-(trifluoromethyl)phenoxy)-2,3,6-trifluorobenzoate | $^1$H NMR (400 MHz; CDCl$_3$): δ 1.39 (s, 9H), 6.54 (m, 1H), 7.14 (m, 1H), 7.38 (s, 1H), 7.51 (d, 1H). |
| 64 | tert-butyl 4-(4-chloro-3-(trifluoromethyl)phenoxy)-2,6-difluorobenzoate | LCMS Rt = 4.22 minutes. No mass ion seen. |
| 65 | tert-butyl 4-(4-chloro-3-(trifluoromethyl)phenoxy)-2,3-difluorobenzoate | $^1$H NMR (400 MHz; CDCl$_3$): δ 1.60 (s, 9H), 6.80 (m, 1H), 7.17 (m, 1H), 7.40 (m, 1H), 7.50 (d, 1H), 7.65 (m, 1H). |
| 66 | tert-butyl 4-(3-chloro-4-(trifluoromethyl)phenoxy)-2,5-difluorobenzoate | — |

The following preparations were prepared by the method described for preparation 32, using appropriate reagents and conditions.

| Prep | Name | Data |
|---|---|---|
| 67 | 4-(4-chloro-3-(trifluoromethyl)phenoxy)-2,3,6-trifluorobenzoic acid | $^1$H NMR (400 MHz; CD$_3$OD): δ 6.82 (m, 1H), 7.26 (m, 1H), 7.43 (d, 1H), 7.61 (d, 1H). |
| 68 | 4-(4-chloro-3-(trifluoromethyl)phenoxy)-2,6-difluorobenzoic acid | LCMS Rt = 3.70 minutes MS m/z 353 [M H]+ |
| 69 | 4-(4-chloro-3-(trifluoromethyl)phenoxy)-2,3-difluorobenzoic acid | $^1$H NMR (400 MHz; CDCl$_3$): δ 6.80 (m, 1H), 7.20 (m, 1H), 7.43 (m, 1H), 7.57 (d, 1H), 7.80 (m, 1H). |
| 70 | 4-(3-chloro-4-(trifluoromethyl)phenoxy)-2,5-difluorobenzoic acid | $^1$H NMR (400 MHz; d$_6$-DMSO): δ 7.25 (m, 1H), 7.42 (m, 1H), 7.59 (m, 1H), 7.85 (m, 2H), 13.55 (br s, 1H). |

The following preparations were prepared by the method described for Preparation 3, using appropriate reagents and conditions.

| Prep | Name | Data |
|---|---|---|
| 71 | 4-methylphenyl 5-chloro-4-[3-chloro-4-(difluoromethoxy)phenoxy]-2-fluorobenzoate | $^1$H NMR (400 MHz; d6-DMSO): δ 2.34 (s, 3 H), 7.08-7.30 (m, 7 H), 7.45-7.49 (m, 1 H), 7.57 (d, 1 H), 8.26 (d, 1 H). |

-continued

| Prep | Name | Data |
|---|---|---|
| 72 | 4-methylphenyl 4-[3-chloro-4-(difluoromethoxy)phenoxy]-2,5-difluorobenzoate | $^1$H NMR (400 MHz; d6-DMSO): δ 2.34 (s, 3 H), 7.08-7.30 (m, 7 H), 7.44-7.48 (m, 1 H), 7.58 (d, 1 H), 8.09 (d, 1 H). |
| 73 | 4-methylphenyl 5-chloro-4-[4-chloro-3-(difluoromethoxy)phenoxy]-2-fluorobenzoate | LCMS Rt = 1.77 minutes<br>MS m/z 457 [MH]+ |
| 74 | 4-methylphenyl 4-[4-chloro-3-(difluoromethoxy)phenoxy]-2,5-difluorobenzoate | LCMS Rt = 1.76 minutes<br>MS m/z 441 [MH]+ |

The following preparations were prepared by to the method described for Preparation 46 or Preparation 53, using appropriate reagents and conditions.

| Prep | Name | Data |
|---|---|---|
| 75 | 4-(3,4-dichlorophenoxy)-3-methylbenzamide | $^1$H NMR (400 MHz; d$_6$-DMSO): δ 2.20 (s, 3H), 6.95 (m, 1H), 7.00 (m, 1H), 7.25 (m, 1H), 7.30 (br s, 1H), 7.60 (m, 1H), 7.75 (m, 1H), 7.85 (m, 1H), 7.90 (br s, 1H) |
| 76 | 3-chloro-4-(3,4-dichlorophenoxy)benzamide | $^1$H NMR (400 MHz; d$^6$-DMSO): δ 7.02 (m, 1H), 7.20 (m, 1H), 7.40 (m, 1H), 7.50 (br s, 1H), 7.65 (m, 1H), 7.88 (m, 1H), 8.08 (br s, 1H), 8.10 (m, 1H) |
| 77 | 2,5-difluoro-4-(2-methoxy-5-trifluoromethoxyphenoxy)benzamide | LCMS Rt = 2.76 minutes MS m/z 364 [MH]$^+$. |
| 78 | 4-(5-chloro-2-methoxyphenoxy)-2,5-difluorobenzamide | $^1$H NMR (400 MHz, CDCl$_3$): δ 3.80 (s, 3H), 5.70 (br. s, 1H), 6.50 (dd, 1H), 6.57 (br. s, 1H), 6.96 (d, 1H), 7.10 (d, 1H), 7.22 (dd, 1H), 7.94 (dd, 1H). |
| 79 | 4-(4-chlorophenoxy)-3-iodo-benzamide | $^1$H NMR (400 MHz; d$^6$-DMSO): δ 7.00 (d, 1H), 7.03 (d, 2H), 7.42 (br. s, 1H), 7.46 (d, 2H), 7.89 (br. s, 1H), 8.03 (br. s, 1H), 8.41 (d, 1H). |
| 80 | 2,5-difluoro-4-(5-trifluoromethyl-2-methoxyphenoxy)benzamide | $^1$H NMR (400 MHz, CDCl$_3$): δ 3.87 (s, 3H), 5.74 (br. s, 1H), 6.48 (dd, 1H), 6.58 (br. s, 1H), 7.11 (d, 1H), 7.37 (d, 1H), 7.53 (dd, 1H), 7.95 (dd, 1H). |
| 81 | 2,5-difluoro-4-(4-fluoro-2-methoxyphenoxy)benzamide | $^1$H NMR (400 MHz, CDCl$_3$): δ 3.80 (s, 3H), 5.71 (br. s, 1H), 6.40 (dd, 1H), 6.56 (br. s, 1H), 6.70 (ddd, 1H), 6.77 (dd, 1H), 7.09 (dd, 1H), 7.92 (dd, 1H). |
| 82 | 4-(4,5-dichloro-2-methoxyphenoxy)-2,5-difluorobenzamide | $^1$H NMR (400 MHz, DMSO-d$_6$): δ 3.80 (s, 3H), 6.85 (dd, 1H), 7.49 (s, 1H), 7.52 (s, 1H), 7.60-7.75 (m, 3H). |
| 83 | 2,5-difluoro-4-(4-fluoro-2,3-dihydrobenzofuran-7-yloxy)benzamide | $^1$H NMR (400 MHz, DMSO-d$_6$): δ 3.29 (t, 2H), 4.64 (t, 2H), 6.69-6.76 (m, 2H), 7.05 (dd, 1H), 7.58-7.65 (m, 3H). |
| 84 | 4-(4-chloro-2-(trifluoromethoxy)phenoxy)-2,5-difluorobenzamide | $^1$H NMR (400 MHz, DMSO-d$_6$): δ 7.21 (dd, 1H), 7.32 (d, 1H), 7.54 (dd, 1H), 7.67-7.79 (m, 4H). |
| 85 | 2,5-difluoro-4-(2-methoxy-4-(trifluoromethyl)phenoxy)benzamide | LCMS Rt = 3.73 minutes<br>MS m/z 348 [MH]$^+$ |
| 86 | 4-(4-chloro-3-(trifluoromethyl)phenoxy)-3,5-difluorobenzamide | $^1$H NMR (400 MHz; MeOD): δ 7.17 (dd, 1H), 7.39 (s, 1H), 7.57 (d, 1H), 7.72 (d, 2H). |
| 87 | 4-(4-chloro-3-(trifluoromethyl)phenoxy)-2,5-difluorobenzamide | $^1$H NMR (400 MHz; d$_6$-DMSO): δ 7.30 (m, 1H), 7.40 (m, 1H), 7.60 (m, 1H), 7.75 (m, 2H). |
| 88 | 4-(4-chloro-3-(trifluoromethyl)phenoxy)-2-ethylbenzamide | $^1$H NMR (400 MHz; d$_6$-DMSO): δ 1.18 (t, 3H), 2.76 (q, 2H), 6.90 (m, 1H), 7.00 (s, 1H), 7.30 (br-s, 2H), 7.40 (d, 1H), 7.45 (m, 1H), 7.75 (d, 2H). |
| 89 | 4-(4-chloro-2-(1-methyl-1H-pyrazol-5-yl)phenoxy)benzamide | $^1$H NMR (400 MHz; d$_6$-DMSO): δ 3.75 (s, 3H), 6.30 (m, 1H), 6.95 (m, 2H), 7.15 (m, 1H), 7.30 (m, 1H), 7.40 (m, 1H), 7.60 (m, 2H), 7.80 (m, 2H), 7.90 (m, 1H). |
| 90 | 4-(2-(pyridazin-4-yl)-4-(trifluoromethyl)phenoxy)benzamide | $^1$H NMR (400 MHz; d$_6$-DMSO): δ 7.20 (m, 3H), 7.40 (m, 1H), 7.90-8.00 (m, 5H), 8.05 (m, 1H), 9.30 (m, 1H), 9.50 (m, 1H). |

-continued

| Prep | Name | Data |
|---|---|---|
| 91 | 4-(4-chloro-3-(trifluoromethyl)phenoxy)-2-(trifluoromethyl)benzamide | $^1$H NMR (400 MHz, CDCl$_3$): δ 5.85 (m, 2H), 7.15 (m, 2H), 7.32 (m, 1H), 7.38 (m, 1H), 7.55 (m, 1H), 7.65 (m, 1H). |
| 92 | 2-chloro-4-(4-chloro-3-(trifluoromethyl)phenoxy)-5-fluorobenzamide | $^1$H NMR (400 MHz, CDCl$_3$): δ 5.92 (s, 1H), 6.51 (s, 1H), 7.10 (m, 2H), 7.37 (m, 1H), 7.50 (m, 1H), 7.80 (m, 1H). |
| 93 | 4-(4-chloro-3-(trifluoromethyl)phenoxy)-3-fluoro-2-methoxybenzamide | $^1$H NMR (400 MHz, CDCl$_3$): δ 4.10 (m, 3H), 5.81 (s, 1H), 6.83 (m, 1H), 7.12 (m, 1H), 7.37 (m, 1H), 7.49 (m, 1H), 7.61 (s, 1H), 7.95 (m, 1H) |
| 94 | 4-(4-chloro-3-(trifluoromethyl)phenoxy)-2-methoxybenzamide | $^1$H NMR (400 MHz; d$_6$-acetone): δ 4.00 (s, 3H), 6.73 (dd, 1H), 6.94 (d, 2H), 7.38 (dd, 1H), 7.52 (d, 1H), 7.70 (d, 1H), 8.12 (d, 1H). |

The following Preparations were prepared by the method described for Preparation 19, using appropriate reagents and conditions.

| Prep | Name | Data |
|---|---|---|
| 95 | 2,5-difluoro-4-(2-methoxy-5-(trifluoromethoxy)phenoxy)benzonitrile | LCMS Rt = 3.78 minutes<br>MS m/z 346 [MH]+ |
| 96 | 4-(5-chloro-2-methoxyphenoxy)-2,5-difluorobenzonitrile | $^1$H NMR (400 MHz, CDCl$_3$): δ 3.79 (s, 3H), 6.50 (dd, 1H), 6.97 (d, 1H), 7.14 (d, 1H), 7.26 (dd, 1H), 7.40 (dd, 1H). |
| 97 | 4-(4-chlorophenoxy)-3-iodobenzonitrile | $^1$H NMR (400 MHz, CDCl$_3$): δ 6.76 (d, 1H), 7.00 (d, 2H), 7.39 (d, 2H), 7.54 (dd, 1H), 8.14 (d, 1H). |
| 98 | 2,5-difluoro-4-(2-methoxy-5-(trifluoromethyl)phenoxy)benzonitrile | $^1$H NMR (400 MHz, CDCl$_3$): δ 3.86 (s, 3H), 6.48 (dd, 1H), 7.12 (d, 1H), 7.39-7.43 (m, 2H), 7.58 (dd, 1H). |
| 99 | 2,5-difluoro-4-(4-fluoro-2-methoxyphenoxy)benzonitrile | $^1$H NMR (400 MHz, CDCl$_3$): δ 3.79 (s, 3H), 6.43 (dd, 1H), 6.72 (ddd, 1H), 6.78 (dd, 1H), 7.10 (dd, 1H), 7.38 (dd, 1H). |
| 100 | 4-(4,5-dichloro-2-methoxyphenoxy)-2,5-difluorobenzonitrile | $^1$H NMR (400 MHz, CDCl$_3$): δ 3.85 (s, 3H), 6.51 (dd, 1H), 7.10 (s, 1H), 7.23 (s, 1H), 7.40 (dd, 1H). |
| 101 | 2,5-difluoro-4-(4-fluoro-2,3-dihydrobenzofuran-7-yloxy)benzonitrile | $^1$H NMR (400 MHz, DMSO-d$_6$): δ 3.30 (t, 2H), 4.66 (t, 2H), 6.77 (dd, 1H), 6.99 (dd, 1H), 7.13 (dd, 1H), 8.13 (dd, 1H). |
| 102 | 4-(4-chloro-2-(trifluoromethoxy)phenoxy)-2,5-difluorobenzonitrile | $^1$H NMR (400 MHz, CDCl$_3$): δ 6.66 (dd, 1H), 7.13 (dd, 1H), 7.37 (dd, 1H), 7.43-7.48 (m, 2H). |
| 103 | 4-[4-chloro-2-(trifluoromethoxy)phenoxy]-2-methoxybenzonitrile | $^1$HNMR (400 MHz, CDCl$_3$): δ 3.89 (s, 3H), 6.44 (dd, 1H), 6.58 (d, 1H), 7.10 (d, 1H), 7.33 (dd, 1H), 7.39-7.42 (m, 1H), 7.49 (d, 1H). |
| 104 | 2,5-difluoro-4-(2-methoxy-4-(trifluoromethyl)phenoxy)benzonitrile | LCMS Rt = 3.73 minutes<br>MS m/z 330 [MH]$^+$ |
| 105 | 4-(4-chloro-2-methoxyphenoxy)-2-methoxybenzonitrile | LCMS Rt = 1.76 minutes<br>MS m/z 290 [MH]+.<br>$^1$HNMR (400 MHz, CDCl$_3$): δ 3.79 (s, 3H), 3.86 (s, 3H), 6.36 (dd, 1H), 6.54 (d, 1H), 6.95-7.04 (m, 3H), 7.42 (d, 1H). |
| 106 | 4-(4-chloro-3-(trifluoromethyl)phenoxy)-3,5-difluorobenzonitrile | $^1$H NMR (400 MHz; CDCl$_3$): δ 7.00-7.08 (m, 1H), 7.31 (s, 1H), 7.37-7.43 (m, 2H), 7.47 (d, 1H). |
| 107 | 4-(4-chloro-3-(trifluoromethyl)phenoxy)-2,5-difluorobenzonitrile | $^1$H NMR (400 MHz; CDCl$_3$): δ 7.45 (m, 1H), 7.55 (m, 1H), 7.74 (m, 1H), 7.81 (m, 1H), 8.25 (m, 1H). |
| 108 | 4-(4-chloro-3-(trifluoromethyl)phenoxy)-2-ethylbenzonitrile | $^1$H NMR (400 MHz; d$_6$-DMSO): δ 1.20 (m, 3H), 2.80 (q, 2H), 7.00 (m, 1H), 7.20 (m, 1H), 7.40 (m, 1H), 7.60 (, m, 1H), 7.80 (m, 2H). |
| 109 | 4-(2-(pyridazin-4-yl)-4-(trifluoromethyl)phenoxy)benzonitrile | $^1$H NMR (400 MHz; d$_6$-DMSO): δ 7.20 (m, 2H), 7.35 (m, 1H), 7.75 (m, 2H), 7.90 (m, 1H), 7.95 (m, 1H), 8.05 (m, 1H), 9.20 (m, 1H), 9.50 (m, 1H). |

| Prep | Name | Data |
|---|---|---|
| 110 | 4-(4-chloro-2-(1-methyl-1H-pyrazol-5-yl)phenoxy)benzonitrile | $^1$H NMR (400 MHz; d$_6$-DMSO): δ 3.70 (s, 3H), 6.20 (m, 1H), 7.00 (m, 2H), 7.30 (m, 1H), 7.35 (m, 1H), 7.60 (m, 2H), 7.75 (m, 2H). |
| 111 | 4-(4-chloro-3-(trifluoromethyl)phenoxy)-2-(trifluoromethyl)benzonitrile | $^1$H NMR (400 MHz, CDCl$_3$): δ 7.17 (m, 2H), 7.35 (m, 1H), 7.45 (m, 1H), 7.59 (m, 1H), 7.81 (m, 1H) |
| 112 | 2-chloro-4-(4-chloro-3-(trifluoromethyl)phenoxy)-5-fluorobenzonitrile. | $^1$H NMR (400 MHz, CDCl$_3$): δ 7.08 (m, 1H), 7.15 (m, 1H), 7.40 (m, 1H), 7.55 (m, 2H) |
| 113 | 4-(4-chloro-3-(trifluoromethyl)phenoxy)-3-fluoro-2-methoxybenzonitrile | $^1$H NMR (400 MHz, CDCl$_3$): δ 4.18 (m, 3H), 6.68 (m, 1H), 7.15 (m, 1H), 7.33 (m, 1H), 7.38 (m, 1H), 7.51 (m, 1H) |
| 114 | 4-(4-chloro-3-(trifluoromethyl)phenoxy)-2-methoxybenzonitrile | LCMS Rt = 3.64 minutes MS m/z 350 [MNa]+ |

The following Preparations were prepared by the method described for Preparation 17, using appropriate reagents and conditions.

| Prep | Name | Data |
|---|---|---|
| 115 | 4-[4-chloro-3-(trifluoromethyl)phenoxy]-3-methoxybenzaldehyde | $^1$H NMR (400 MHz; CDCl$_3$): δ 3.90 (s, 3H), 7.05-7.12 (m, 2H), 7.32 (br s, 1H), 7.43-7.50 (m, 2H), 7.55 (s, 1H), 9.97 (s, 1H). |
| 116 | 4-[4-chloro-3-(trifluoromethyl)phenoxy]-5-fluoro-2-methoxybenzaldehyde | $^1$H NMR (400 MHz; d$_6$-DMSO): δ 3.85 (s, 3H), 7.03-7.05 (d, 1H), 7.31-7.34 (d-d, 1H), 7.56-7.57 (d, 1H), 7.64-7.74 (m, 2H), 10.04 (d, 1H). |
| 117 | 4-(4-chloro-2-methoxyphenoxy)-5-fluoro-2-methoxybenzaldehyde | $^1$H NMR (400 MHz; d$_6$-DMSO): δ 3.76 (s, 3H), 3.79 (s, 3H), 6.48-6.50 (d, 1H), 7.02-7.04 (m, 1H), 7.14-7.16 (d, 1H), 7.28 (d, 1H), 7.53-7.56 (d, 1H), 10.21 (d, 1H). |
| 118 | 2-[4-chloro-3-(trifluoromethyl)phenoxy]-5-formylbenzonitrile | $^1$H NMR (400 MHz; (CDCl$_3$): δ 6.96-6.99 (d, 1H), 7.28-7.31 (m, 1H), 7.51 (d, 1H), 7.62-7.64 (d, 1H), 8.04-8.06 (m, 1H), 8.24 (m, 1H), 9.97 (d, 1H). |
| 119 | 2-(4-chloro-2-methoxyphenoxy)-5-formylbenzonitrile | $^1$H NMR (400 MHz; (CDCl$_3$): δ 3.77 (s, 3H), 6.75-6.77 (m, 1H), 7.01-7.04 (m, 2H), 7.12-7.14 (m, 1H), 7.93-7.96 (m, 1H), 8.17-8.18 (d, 1H), 9.92 (d, 1H). |
| 120 | 4-(4-chloro-2-methoxyphenoxy)-2-fluorobenzaldehyde | $^1$H NMR (400 MHz; (CDCl$_3$): δ 3.80 (s, 3H), 6.57-6.60 (dd, 1H), 6.75-6.78 (m, 1H), 6.99-7.09 (m, 3H), 7.80-7.84 (dd, 1H), 10.23 (d, 1H) |
| 121 | 4-(4-chloro-2-methoxyphenoxy)-3-fluorobenzaldehyde | $^1$H NMR (400 MHz; (CDCl$_3$): δ 3.80 (s, 3H), 6.80-6.85 (m, 1H), 6.97-7.06 (m, 3H), 7.53-7.56 (m, 1H), 7.68-7.72 (m, 1H), 9.89 (d, 1H). |

The following preparations were prepared by the method described for Preparation 1, using appropriate reagents and conditions.

| Prep | Name | Data |
|---|---|---|
| 122 | Methyl 3-bromo-4-(4-chlorophenoxy)benzoate | — |
| 123 | Methyl 3-chloro-4-(4-fluorophenoxy)benzoate | — |
| 124 | methyl 4-(3,4-dichlorophenoxy)-2-fluorobenzoate | — |
| 125 | methyl 4-[3-(trifluoromethoxy)phenoxy]benzoate | LCMS Rt = 3.21 minutes MS m/z 313 [MH]+, 311 [M − H]−. |
| 126 | methyl 4-[4-chloro-3-(trifluoromethyl)phenoxy]-3-fluorobenzoate | $^1$H NMR (400 MHz; CDCl$_3$): δ 3.95 (s, 3 H) 7.08-7.13 (m, 2 H) 7.36 (d, 1 H) 7.49 (d, 1 H) 7.84-7.88 (m, 1 H) 7.88-7.92 (m, 1 H). |

-continued

| Prep | Name | Data |
|---|---|---|
| 127 | methyl 2-chloro-4-[4-chloro-3-(trifluoromethyl)phenoxy] benzoate | $^1$H NMR (400 MHz; CDCl$_3$): δ 3.94 (s, 3 H) 6.91 (d, 1 H) 7.07 (d, 1 H) 7.17 (d, 1 H) 7.41 (d, 1 H) 7.53 (d, 1 H) 7.91 (d, 1 H). |
| 128 | methyl 3-chloro-4-[4-chloro-3-(trifluoromethyl)phenoxy] benzoate | $^1$H NMR (400 MHz; CDCl$_3$): δ 3.94 (s, 3 H) 7.00 (d, 1 H) 7.09 (d, 1 H) 7.35 (d, 1 H) 7.50 (d, 1 H) 7.95 (d, 1 H) 8.19 (d, 1 H). |
| 129 | methyl 4-(2-ethyl-4-fluorophenoxy)benzoate | LCMS Rt = 3.29 minutes MS m/z 275 [MH]+ |
| 130 | methyl 4-(4-chloro-2-methoxyphenoxy)-2,5-difluorobenzoate | $^1$H NMR (d6-DMSO 400 MHz): δ 3.76 (s, 3H), 3.81 (s, 3H), 6.68 (dd, 1H), 7.07 (dd, 1H), 7.26 (d, 1H), 7.31 (d, 1H), 7.80 (dd, 1H). |
| 131 | ethyl 5-chloro-4-[4-chloro-2-(difluoromethoxy)phenoxy]-2-fluorobenzoate | $^1$H NMR (400 MHz; d$_6$-DMSO): δ 1.28 (t, 3H), 4.28 (q, 2H), 6.90 (d, 1H), 7.08-7.25-7.42 (t, 1H), 7.38-7.45 (m, 2H), 7.58 (s, 1H), 8.00 (d, 1H). |

The following Preparations were prepared by the method described for Preparation 2 or 8, using appropriate reagents and conditions.

| Prep | Name | Data |
|---|---|---|
| 132 | 4-(2-ethyl-4-fluorophenoxy)-2-fluorobenzoic acid | LCMS Rt = 3.28 minutes MS m/z 277 [M − H]− |
| 133 | 4-(2-ethyl-4-fluorophenoxy)-3-fluorobenzoic acid | $^1$H NMR (400 MHz; d$^6$-DMSO): δ 1.10 (m, 3H), 2.53 (m, 2H), 6.81 (m, 1H), 7.08 (m, 2H), 7.23 (m, 1H), 7.70 (m, 1H), 7.80 (m, 1H), 13.10 (br s, 1H) |
| 134 | 4-(3,4-dichlorophenoxy)-2,5-difluorobenzoic acid | LCMS Rt = 3.14 minutes MS m/z 317 [M − H]− |
| 135 | 3-bromo-4-(4-chlorophenoxy)benzoic acid | — |
| 136 | 3-chloro-4-(4-fluorophenoxy)benzoic acid | — |
| 137 | 4-(3,4-dichlorophenoxy)-2-fluorobenzoic acid | $^1$H NMR (400 MHz; CD$_3$OD): δ 6.80-6.89 (m, 2H), 7.02-7.08 (m, 1H), 7.30-7.32 (m, 1H), 7.56-7.60 (m, 1H), 7.92-7.99 (m, 1H). |
| 138 | 4-[3-(trifluoromethoxy)phenoxy] benzoic acid | LCMS Rt = 2.53 minutes MS m/z 297 [M − H]−. |
| 139 | 4-[4-chloro-3-(trifluoromethyl)phenoxy]-3-fluorobenzoic acid | $^1$H NMR (400 MHz; CDCl$_3$): δ 7.08-7.17 (m, 2 H) 7.39 (d, 1 H) 7.51 (d, 1 H) 7.89-7.99 (m, 2 H). |
| 140 | 2-chloro-4-[4-chloro-3-(trifluoromethyl)phenoxy]benzoic acid | $^1$H NMR (400 MHz; CDCl$_3$): δ 6.94 (d, 1 H) 7.10 (d, 1 H) 7.20 (d, 1 H) 7.43 (d, 1 H) 7.56 (d, 1 H) 8.09 (d, 1 H). |
| 141 | 3-chloro-4-[4-chloro-3-(trifluoromethyl)phenoxy]benzoic acid | $^1$H NMR (400 MHz; CDCl$_3$): δ 7.02 (d, 1 H) 7.13 (d, 1 H) 7.39 (d, 1 H) 7.52 (d, 1 H) 8.01 (d, 1 H) 8.26 (d, 1 H). |
| 142 | 4-(3,4-dichlorophenoxy)-3-fluorobenzoic acid | $^1$HNMR (d$_6$-DMSO): δ 7.15 (m, 1H), 7.24 (m, 1H), 7.5 (m, 1H), 7.68 (m, 1H), 7.80-7.89 (m, 2H), 13.3 (br s, 1H). |
| 143 | 4-(4-iodophenoxy)benzoic acid | $^1$HNMR (d$_6$-DMSO): δ 6.92 (m, 2H), 7.05 (m, 2H), 7.75 (m, 2H), 7.96 (m, 2H). |
| 144 | 4-(4-chloro-2-methoxyphenoxy)-2,5-difluorobenzoic acid | $^1$HNMR (400 MHz, d$_6$-DMSO): δ 3.77 (s, 3H), 6.64 (dd, 1H), 7.06 (dd, 1H), 7.24 (d, 1H), 7.31 (d, 1H), 7.76 (dd, 1H), 13.31-13.37 (br. s, 1H) |
| 145 | 4-(2-ethyl-4-fluorophenoxy)benzoic acid | $^1$HNMR (d$_6$-DMSO): δ 1.05 (t, 3H), 2.50 (q, 2H), 6.90 (m, 2H), 7.12 (m, 2H), 7.23 (m, 1H), 7.90 (m, 2H). |

The following Preparation was prepared by the method described for Preparation 28, using appropriate reagents and conditions.

| Prep | Name | Data |
|---|---|---|
| 146 | 4-(4-chloro-2-methoxyphenoxy)-2-methoxybenzoic acid | ¹HNMR (400 MHz, CDCl₃): δ 3.79 (s, 3H), 4.02 (s, 3H), 6.46 (dd, J = 8.79, 2.34 Hz, 1H), 6.65 (d, J = 2.34 Hz, 1H), 6.95-7.05 (m, 3H), 8.07 (d, J = 8.79 Hz, 1H) |

PREPARATION 147

4-Methylphenyl-5-chloro-4-[4-chloro-3-(trifluoromethoxy)phenoxy]-2-fluorobenzoate

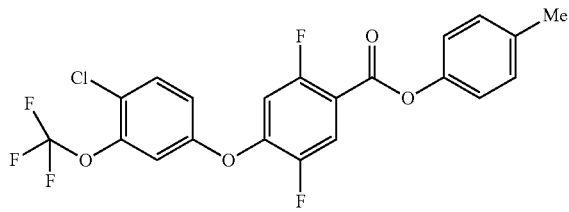 [SMILES: Cc1ccc(OC(=O)c2cc(F)c(Oc3ccc(Cl)c(OC(F)(F)F)c3)cc2F)cc1]

Prepared according to the method described for Preparation 11 using 4-chloro-3-trifluoromethoxyphenol and 4-methylphenyl-5-chloro-2,4-difluorobenzoate (Preparation 10).

LCMS Rt=1.75 minutes. No mass ion detected.

¹HNMR (d₆-DMSO): δ 2.30 (s, 3H), 7.15 (m, 2H), 7.20-7.30 (m, 4H), 7.50 (m, 1H), 7.78 (m, 1H), 8.25 (m, 1H).

PREPARATION 148

4-(3,4-Dichlorobenzyl)benzoic acid

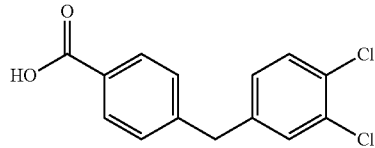 [SMILES: O=C(O)c1ccc(Cc2ccc(Cl)c(Cl)c2)cc1]

To a solution of ethyl 4-(3,4-dichlorobenzyl)benzoate (Preparation 170, 240 mg, 0.78 mmol) in THF/MeOH/water (4:3:2, 7.2 mL) was added lithium hydroxide (65 mg, 1.56 mmol) and the mixture was stirred at room temperature for 4 hours. The solvent was evaporated in vacuo and the residue acidified with 1M hydrochloric acid solution. The crude product was extracted with chloroform/methanol, and the extract dried over Na₂SO₄ and the solvent evaporated in vacuo to give the title compound as a white solid (160 mg, 73%)

LCMS Rt=3.05 minutes, MS m/z 279 [M-H]−

¹HNMR (400 MHz, DMSO): δ 4.03 (s, 2H), 7.25 (d, 1H), 7.37 (d, 2H), 7.55 (m, 2H), 7.87 (d, 2H), 12.84 (br s, 1H).

PREPARATION 149

Ethyl 4-[3-(trifluoromethoxy)benzyl]benzoate

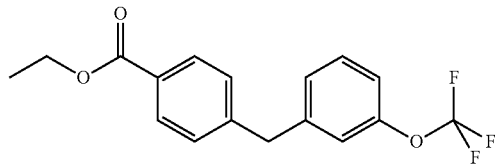 [SMILES: CCOC(=O)c1ccc(Cc2cccc(OC(F)(F)F)c2)cc1]

A mixture of zinc (807 mg, 12.3 mmol) and lithium chloride (523 mg, 12.3 mmol) under argon was warmed for 10 minutes using a hot air gun, allowed to cool and then anhydrous THF (50 mL) added. The zinc was activated by treatment with 1,2-dibromoethane (39 mg, 0.21 mmol) and TMSCl (4.3 mg, 0.04 mmol). To the resulting mixture at 25° C. was added ethyl 4-(bromomethyl)benzoate (1.0 g, 4.15 mmol) and the mixture stirred for 15 minutes. 3-(Trifluoromethoxy)bromobenzene (694 mg, 2.88 mmol) was added, followed by (1,3-bis(2,6-diisopropylphenyl)imidazolidene)(3-chloropyridyl)palladium(II) dichloride [PEPPSI™-SIPr] (28 mg, 0.04 mmol) and the mixture stirred at 25° C. for 1 hour. Saturated ammonium chloride solution was added and the crude product extracted with ether. The ether extract was washed with brine, dried over Na₂SO₄ and the solvent evaporated in vacuo. The crude product was purified by silica gel column chromatography eluting with 7:3 hexane:ethyl acetate to afford the title compound (950 mg, 71%).

LCMS Rt=3.98 minutes, MS m/z 325 [MH]+

¹HNMR (400 MHz, CDCl₃): δ 1.37 (t, 3H), 4.03 (s, 2H), 4.33-4.38 (m, 2H), 7.01 (s, 1H), 7.07 (m, 2H), 7.24-7.30 (m, 3H), 7.97 (d, 2H).

PREPARATION 150

4-[3-(Trifluoromethoxy)benzyl]benzoic acid

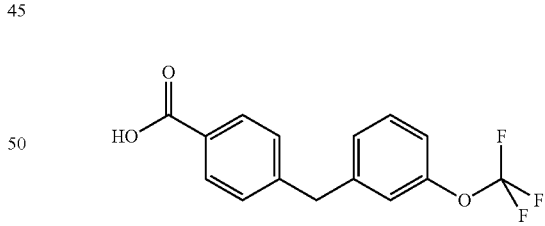

To a solution of ethyl 4-[3-(trifluoromethoxy)benzyl]benzoate (Preparation 149, 950 mg, 2.93 mmol) in THF/MeOH/water (4:3:2, 27 mL) was added lithium hydroxide (246 mg, 5.86 mmol) and the mixture was stirred at room temperature for 4 hours. The mixture was concentrated in vacuo and acidified with 1M hydrochloric acid solution. The resulting precipitate was filtered off and dried to give the title compound as a white solid (600 mg, 69%).

LCMS Rt=3.51 minutes, MS m/z 297 [MH]+

¹HNMR (400 MHz, DMSO): δ 4.08 (s, 2H), 7.19 (d, 1H), 7.25-7.30 (m, 2H), 7.37 (d, 2H), 7.43 (t, 1H), 7.88 (d, 2H), 12.83 (br s, 1H).

PREPARATION 151

4-[(3,4-Dichlorophenyl)sulfanyl]benzoic acid

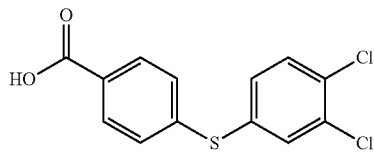

To a stirred solution of methyl 4-fluorobenzoate (2.0 g, 11.9 mmol) in dimethylformamide (5 mL) was added 3,4-dichlothiophenol (1.29 g, 11.8 mmol) and caesium carbonate (3.9 g, 12.0 mmol). The reaction mixture was heated at 50° C. for 16 hours, then diluted with water (50 mL) and extracted with ethyl acetate (3×50 mL). The extracts were combined, washed with water (50 mL), brine (50 mL), dried over $Na_2SO_4$ and evaporated in vacuo to give the title compound (500 mg, 14%) which was used without further purification.

LCMS Rt=3.08 minutes, MS m/z 297 [M-H]−

$^1$HNMR (400 MHz, DMSO): δ 7.33-7.40 (m, 3H), 7.68-7.73 (m, 2H), 7.89-7.92 (d, 2H), 13.05 (br s, 1H).

PREPARATION 152

4-{[3-(Trifluoromethyl)phenyl]sulfanyl}benzoic acid

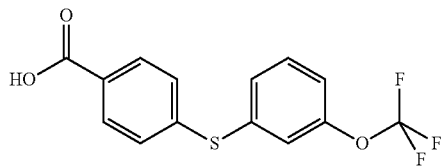 [SMILES: O=C(O)c1ccc(Cc2cccc(OC(F)(F)F)c2)cc1]

To a stirred solution of methyl 4-fluorobenzoate (500 mg, 3.24 mmol) in dimethylformamide (5 mL) was added 3-trifluoromethoxythiophenol (565 mg, 2.91 mmol) and caesium carbonate (1.38 g, 4.24 mmol). The reaction mixture was heated at 80° C. for 18 hours, then diluted with water (30 mL) and extracted with ethyl acetate (3×30 mL). The extracts were combined, washed with water (3×30 mL), brine (2×30 mL), dried over $Na_2SO_4$ and evaporated in vacuo. The crude product was purified by silica gel column chromatography eluting with hexane:ethyl acetate (0-20%) to afford the title compound (300 mg, 35%).

LCMS Rt=3.74 minutes, MS m/z 315 [MH]+

PREPARATION 153

3-chloro-4-(4-chloro-3-(trifluoromethyl)phenoxy)-2-fluorobenzoic acid

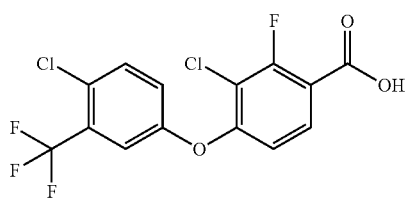 [SMILES: O=C(O)c1ccc(Oc2ccc(Cl)c(C(F)(F)F)c2)c(Cl)c1F]

tert-Butyl 3-chloro-2,4-difluorobenzoate (Preparation 154, 0.249 g, 1.00 mmol), 4-chloro-3-(trifluoromethyl)phenol (0.196 g, 1.00 mmol) and potassium carbonate (210 mg, 1.5 mmol) were added to dimethyl sulfoxide (6 mL) and stirred at ambient temperature for 4 hours, then another 18 hours at 70° C. The reaction mixture was diluted with water and extracted three times with ethyl ether. The combined organic phase was dried over anhydrous magnesium sulfate and the solvent removed in vacuo to leave a residue. The residue was purified by silica gel column chromatography eluting with 0-10% ethyl acetate in hexanes. The desired fractions were combined and the solvent removed in vacuo. The residue was dissolved in trifluoroacetic acid (0.50 mL, 6.5 mmol) and stirred for 18 hours. The solvent was removed in vacuo and the residue triturated with dichloromethane. The resulting precipitate was collected by filtration and vacuum dried to afford the title compound as a white solid (140 mg).

$^1$HNMR (400 MHz, DMSO): δ 7.00 (dd, 1H), 7.49 (dd, 1H), 7.73 (d, 1H), 7.79-7.89 (m, 2H), 13.52 (s, 1H).

LCMS Rt=1.43 minutes MS m/z 368 [M-H]−

PREPARATION 154 tert-butyl 3-chloro-2,4-difluorobenzoate

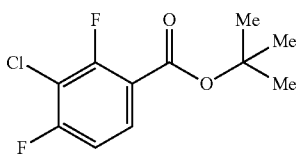 [SMILES: CC(C)(C)OC(=O)c1ccc(F)c(Cl)c1F]

di-tert-butyldicarbonate (1.64 g, 7.50 mmol) was added to a 10° C. solution of 3-chloro-2,4-difluorobenzoic acid (0.963 g, 5.00 mmol), triethylamine (2.09 mL, 15.0 mmol) and 4-dimethylaminopyridine (0.220 g, 1.80 mmol) in dichloromethane (9.3 mL). The reaction mixture was stirred at room temperature for 2 hours then diluted with water and extracted two times with dichloromethane. The organic phases were combined and the solvent removed in vacuo. The product was purified by silica gel column chromatography eluting with 0-20% hexanes to ethyl acetate to afford the title compound as a colorless oil (0.554 g).

$^1$HNMR (400 MHz, DMSO): δ 1.59 (s, 9H), 7.01 (m, 1H), 7.81 (m, 1H).

LCMS Rt=1.34 minutes MS m/z 249 [MH]+

PREPARATION 155

4-(3,4-dichlorobenzyl)-3-methoxybenzamide

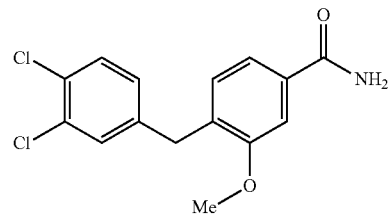 [SMILES: COc1cc(C(N)=O)ccc1Cc1ccc(Cl)c(Cl)c1]

To a solution of 4-((3,4-dichlorophenyl)(hydroxy)methyl)-3-methoxybenzamide (Preparation 156, 142 mg, 0.435 mmol) in DCM (5 mL) was added TFA (0.065 mL, 0.870 mmol) followed by triethylsilane (0.083 mL, 0.522 mmol)

and the reaction stirred at room temperature for 72 hours. Further TFA (0.065 mL, 0.870 mmol) and triethylsilane (0.083 mL, 0.522 mmol) were added and the reaction stirred for a further 24 hours. The reaction was partitioned between saturated aq. NH₄Cl (20 mL), and EtOAc (20 mL). The layers were separated and the aqueous was extracted with EtOAc (2×20 mL). The combined organics were washed with brine (20 mL), dried over MgSO₄, filtered and the solvent removed in vacuo to give a white solid (165 mg, 100%). The material was used as crude in the next reaction without further purification.

LCMS Rt=3.05 minutes, MS m/z 310 [MH]+

¹HNMR (400 MHz, d₆-DMSO): δ 3.80 (s, 3H), 3.90 (s, 2H), 7.00 (m, 1H), 7.19 (m, 2H), 7.45 (m, 1H), 7.50 (m, 1H), 7.72 (m, 1H), 7.80 (m, 2H)

PREPARATION 156

4-((3,4-dichlorophenyl)(hydroxy)methyl)-3-methoxybenzamide

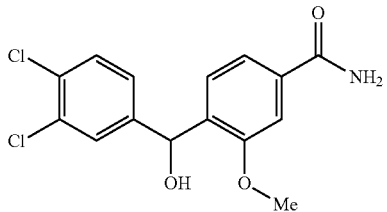 [SMILES: COc1cc(C(N)=O)ccc1C(O)c1ccc(Cl)c(Cl)c1]

To a solution of 4-((3,4-dichlorophenyl)(hydroxy)methyl)-3-methoxybenzonitrile (165 mg, 0.535 mmol) in DMSO (3 mL) was added K₂CO₃ (222 mg, 1.60 mmol) followed by 30% H₂O₂ (1210 mg, 10.7 mmol) and the reaction was stirred at room temperature. After 45 minutes the product was purified without workup by direct injection onto a reverse phase column (Biotage C18-silica 12 g) eluting with 100:0: 0.1 H₂O:MeCN:HCO₂H, to 0:100:0.1. The title compound was collected as a white solid (142 mg, 81%).

LCMS Rt=2.67 minutes MS m/z 326 [MH]+

¹HNMR (400 MHz, d₆-DMSO): δ 3.80 (s, 3H), 5.98 (m, 1H), 6.01 (m, 1H), 7.00 (m, 1H), 7.15 (br s, 1H), 7.28 (m, 1H), 7.55 (m, 2H), 7.80 (m, 1H), 7.83 (br s, 1H), 8.02 (m, 1H).

PREPARATION 157

4-((3,4-dichlorophenyl)(hydroxy)methyl)-3-methoxybenzonitrile

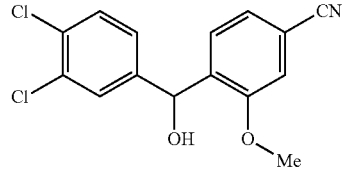 [SMILES: COc1cc(C#N)ccc1C(O)c1ccc(Cl)c(Cl)c1]

To a solution of 4-bromo-3-methoxybenzonitrile (606 mg, 2.86 mmol) in dry THF (10 mL) was added iso-propylmagnesium chloride (2 M in diethylether, 1.54 mL, 3.09 mmol) slowly via microsyringe. To the reaction mixture was added 3,4-dichlorobenzaldehyde (270 mg, 1.54 mmol) in dry THF (1 mL) via syringe. After 1 hour at room temperature saturated aqueous NH₄Cl (20 mL) was added and the mixture extracted with EtOAc (3×20 mL). The combined organics were concentrated in vacuo and taken through to the next step as crude.

PREPARATION 158 tert-butyl 5-chloro-4-(3,4-dichlorophenylthio)-2-fluorobenzoate

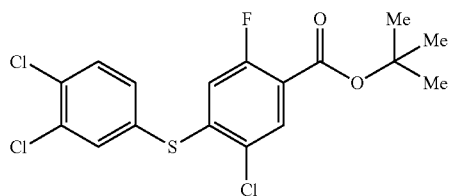 [SMILES: CC(C)(C)OC(=O)c1cc(Cl)c(Sc2ccc(Cl)c(Cl)c2)cc1F]

tert-butyl 5-chloro-2,4-difluorobenzoate (Preparation 160, 416 mg, 1.68 mmol) was added to a mixture of potassium carbonate (694 mg, 5.02 mmol), 3,4-dichlorothiophenol (300 mg, 1.77 mmol) in DMSO (16.7 mL) and the reaction stirred at room temperature for 18 hours. The reaction was quenched by addition of 0.5 N aqueous NaOH (20 mL) and EtOAc (30 mL) and the mixture partitioned. The aqueous was further extracted with EtOAc (3×10 mL), the organics combined, washed with brine (10 mL), dried (MgSO₄), filtered and evaporated to give a yellow solid. Silica gel column chromatography eluting with 9:1 DCM:heptanes resulted in isolation of the title compound as a white solid (571 mg, 83%).

LCMS Rt=4.54 minutes, no mass ion

¹H-NMR (400 MHz, CDCl₃): δ 1.57 (s, 9H), 6.51 (d, 1H), 7.35 (dd, 1H), 7.54 (d, 1H), 7.62 (d, 1H), 7.84 (d, 1H).

PREPARATION 159

5-chloro-4-(3,4-dichlorophenylthio)-2-fluorobenzoic acid

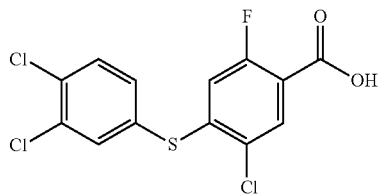 [SMILES: O=C(O)c1cc(Cl)c(Sc2ccc(Cl)c(Cl)c2)cc1F]

Trifluoroacetic acid (1.04 mL, 14 mmol) was added to a mixture of tert-butyl 5-chloro-4-(3,4-dichlorophenylthio)-2-fluorobenzoate (571 mg, 1.40 mmol) in DCM (10 mL) and the reaction stirred at room temperature for 18 hours. The reaction was concentrated to dryness to give the title compound as a white solid (492 mg, 100%). No further purification.

LCMS Rt=3.13 minutes, 351 [MH]+

¹H-NMR (400 MHz, CDCl₃): δ 6.49 (d, 1H), 7.40 (dd, 1H), 7.59 (d, 1H), 7.67 (d, 1H), 8.00 (d, 1H).

PREPARATION 160

Tert-butyl 5-chloro-2,4-difluorobenzoate

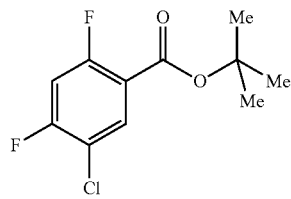 [SMILES: CC(C)(C)OC(=O)c1cc(Cl)c(F)cc1F]

5-chloro-2,4-difluorobenzoic acid (190 g, 986.8 mol) and N,N-dimethylpyridin-4-amine (12.05 g, 0.0986 mol) were dissolved tert-butanol (1 L). Di-tert-butyl dicarbonate (445 g, 2.039 mol) was added and the reaction heated to 50° C. for 16 hours. The solvent was concentrated in vacuo and the crude was taken up in ethyl acetate (300 mL). The organic layer was washed subsequently with a solution of hydrochloric acid (1M, 300 mL), aqueous brine (2×150 mL) and an aqueous solution of saturated sodium hydrogen carbonate. The organic layer was collected, dried over sodium sulfate, filtered and concentrated in vacuo to give title compound as a dark orange oil (243 g, 99%).

$^1$H NMR (400 MHz; CDCl$_3$): δ 1.61 (s, 9H), 6.97 (dd, 1H), 7.96 (dd, 1H)

LC Rt=7.032 minutes.

PREPARATION 161

Tert-butyl 5-chloro-4-[3-chloro-4-(trifluoromethoxy)phenoxy]-2-fluorobenzoate

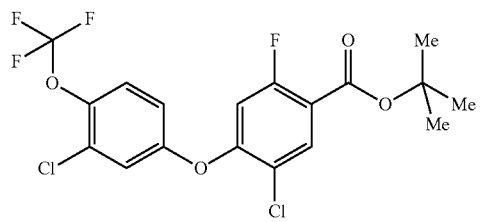 [SMILES: CC(C)(C)OC(=O)c1cc(Cl)c(Oc2ccc(OC(F)(F)F)c(Cl)c2)cc1F]

3-chloro-4-(trifluoromethoxy)phenol (22.6 g, 0.106 mol) and tert-butyl 5-chloro-2,4-difluorobenzoate (Preparation 51, 26.4 g, 0.106 mol) were dissolved in dimethylsulfoxide (105 mL). Then potassium carbonate (29.4 g, 0.213 mol) was added portionwise to the mixture, which was stirred at room temperature for 18 hours. The reaction mixture was dropped into iced water (500 mL) and stirred vigorously for 4 hours. The resulting solid was collected by filtration then taken up in isopropanol (75 mL) and water (15 mL). The reaction was heated to 55° C., then cooled down to room temperature. The resulting solid was collected by filtration to yield the title compound as an off-white white solid (35.3 g, 75%).

$^1$H NMR (400 MHz; CDCl$_3$): δ 1.62 (s, 9H), 6.72 (d, 1H), 6.97 (dd, 1H), 7.16 (d, 1H), 7.35-7.38 (m, 1H), 8.02 (d, 1H)

LC Rt=8.637 minutes.

PREPARATION 162

5-chloro-4-[3-chloro-4-(trifluoromethoxy)phenoxy]-2-fluorobenzoic acid

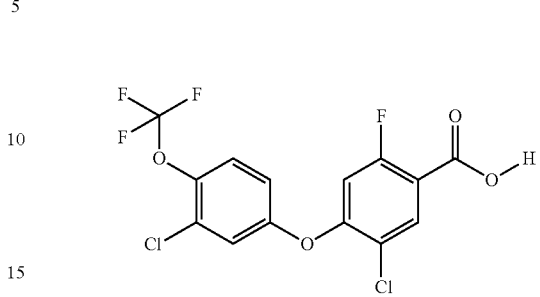

Tert-butyl 5-chloro-4-[3-chloro-4-(trifluoromethoxy)phenoxy]-2-fluorobenzoate (Preparation 161, 41.88 g, 0.0868 mol) was dissolved in dichloromethane (75 mL), then trifluoroacetic acid (21.2 mL, 0.285 mol) was added and the mixture was stirred at room temperature for 50 hours. Trifluoroacetic acid was added again (1.2 mL, 0.017 mol) and the reaction left to stir for 4 hours. A solid was observed in the flask, so it was collected by filtration. The filtrate was concentrated in vacuo and dichloromethane (5 mL) was added to the crude, which was stirred for 5 minutes at room temperature. The resulting solid was collected by filtration and set aside. The crops were combined and title compound was isolated as a white solid (29.6 g, 81%).

$^1$H NMR (400 MHz; CDCl$_3$): δ 6.72 (d, 1H), 7.04 (dd, 1H), 7.23-7.25 (m, 1H), 7.40-7.43 (m, 1H), 8.19 (d, 1H)

LC Rt=6.782 minutes.

PREPARATION 163

4-methylphenyl 5-chloro-4-[4-chloro-3-(trifluoromethyl)phenoxy]-2-fluorobenzoate

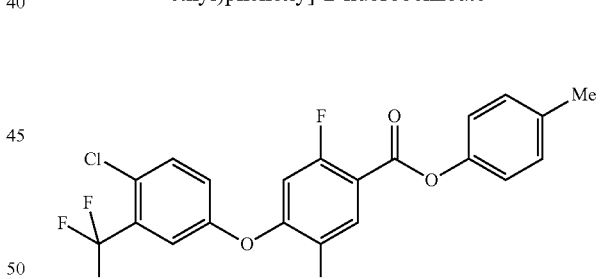

To a solution of 4-methylphenyl 5-chloro-2,4-difluorobenzoate (Preparation 10, 39.0 g, 137.97 mmol) and 4-chloro-3-(trifluoromethyl)phenol (27.12 g, 137.97 mmol) in DMSO (197 mL) was added potassium carbonate (47.67 g, 344.92 mmol) portion wise maintaining the internal at 15-25° C. with a cold water jacket. The reaction mixture was stirred at room temperature for 2 hours, cold water charged and the resulting slurry stirred for 20 minutes. The mixture was filtered, washed with water and dried to give the title compound as a pale yellow solid (56.4 g, 90%).

HPLC Rt=8.446 minutes $^1$H NMR (400 MHz; CDCl$_3$): δ 2.39 (s, 3H), 6.72 (d, 1H), 7.17-7.26 (m, 3H), 7.11 (s, 2H), 7.44 (s, 1H), 7.58 (d, 1H), 8.26 (d, 1H)

PREPARATION 164

4-(Bromomethyl)-5-chloro-2-fluoro-N-(methylsulfonyl)benzamide

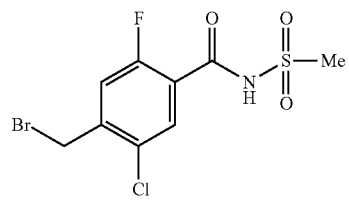 [SMILES: CS(=O)(=O)NC(=O)c1cc(Cl)c(CBr)cc1F]

To a suspension of 5-chloro-2-fluoro-4-methyl-N-(methylsulfonyl)benzamide (Preparation 165, 118 g, 0.45 mol) in 1,2-dichloroethane (1.25 L) was added N-bromosuccinimide (91 g, 0.51 mol) and benzoyl peroxide (5 g, 20 mmol) and the mixture heated to reflux for 18 hours. N-bromosuccinimide (30 g, 0.17 mol) was then added and the solution heated 24 hours more. A further portion of N-bromosuccinimide (20 g, 0.11 mol) was added and the solution heated for 3 hours, then cooled and washed with water (1 L) containing aqueous sodium thiosulphate solution (200 mL, 0.5 M). The organic layer was washed with water (500 mL), dried over sodium sulphate and concentrated in vacuo to yield a crude solid. To a solution of this crude solid in EtOAc (1 L) was added diisopropylethylamine (130 mL, 0.75 mol) and diethyl phosphite (27.6 g, 0.2 mol) and the mixture stirred for 5 hours under nitrogen, then washed with aqueous hydrochloric acid (1 L, 2 M), dried over magnesium sulphate and evaporated to yield a dark solid. Trituration with diethyl ether (200 mL) gave the first crop of title compound as a tan solid (68 g). The filtrate was purified by silica gel chromatography eluting with 10% EtOAc in DCM containing acetic acid (1%), followed by crystallization from acetonitrile (130 mL) to yield the second crop of the title compound (30 g):

$^1$H NMR (400 MHz, CDCl$_3$): δ 3.41 (s, 3H), 4.54 (s, 2H), 7.38 (d, 1H), 8.14 (d, 1H), 8.78 (br, 1H).

PREPARATION 165

5-Chloro-2-fluoro-4-methyl-N-(methylsulfonyl)benzamide

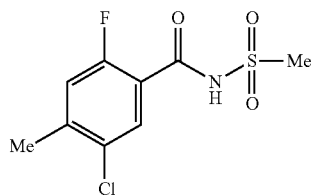 [SMILES: Cc1cc(F)c(C(=O)NS(C)(=O)=O)cc1Cl]

To 5-chloro-2-fluoro-4-methylbenzoic acid (200 g, 1.06 mol) in DCM (1.4 L) was added methanesulphonamide (152 g, 1.6 mol), 4-(dimethylamino)pyridine (183 g 1.6 mol) and N-(3-dimethylaminopropyl)-N'-ethylcarbodiimide hydrochloride (306 g, 1.6 mol). The reaction mixture spontaneously heated at 30° C. over 30 minutes, then it was stirred at room temperature for 18 hours under a nitrogen atmosphere. The reaction was washed with aqueous hydrochloric acid (4 M, 0.8 L). The organic layer was separated, washed with water (500 mL), dried over sodium sulphate and concentrated in vacuo to yield a tan solid, which was recrystallised from hot EtOAc (0.9 L) by addition of n-heptane (100 mL) and cooling to yield the title compound (118 g, 45%).

$^1$H NMR (400 MHz, CDCl$_3$): δ 2.42 (s, 3H), 3.42 (s, 3H), 7.10 (d, 1H), 8.05 (d, 1H), 8.78 (br, 1H).

PREPARATION 166

4-(4-chloro-3-(trifluoromethyl)phenoxy)-2-methoxy-benzaldehyde

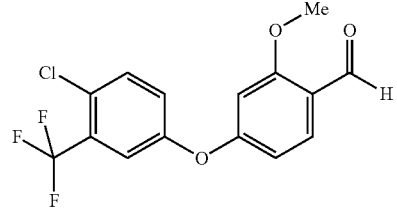 [SMILES: COc1cc(Oc2ccc(Cl)c(C(F)(F)F)c2)ccc1C=O]

A solution of 4-chloro-3-(trifluoromethyl)phenol (0.383 g, 1.95 mmol) and 4-fluoro-2-methoxybenzaldehyde (0.300 g, 1.95 mmol) in DMSO (5 mL) was prepared. Potassium carbonate (0.538 g, 3.90 mmol) was added and the reaction mixture was heated at 80-° C. for 18 hours. The reaction was cooled to room temperature, diluted with ethyl acetate (30 mL) and washed with water (3×60 mL). The organic layer was dried over magnesium sulfate and the filtrate was concentrated in vacuo to give the title product as a cream solid (0.479 g, 74%).

LCMS Rt=3.62 minutes MS m/z 331 [MH]$^+$ $^1$HNMR (400 MHz, CDCl$_3$): δ 3.85 (s, 3H), 6.45 (d, 1H), 6.55 (s, 1H), 7.10 (d, 1H), 7.35 (s, 1H), 7.45 (d, 1H), 7.80 (d, 1H), 10.30 (s, 1H).

PREPARATION 167

4-methyl phenyl 5-chloro-4-[3-chloro-4-(trifluoromethoxy)phenoxy]-2-fluorobenzoate

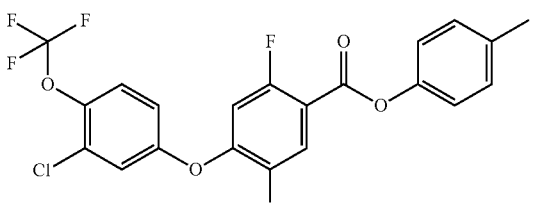

4-Methylphenyl-5-chloro-2,4-difluorobenzoate (Preparation 10, 133 mg, 0.47 mmol) was added to a mixture of potassium carbonate (84 mg, 0.61 mmol), 3-chloro-4-(trifluoromethoxy)phenol (100 mg, 0.47 mmol) in dimethylsulfoxide (1.0 mL) and the reaction stirred at room temperature for 3 hours. The reaction was diluted by addition of water (2.0 mL) and ethyl acetate (3.0 mL) and the mixture partitioned. The aqueous was further extracted with ethyl acetate (3.0 mL), the organics combined, dried with magnesium sulfate, filtered and evaporated to give a white solid. Purification was accomplished by column chromatography on silica, eluting with ethyl acetate:heptanes (3:97) to provide the title compound as a white solid (106 mg, 47%).

LCMS Rt=6.15 minutes, no mass ion.

$^1$H-NMR (400 MHz, CDCl$_3$): δ 2.37 (s, 3H), 6.75 (d, 1H), 7.01 (dd, 1H), 7.00 (d, 2H), 7.23-7.21 (m, 3H), 7.38 (d, 1H), 8.42 (d, 1H)

$^{19}$F-NMR (400 MHz, CDCl$_3$): 6-58.1, -104.9

PREPARATION 168

2,5-Difluoro-4-hydroxy-N-(methylsulfonyl)benzamide

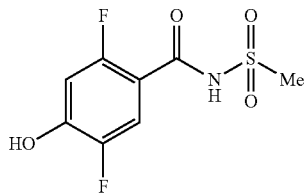 [SMILES: CS(=O)(=O)NC(=O)c1cc(F)c(O)cc1F]

Hydrochloric acid solution in dioxane (4 M, 30 mL) was added to the 4-tert-butoxy-2,5-difluoro-N-(methylsulfonyl)benzamide (Preparation 35, 1.76 g, 5.73 mmol) and the resulting solution stirred at room temperature. After 3 hours the reaction mixture was concentrated in vacuo and the residue azeotroped repeatedly with DCM to yield the title compound as a white solid (1.49 g, 100%).

$^1$H NMR (400 MHz; CDCl$_3$): δ 3.25 (s, 3H), 6.60-6.68 (m, 1H), 7.45-7.55 (m, 1H), 9.80-9.95 (br, 1H), 10.50-10.65 (br, 1H)

LCMS Rt=0.72 minutes. MS m/z 250 [M-H]$^-$, 252 [MH]$^+$

PREPARATION 169

4-tert-butoxy-2,5-difluoro-N-(methylsulfonyl)benzamide

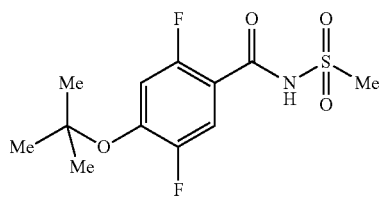 [SMILES: CC(C)(C)Oc1cc(F)c(C(=O)NS(C)(=O)=O)cc1F]

Potassium tert-butoxide (1.46 g, 13.0 mmol) was added to a solution of 2,4,5-trifluoro-N-(methylsulfonyl)benzamide (Preparation 7, 1.5 g, 5.924 mmol) in DMSO (10 mL) and stirred at room temperature. After 3 hours, potassium tert-butoxide (140 mg, 1.3 mmol) was further added and stirred for 18 hours more. The reaction mixture was diluted with EtOAc and 10% aqueous citric acid solution. The pH of the water layer was acidic. The organic layer was washed with more 10% aqueous citric acid and brine, then dried over magnesium sulfate, filtered and concentrated in vacuo to yield the title compound as a cream solid (1.76 g, 100%).

$^1$H NMR (400 MHz; CDCl$_3$): δ 1.45 (s, 9H), 3.42 (s, 3H), 6.88-6.93 (m, 1H), 7.80-7.87 (m, 1H), 8.70-8.85 (br, 1H).

PREPARATION 170

Ethyl 4-(3,4-dichlorobenzyl)benzoate

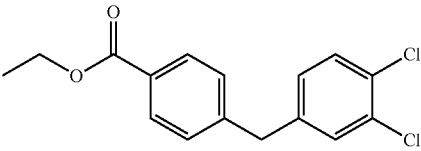 [SMILES: CCOC(=O)c1ccc(Cc2ccc(Cl)c(Cl)c2)cc1]

A mixture of zinc (404 mg, 6.17 mmol) and lithium chloride (261 mg, 6.17 mmol) under argon was warmed for 15 minutes using a hot air gun, allowed to cool and then anhydrous THF (20 mL) added. The zinc was activated by treatment with 1,2-dibromoethane (19 mg, 0.10 mmol) and TMSCl (2.2 mg, 0.02 mmol). To the resulting mixture at 25° C. was added ethyl 4-(bromomethyl)benzoate (500 mg, 2.06 mmol) and the mixture stirred for 15 minutes. A solution of 3,4-dichloro-iodobenzene (392 mg, 1.44 mmol) in anhydrous THF (5 mL) was added, followed by (1,3-bis(2,6-diisopropylphenyl)imidazolidene)(3-chloropyridyl)palladium(II) dichloride [PEPPSI™-SIP] (14 mg, 0.02 mmol) and the mixture stirred at 25° C. for 1 hour. Saturated ammonium chloride solution was added and the crude product extracted with ether. The ether extract was washed with brine, dried over Na$_2$SO$_4$ and the solvent evaporated in vacuo. The crude product was purified by silica gel column chromatography eluting with 7:3 hexane:ethyl acetate to afford the title compound (240 mg, 38%).

LCMS Rt=4.12 minutes, MS m/z 309 [MH]+

$^1$HNMR (400 MHz, CDCl$_3$): δ 1.37 (t, 3H), 3.97 (s, 2H), 4.33-4.38 (m, 2H), 6.99 (d, 1H), 7.20-7.25 (m, 3H), 7.34 (d, 1H), 7.97 (d, 2H).

The ability of the compounds of formula (I) to block the Nav1.7 (or SCN9A) channel was measured using the assays described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 μg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 μg/ml G-418 in an incubator at 37° C. with a humidified atmosphere of 10% CO$_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM CaCl$_2$, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" (EIC$_{50}$) values were calculated from single point electrophysiology data by the following equation, (tested concentration, uM)×(100-% inhibition/% inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of 1×10$^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays were also conducted using the Ionworks Quattro automated electrophysiological platform (Molecular Devices Corp). Intracellular and extracellular solutions were as described above with the following changes, 100 µg/ml amphotericin was added to the intracellular solution to perforate the membrane and allow electrical access to the cells. hSCN9A cells were grown and harvested as for PatchXpress and cells were resuspended in extracellular solution at a concentration of 3–4×10$^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assays described above and found to have the Nav1.7 EIC$_{50}$ (µM) values specified in the table below. All data are derived from the PatchXpress assay unless explicitly stated otherwise.

| Ex. | EIC$_{50}$ |
|---|---|
| 1 | 0.81 |
| 2 | 0.064 |
| 3 | 1.7 |
| 4 | 0.25 |
| 5 | 0.20 |
| 6 | 0.49 |
| 7 | 0.025 |
| 8 | 0.035 |
| 9 | 0.047 |
| 10 | 0.97 |
| 11 | 0.43 |
| 12 | 10 |
| 13 | 2.5 |
| 14 | 0.85 |
| 15 | 0.93 |
| 16 | 0.040 |
| 17 | 0.032 |
| 18 | 0.37 |
| 19 | >1 |
| 20 | 5.4 |
| 21 | 0.45 |
| 22 | 5.2 |
| 23 | 3.4 |
| 24 | 5.7 |
| 25 | >10 |
| 26 | 0.43 |
| 27 | 0.19 |
| 28 | 0.86 |
| 29 | 0.95 |
| 30 | 0.76 |
| 31 | 5.7 |
| 32 | >1 |
| 33 | 0.50 |
| 34 | 1.5 |
| 35 | 11 |
| 36 | 3.3 |
| 37 | >3 |
| 38 | >10 |
| 39 | 9.3 |
| 40 | 25 |
| 41 | 0.66 |
| 42 | 0.59 |
| 43 | 5.8 |
| 44 | 2.0 |
| 45 | 1.1 |
| 46 | NT |
| 47 | 4.0 |
| 48 | 0.21 |
| 49 | 0.52 |
| 50 | >3 |
| 51 | 0.26 |
| 52 | 0.47 |
| 53 | 0.063 |
| 54 | 2.3 |
| 55 | 0.34 |
| 56 | 0.20 |
| 57 | 0.92 |

| Ex. | EIC$_{50}$ | | Ex. | EIC$_{50}$ |
|---|---|---|---|---|
| 58 | 0.43 | | 136 | NT |
| 59 | 4.0 | | 137 | 3.0 |
| 60 | 33 | | 138 | 6.6 |
| 61 | >10 | | 139 | NT |
| 62 | 0.89 | | 140 | NT |
| 63 | >3 | | 141 | 2.5 |
| 64 | >3 | | 142 | >3 |
| 65 | >1 | | 143 | 4.7 |
| 66 | 1.1 | | 144 | 2.3 |
| 67 | 5.0 | | 145 | 1.2 |
| 68 | 10 | | 146 | >3 |
| 69 | 6.2 | | 147 | >3 |
| 70 | 2.8 | | 148 | >1 |
| 71 | NT | | 149 | >1 |
| 72 | >1 | | 150 | NT |
| 73 | 0.71 | | 151 | 0.52 |
| 74 | >1 | | 152 | NT |
| 75 | 0.45 | | 153 | NT |
| 76 | 0.85 | | 154 | >3 |
| 77 | 0.53 | | 155 | 5.4 |
| 78 | 4.2 | | 156 | >3 |
| 79 | 4.1 | | 157 | 6.8 |
| 80 | >3 | | 158 | 0.84 |
| 81 | 0.23 | | 159 | NT |
| 82 | 0.14 | | 160 | 10 |
| 83 | >3 | | 161 | 28 |
| 84 | 0.45 | | 162 | 28 |
| 85 | >1 | | 163 | 12 |
| 86 | >1 | | 164 | >10 |
| 87 | 6.9 | | 165 | NT |
| 88 | >3 | | 166 | 17 |
| 89 | >3 | | 167 | 12 |
| 90 | >0.3 | | 168 | 1.6 |
| 91 | >3 | | 169 | 21 |
| 92 | >3 | | 170 | 1.9 |
| 93 | >1 | | 171 | >10 |
| 94 | >3 | | 172 | 16 |
| 95 | >3 | | 173 | 1.2 |
| 96 | >3 | | 174 | 20 |
| 97 | 7.0 | | 175 | >10 |
| 98 | >1 | | 176 | >10 |
| 99 | NT | | 177 | 16 |
| 100 | 1.1 | | 178 | 1.3 |
| 101 | 1.5 | | 179 | >10 |
| 102 | 3.7 | | 180 | 32 |
| 103 | 3.2 | | 181 | 1.6 |
| 104 | >3 | | 182 | 1.4 |
| 105 | >3 | | 183 | >10 |
| 106 | NT | | 184 | 24 |
| 107 | 9.3 | | 185 | 21 |
| 108 | NT | | 186 | 34 |
| 109 | >1 | | 187 | NT |
| 110 | >1 | | 188 | >10 |
| 111 | >3 | | 189 | >10 |
| 112 | >3 | | 190 | 0.93 |
| 113 | >3 | | 191 | >10 |
| 114 | NT | | 192 | 14 |
| 115 | >3 | | 193 | >10 |
| 116 | >3 | | 194 | >10 |
| 117 | NT | | 195 | 22 |
| 118 | NT | | 196 | 11 |
| 119 | NT | | 197 | >10 |
| 120 | >3 | | 198 | 1.4 |
| 121 | >1 | | 199 | 7.6 |
| 122 | 4.4 | | 200 | 8.1 |
| 123 | 2.0 | | 201 | 20 |
| 124 | 0.49 | | 202 | 6.9 |
| 125 | >3 | | 203 | 25 |
| 126 | >1 | | 204 | 21 |
| 127 | >3 | | 205 | 15 |
| 128 | 11 | | 206 | 18 |
| 129 | 1.3 | | 207 | 13.7 (IW) |
| 130 | >3 | | 208 | 18.7 (IW) |
| 131 | 3.8 | | 209 | 28.2 (IW) |
| 132 | >3 | | 210 | 288 (IW) |
| 133 | >3 | | 211 | 67 (IW) |
| 134 | >3 | | 212 | NT |
| 135 | >3 | | 213 | >3 |

| Ex. | EIC$_{50}$ |
|---|---|
| 214 | 0.22 |
| 215 | 1.3 |
| 216 | 11 |
| 217 | 4.2 |
| 218 | 2.8 |
| 219 | NT |
| 220 | 1.8 |
| 221 | 300 (IW) |
| 222 | NT |
| 223 | 2.4 |
| 224 | NT |
| 225 | 3.3 |
| 226 | 300 (IW) |
| 227 | NT |
| 228 | 5.4 |
| 229 | 1.2 |
| 230 | 0.86 |
| 231 | 3.9 |
| 232 | NT |
| 233 | 8.2 |
| 234 | 0.85 |
| 235 | 36.6 (IW) |
| 236 | NT |
| 237 | 2.5 |
| 238 | 0.96 |
| 239 | NT |
| 240 | 0.63 |
| 241 | 144 (IW) |
| 242 | NT |
| 243 | 11.9 (IW) |
| 244 | NT |
| 245 | 1.3 |
| 246 | 0.49 |
| 247 | NT |
| 248 | 1.7 |
| 249 | NT |
| 250 | 1.4 |
| 251 | NT |
| 252 | 1.2 |
| 253 | 2.5 |
| 254 | 7.5 |
| 255 | 1.4 |
| 256 | 2.8 |
| 257 | 1.1 |
| 258 | 2.1 |
| 259 | >323 (IW) |
| 260 | NT |
| 261 | 1.0 |
| 262 | 1.1 |
| 263 | NT |
| 264 | 7.0 |
| 265 | 4.8 |
| 266 | 0.27 |
| 267 | NT |
| 268 | 5.3 |
| 269 | 1.7 |
| 270 | 3.7 |
| 271 | >323 (IW) |
| 272 | 0.71 |
| 273 | 44.8 (IW) |
| 274 | 277 (IW) |
| 275 | 116 (IW) |
| 276 | NT |
| 277 | 5.6 |
| 278 | 6.6 |
| 279 | NT |
| 280 | 0.43 |
| 281 | 4.3 |
| 282 | 1.2 |
| 283 | 8.6 |
| 284 | 8.7 |
| 285 | 0.057 |
| 286 | 3.4 |
| 287 | 2.1 |
| 288 | 2.0 |
| 289 | 1.2 |
| 290 | NT |
| 291 | 0.42 |
| 292 | 0.62 |
| 293 | >3 |
| 294 | 0.16 |
| 295 | 0.097 |
| 296 | 0.39 |
| 297 | 2.3 |
| 298 | 0.20 |
| 299 | 1.0 |
| 300 | 3.91 (IW) |
| 301 | 61.7 (IW) |
| 302 | NT |
| 303 | >3 |
| 304 | 8.7 |
| 305 | 6.4 |
| 306 | 25 |
| 307 | 9.7 |
| 308 | >10 |
| 309 | 18 |
| 310 | 3.3 |
| 311 | >3 |
| 312 | 3.3 |
| 313 | 9.9 |
| 314 | 1.1 |
| 315 | 1.5 |
| 316 | 1.6 |
| 317 | 3.5 |
| 318 | 5.6 |
| 319 | 2.5 |
| 320 | 1.8 |
| 321 | 0.32 |
| 322 | >3 |
| 323 | 36 |
| 324 | >3 |
| 325 | NT |
| 326 | 4.1 |
| 327 | >323 (IW) |

IW = Ionworks assay
NT = not tested

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the EIC$_{50}$ value at the Nav1.7 channel to determine the selectivity of a given compound for Nav1.7 vs Nav1.5.

We claim:
1. A compound of formula (I):

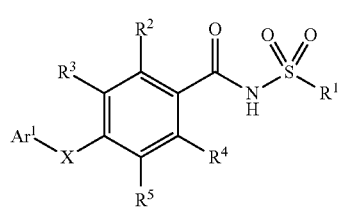

or a pharmaceutically acceptable salt thereof, wherein:
X is O, S, NH or CH$_2$;
Ar$^1$ is (i) naphthyl; or (ii) naphthyl or phenyl each of which is independently substituted by one to three Y;
Y is F; Cl; CN; (C$_1$-C$_8$)alkyl, optionally substituted by (C$_3$-C$_8$)cycloalkyl or by one to eight F; (C$_3$-C$_8$)cycloalkyl, optionally substituted by one to eight F; NR$^7$R$^8$; (C$_1$-C$_8$)alkyloxy, optionally independently substituted by one to three R$^9$ or by one to eight F;

($C_3$-$C_8$)cycloalkyloxy, wherein the ($C_3$-$C_8$)cycloalkyloxy may be optionally fused to a phenyl ring or may be independently substituted by one to three $R^{10}$; phenyl, optionally independently substituted by one to three $R^{10}$; Het$^1$ or Het$^2$;

$R^1$ is ($C_1$-$C_6$)alkyl or ($C_3$-$C_8$)cycloalkyl, each of which is optionally substituted by one to eight F;

$R^2$, $R^3$, $R^4$ are independently H, F, Cl or —OCH$_3$;

$R^5$ is H, CN, F, Cl or $R^6$;

$R^6$ is a group selected from ($C_1$-$C_6$)alkyl and ($C_1$-$C_6$)alkyloxy, wherein each group is optionally substituted by one to eight F;

$R^7$ and $R^8$ are independently H; ($C_1$-$C_8$)alkyl, optionally independently substituted by one to three $R^{11}$; ($C_3$-$C_8$)cycloalkyl, wherein the ($C_3$-$C_8$)cycloalkyl may be optionally fused to a phenyl ring or may be independently substituted by one to three $R^{10}$; or 'C-linked' Het$^1$; or $R^7$ and $R^8$, taken together with the nitrogen atom to which they are attached, form a saturated, bridged, 7- to 9-membered ring;

$R^9$ is ($C_1$-$C_6$)alkyloxy; ($C_3$-$C_8$)cycloalkyl, optionally substituted by one to eight F; Het$^1$; or phenyl, optionally independently substituted by one to three $R^6$;

$R^{10}$ is F, Cl or $R^6$;

$R^{11}$ is F; ($C_1$-$C_6$)alkyloxy; ($C_3$-$C_8$)cycloalkyl, optionally substituted by one to eight F; 'C-linked' Het$^1$; or phenyl, optionally independently substituted by one to three $R^6$;

Het$^1$ is a 3- to 8-membered saturated monoheterocycloalkyl comprising one or two ring members selected from —NR$^{12}$— and —O—, said monoheterocycloalkyl being optionally substituted on a ring carbon atom by one to three substituents independently selected from F, ($C_1$-$C_6$)alkyl, ($C_1$-$C_4$)alkyloxy($C_0$-$C_4$)alkylene and ($C_3$-$C_8$)cycloalkyl;

Het$^2$ is a 5- or 6-membered heteroaryl comprising one to three nitrogen atoms, said heteroaryl being optionally substituted by one to three substituents selected from F, Cl, CN and $R^6$; and $R^{12}$ is H, ($C_1$-$C_6$)alkyl or ($C_3$-$C_8$)cycloalkyl, wherein ($C_1$-$C_6$)alkyl and ($C_3$-$C_8$)cycloalkyl are optionally substituted by one to eight F; provided that when Het$^1$ is 'N-linked', $R^{12}$ is absent on the 'N-linked' nitrogen.

2. The compound according to claim 1 wherein Ar$^1$ is phenyl independently substituted by one to three Y.

3. The compound according to claim 1 wherein Ar$^1$ is phenyl independently substituted by one or two Y.

4. The compound according to claim 1 wherein Ar$^1$ is phenyl meta-substituted by Y, para-substituted by Y, or meta- and para-substituted by independent Y.

5. The compound according to claim 4 wherein Y is F; Cl; CN; ($C_1$-$C_8$)alkyl, optionally substituted by ($C_3$-$C_8$)cycloalkyl or by one to eight F; ($C_3$-$C_8$)cycloalkyl, optionally substituted by one to eight F; ($C_1$-$C_6$)alkyloxy, optionally substituted by one to eight F; or ($C_3$-$C_8$)cycloalkyloxy.

6. The compound according to claim 4 wherein $R^1$ is ($C_1$-$C_4$)alkyl or ($C_3$-$C_6$)cycloalkyl.

7. The compound according to claim 4 wherein $R^1$ is methyl or cyclopropyl.

8. The compound according to claim 7 wherein $R^2$, $R^3$ and $R^4$ are independently H, F or Cl.

9. The compound according to claim 7 wherein $R^2$, $R^3$ and $R^4$ are independently H or F.

10. The compound according to claim 9 wherein $R^5$ is H, CN, F, Cl, CH$_3$, C$_2$H$_5$, CF$_3$, —OCH$_3$, —OC$_2$H$_5$ or —OCF$_3$.

11. A compound of formula (I)

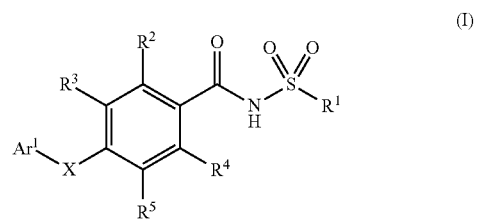

(I)

or a pharmaceutically acceptable salt thereof, wherein

X is O;

Ar$^1$ is (i) naphthyl; or (ii) naphthyl or phenyl each of which is independently substituted by one to three Y;

Y is F; Cl; CN; ($C_1$-$C_8$)alkyl, optionally substituted by ($C_3$-$C_8$)cycloalkyl or one to three F; ($C_3$-$C_8$)cycloalkyl, optionally substituted by one to three F; NR$^7$R$^8$; ($C_1$-$C_8$)alkyloxy, optionally independently substituted by one to three $R^9$; ($C_3$-$C_8$)cycloalkyloxy, wherein ($C_3$-$C_8$)cycloalkyloxy may be optionally fused to a phenyl ring or may be independently substituted by one to three $R^{10}$; phenyl, optionally independently substituted by one to three $R^{10}$; Het$^1$ or Het$^2$;

$R^1$ is ($C_1$-$C_6$)alkyl or ($C_3$-$C_8$)cycloalkyl, each of which is optionally substituted by one to three F;

$R^2$, $R^3$, $R^4$ are independently H, F, Cl or —OCH$_3$;

$R^5$ is H, CN, F, Cl, or $R^6$;

$R^6$ is a group selected from ($C_1$-$C_6$)alkyl and ($C_1$-$C_6$)alkyloxy, wherein each group is optionally substituted by one to five F;

$R^7$ and $R^8$ are independently H; ($C_1$-$C_8$)alkyl, optionally independently substituted by one to three $R^{11}$; ($C_3$-$C_8$)cycloalkyl, wherein ($C_3$-$C_8$)cycloalkyl may be optionally fused to a phenyl ring or may be independently substituted by one to three $R^{10}$; or 'C-linked' Het$^1$; or $R^7$ and $R^8$, taken together with the nitrogen atom to which they are attached, form a saturated, bridged, 7- to 9-membered ring;

$R^9$ is F; ($C_1$-$C_6$)alkyloxy; ($C_3$-$C_8$)cycloalkyl, optionally substituted by one to three F; Het$^1$; or phenyl, optionally independently substituted by one to three $R^6$;

$R^{10}$ is F, Cl or $R^6$;

$R^{11}$ is F; ($C_1$-$C_6$)alkyloxy; ($C_3$-$C_8$)cycloalkyl, optionally substituted by one to three F; 'C-linked' Het$^1$; or phenyl, optionally independently substituted by one to three $R^6$;

Het$^1$ is a 3- to 8-membered saturated monoheterocycloalkyl comprising one or two ring members selected from —NR$^{12}$— and —O—, said monoheterocycloalkyl being optionally substituted on a ring carbon atom by one to three substituents independently selected from F, ($C_1$-$C_6$)alkyl, ($C_1$-$C_4$)alkyloxy($C_0$-$C_4$)alkylene and ($C_3$-$C_8$)cycloalkyl;

Het$^2$ is a 5- or 6-membered heteroaryl comprising one to three nitrogen atoms, said heteroaryl being optionally substituted by one to three substituents selected from F, Cl, CN and $R^6$; and $R^{12}$ is H, ($C_1$-$C_6$)alkyl or ($C_3$-$C_8$)cycloalkyl, wherein ($C_1$-$C_6$)alkyl and ($C_3$-$C_8$)cycloalkyl are optionally substituted by one to three F; provided that when Het$^1$ is 'N-linked', $R^{12}$ is absent on the 'N-linked' nitrogen.

12. A pharmaceutical composition comprising a compound according to claim 1, or a pharmaceutically acceptable salt thereof, and one or more pharmaceutically acceptable excipients.

13. The pharmaceutical composition according to claim 12 further comprising one or more additional therapeutic agents.

14. The compound according to claim 1 that is
4-[4-Chloro-3-(trifluoromethyl)phenoxy]-N-(cyclopropylsulfonyl)benzamide;
5-Chloro-4-(3,4-dichlorophenoxy)-2-fluoro-N-(methylsulfonyl)benzamide;
4-(4-Chloro-2-ethylphenoxy)-2,5-difluoro-N-(methylsulfonyl)benzamide;
4-(3,4-Dichlorophenoxy)-3-ethyl-N-(methylsulfonyl)benzamide;
5-chloro-4-(3-ethoxyphenoxy)-2-fluoro-N-(methylsulfonyl)benzamide;
3-chloro-N-(methylsulfonyl)-4-(2-naphthyloxy)benzamide;
4-[4-chloro-3-(trifluoromethyl)phenoxy]-2-fluoro-5-methyl-N-(methylsulfonyl)benzamide;
5-chloro-4-(3-chloro-4-(trifluoromethyl)phenoxy)-2-fluoro-N-(methylsulfonyl)benzamide;
4-(3,4-dichlorophenoxy)-3-methoxy-N-(methylsulfonyl)benzamide;
4-[4-chloro-3-(trifluoromethyl)phenoxy]-3,6-difluoro-2-methoxy-N-(methylsulfonyl)benzamide;
4-(4-chloro-3-(trifluoromethyl)phenoxy)-2-fluoro-N-(methylsulfonyl)benzamide;
4-[4-chloro-3-(trifluoromethyl)phenoxy]-N-(methylsulfonyl)benzamide;
5-chloro-4-[4-chloro-3-(trifluoromethyl)phenoxy]-2-fluoro-N-(methylsulfonyl)benzamide;
or a pharmaceutically acceptable salt thereof.

15. The compound according to claim 11 that is
5-chloro-4-[3-chloro-4-(trifluoromethoxy)phenoxy]-2-fluoro-N-(methylsulfonyl)benzamide;
5-chloro-4-[4-chloro-2-(difluoromethoxy)phenoxy]-2-fluoro-N-(methylsulfonyl)benzamide;
4-[3-chloro-4-(difluoromethoxy)phenoxy]-2,5-difluoro-N-(methylsulfonyl)benzamide;
5-chloro-4-[4-chloro-3-(trifluoromethoxy)phenoxy]-2-fluoro-N-(methylsulfonyl)benzamide;
or a pharmaceutically acceptable salt thereof.

16. The compound according to claim 1 that is
4-(3,4-Dichlorobenzyl)-N-(methylsulfonyl)benzamide;
4-[(3,4-Dichlorophenyl)sulfanyl]-N-(methylsulfonyl)benzamide;
4-(4-Chloro-2-methoxybenzyl)-2,5-difluoro-N-(methylsulfonyl)benzamide;
3-chloro-4-(4-chloro-3-(trifluoromethyl)phenoxy)-2-fluoro-N-(methylsulfonyl)benzamide;
N-(methylsulfonyl)-4-(3-(trifluoromethyl)phenylamino)benzamide;
4-(3,4-dichlorobenzyl)-3-methoxy-N-(methylsulfonyl)benzamide;
4-(2-chlorophenylthio)-N-(methylsulfonyl)benzamide;
4-(2-methoxyphenylthio)-N-(methylsulfonyl)benzamide;
5-chloro-4-(3,4-dichlorophenylthio)-2-fluoro-N-(methylsulfonyl)benzamide;
4-(4-chloro-3-(trifluoromethyl)phenoxy)-2-methoxy-N-(methylsulfonyl)benzamide;
4-(2-cyanophenoxy)-2,5-difluoro-N-(methylsulfonyl)benzamide;
or a pharmaceutically acceptable salt thereof.

* * * * *